US012587274B2

(12) United States Patent
Prasad et al.

(10) Patent No.: US 12,587,274 B2
(45) Date of Patent: Mar. 24, 2026

(54) SATELLITE OPTIMIZATION MANAGEMENT SYSTEM BASED ON NATURAL LANGUAGE INPUT AND ARTIFICIAL INTELLIGENCE

(71) Applicant: Quantum Generative Materials LLC, Austin, TX (US)

(72) Inventors: Niraj Prasad, Surrey (CA); Deeptanshu Prasad, Vancouver (CA)

(73) Assignee: QUANTUM GENERATIVE MATERIALS LLC, Austin, TX (US)

( * ) Notice: Subject to any disclaimer, the term of this patent is extended or adjusted under 35 U.S.C. 154(b) by 0 days.

(21) Appl. No.: 18/889,237

(22) Filed: Sep. 18, 2024

(65) Prior Publication Data

US 2025/0219718 A1    Jul. 3, 2025

Related U.S. Application Data

(63) Continuation-in-part of application No. 18/600,486, filed on Mar. 8, 2024, and a continuation-in-part of application No. 18/397,993, filed on Dec. 27, 2023.

(Continued)

(51) Int. Cl.
*G06F 17/00*        (2019.01)
*G06F 40/30*        (2020.01)
(Continued)

(52) U.S. Cl.
CPC ......... *H04B 7/18519* (2013.01); *G06F 40/30* (2020.01); *G16C 20/30* (2019.02);
(Continued)

(58) Field of Classification Search
None
See application file for complete search history.

(56) References Cited

U.S. PATENT DOCUMENTS 3,582,016 A    6/1971  Sherman
5,434,796 A    7/1995  Weininger
(Continued)

FOREIGN PATENT DOCUMENTS

AU    1996056667 A1    1/1997
AU        714247 B2    12/1999
(Continued)

OTHER PUBLICATIONS

Liu et al., "Generative artificial intelligence and its applications in materials science: Current situation and future perspectives," Journal of Materiomics, vol. 9, 2023, pp. 798-816.
Merchant et al., "Scaling deep learning for materials discovery," Nature, vol. 624, Dec. 7, 2023, 11 pages.
(Continued)

*Primary Examiner* — Satwant K Singh
(74) *Attorney, Agent, or Firm* — Zilka-Kotab, P.C.

(57)        ABSTRACT

Satellite optimization management systems based on natural language input and artificial intelligence methods are provided. Conventional satellite management systems require understanding how to control and program satellites. As the number of satellites are deployed, the need to control such satellites by natural language instruction increases. The systems and methods disclosed herein include a natural language processing module configured to receive and interpret user input expressed in natural language to determine a user's intent and map it to specific tasks. In order to correctly determine a user's intent, a neural network with artificial intelligence models may be used. Such user's intent may be used to generate and execute satellite command sequences based on operational tasks derived from the user's natural language inputs. Such natural language input and derived intents can be translated into command sequences to that are applicable across an entire constellation of a large number of satellites.

17 Claims, 29 Drawing Sheets

Related U.S. Application Data

(60) Provisional application No. 63/574,141, filed on Apr. 3, 2023, provisional application No. 63/571,281, filed on Mar. 28, 2023.

(51) Int. Cl.

| | |
|---|---|
| *G16C 20/30* | (2019.01) |
| *G16C 20/70* | (2019.01) |
| *G16C 60/00* | (2019.01) |
| *H04B 7/185* | (2006.01) |
| *G06F 30/27* | (2020.01) |
| *G06N 20/10* | (2019.01) |

(52) U.S. Cl.

CPC ............. *G16C 20/70* (2019.02); *G16C 60/00* (2019.02); *G06F 30/27* (2020.01); *G06N 20/10* (2019.01)

(56) References Cited

U.S. PATENT DOCUMENTS

| | | | |
|---|---|---|---|
| 5,926,113 A | 7/1999 | Jones et al. |
| 5,986,575 A | 11/1999 | Jones et al. |
| 6,072,433 A | 6/2000 | Young et al. |
| 6,106,562 A | 8/2000 | Teter et al. |
| 6,243,026 B1 | 6/2001 | Jones et al. |
| 6,287,742 B1 | 9/2001 | Yoon |
| 6,295,514 B1 | 9/2001 | Agrafiotis et al. |
| 6,355,392 B1 | 3/2002 | Yoon |
| 6,387,583 B1 | 5/2002 | Yoon |
| 6,421,612 B1 | 7/2002 | Agrafiotis et al. |
| 6,432,605 B1 | 8/2002 | Yoon |
| 6,587,845 B1 | 7/2003 | Braunheim |
| 6,625,585 B1 | 9/2003 | MacCuish et al. |
| 6,647,342 B2 | 11/2003 | Iglesia et al. |
| 6,763,309 B2 | 7/2004 | Kieken et al. |
| 6,813,615 B1 | 11/2004 | Colasanti et al. |
| 6,839,634 B1 | 1/2005 | Satoh et al. |
| 6,862,533 B2 | 3/2005 | Strehlau et al. |
| 6,904,423 B1 | 6/2005 | Nicolaou et al. |
| 6,988,041 B2 | 1/2006 | Benson et al. |
| 7,024,313 B2 | 4/2006 | Lee et al. |
| 7,054,757 B2 | 5/2006 | Agrafiotis et al. |
| 7,072,777 B1 | 7/2006 | Wakui et al. |
| 7,103,434 B2 | 9/2006 | Chernyak et al. |
| 7,164,117 B2 | 1/2007 | Breed et al. |
| 7,188,055 B2 | 3/2007 | Agrafiotis et al. |
| 7,194,359 B2 | 3/2007 | Duffy et al. |
| 7,246,047 B2 | 7/2007 | Ghaboussi et al. |
| 7,272,766 B2 | 9/2007 | Sakezles |
| 7,292,958 B2 | 11/2007 | Ceder et al. |
| 7,299,135 B2 | 11/2007 | Thayer |
| 7,319,040 B2 | 1/2008 | Vaidyanathan et al. |
| 7,330,784 B2 | 2/2008 | Johnson et al. |
| 7,386,372 B2 | 6/2008 | Breed et al. |
| 7,440,762 B2 | 10/2008 | Maloney et al. |
| 7,447,614 B2 | 11/2008 | Ghaboussi et al. |
| 7,467,057 B2 | 12/2008 | Sheiretov et al. |
| 7,482,163 B1 | 1/2009 | Kilic et al. |
| 7,499,841 B2 | 3/2009 | Hoffman |
| 7,523,803 B2 | 4/2009 | Breed |
| 7,555,566 B2 | 6/2009 | Blumrich et al. |
| 7,596,242 B2 | 9/2009 | Breed et al. |
| 7,599,822 B2 | 10/2009 | Hearn et al. |
| 7,663,502 B2 | 2/2010 | Breed |
| 7,672,826 B2 | 3/2010 | Chen et al. |
| 7,676,329 B2 | 3/2010 | Garczarek et al. |
| 7,676,352 B1 | 3/2010 | Van Peursem et al. |
| 7,687,146 B1 | 3/2010 | Freitas, Jr. |
| 7,702,467 B2 | 4/2010 | Duffy |
| 7,747,391 B2 | 6/2010 | Gustafsson et al. |
| 7,751,986 B2 | 7/2010 | Gustafsson et al. |
| 7,751,988 B2 | 7/2010 | Kita et al. |
| 7,827,129 B2 | 11/2010 | Hu et al. |
| 7,856,321 B2 | 12/2010 | Lanza et al. |
| 7,882,052 B2 | 2/2011 | Szathmary et al. |
| 7,925,274 B2 | 4/2011 | Anderson et al. |
| 7,987,082 B2 | 7/2011 | Van Peursem et al. |
| 8,036,867 B2 | 10/2011 | Prakash et al. |
| 8,050,883 B2 | 11/2011 | Sheiretov et al. |
| 8,054,203 B2 | 11/2011 | Breed et al. |
| 8,082,130 B2 | 12/2011 | Guo et al. |
| 8,082,131 B2 | 12/2011 | Kusakabe |
| 8,095,344 B2 | 1/2012 | Ghaboussi et al. |
| 8,209,070 B2 | 6/2012 | Hamilton |
| 8,250,133 B2 | 8/2012 | Blumrich et al. |
| 8,311,955 B2 | 11/2012 | Chimenti et al. |
| 8,314,245 B2 | 11/2012 | Yaghi et al. |
| 8,336,826 B2 | 12/2012 | Janson |
| 8,346,525 B2 | 1/2013 | Chen et al. |
| 8,375,032 B2 | 2/2013 | Birdwell et al. |
| 8,392,418 B2 | 3/2013 | Birdwell et al. |
| 8,396,671 B2 | 3/2013 | Jojic et al. |
| 8,396,870 B2 | 3/2013 | Birdwell et al. |
| 8,423,307 B2 | 4/2013 | Nakamura |
| 8,423,337 B2 | 4/2013 | Hsu et al. |
| 8,452,716 B2 | 5/2013 | Howley et al. |
| 8,478,535 B2 | 7/2013 | Jojic et al. |
| 8,498,851 B2 | 7/2013 | Ehrnsperger et al. |
| 8,540,802 B2 | 9/2013 | Yaghi et al. |
| 8,667,049 B2 | 3/2014 | Blumrich et al. |
| 8,671,369 B2 | 3/2014 | Ahn |
| 8,676,556 B2 | 3/2014 | Deffenbaugh et al. |
| 8,713,019 B2 | 4/2014 | Birdwell et al. |
| 8,762,379 B2 | 6/2014 | Birdwell et al. |
| 8,775,427 B2 | 7/2014 | Birdwell et al. |
| 8,775,428 B2 | 7/2014 | Birdwell et al. |
| 8,780,352 B2 | 7/2014 | Freese et al. |
| 8,809,546 B2 | 8/2014 | Yaghi et al. |
| 8,843,509 B2 | 9/2014 | Csanyi et al. |
| 8,849,575 B2 | 9/2014 | Gustafsson et al. |
| 8,880,246 B1 | 11/2014 | Karpenko et al. |
| 8,948,442 B2 | 2/2015 | Breed et al. |
| 8,949,157 B2 | 2/2015 | Okuno et al. |
| 8,954,207 B1 | 2/2015 | Anzalone et al. |
| 8,965,740 B2 | 2/2015 | Safonov et al. |
| 8,977,576 B2 | 3/2015 | Macready |
| 9,009,009 B2 | 4/2015 | Oganov et al. |
| 9,043,052 B2 | 5/2015 | So et al. |
| 9,047,513 B2 | 6/2015 | Derzhi et al. |
| 9,086,383 B2 | 7/2015 | Tunheim et al. |
| 9,103,767 B2 | 8/2015 | Freese et al. |
| 9,274,036 B2 | 3/2016 | Malik et al. |
| 9,341,687 B2 | 5/2016 | Donnangelo et al. |
| 9,384,320 B2 | 7/2016 | Church |
| 9,395,294 B2 | 7/2016 | Tunheim et al. |
| 9,401,684 B2 | 7/2016 | Ren et al. |
| 9,542,511 B2 | 1/2017 | Chen et al. |
| 9,557,299 B2 | 1/2017 | Salem et al. |
| 9,557,813 B2 | 1/2017 | Yairi et al. |
| 9,665,694 B2 | 5/2017 | Cope |
| 9,672,319 B1 | 6/2017 | Cao et al. |
| 9,684,771 B2 | 6/2017 | Cope et al. |
| 9,727,034 B1 | 8/2017 | Ross et al. |
| 9,727,675 B2 | 8/2017 | Liu et al. |
| 9,727,824 B2 | 8/2017 | Rose et al. |
| 9,757,706 B2 | 9/2017 | Cronin |
| 9,771,795 B2 | 9/2017 | Knight et al. |
| 9,782,491 B2 | 10/2017 | Khanna |
| 9,811,849 B2 | 11/2017 | Bursey |
| 9,836,563 B2 | 12/2017 | Liu et al. |
| 9,881,111 B2 | 1/2018 | Liu et al. |
| 9,962,677 B2 | 5/2018 | Cronin |
| 9,967,696 B2 | 5/2018 | Agostinelli et al. |
| 9,996,661 B2 | 6/2018 | Gustafsson et al. |
| 9,996,778 B2 | 6/2018 | Church |
| 10,002,214 B2 | 6/2018 | Thompson et al. |
| 10,020,876 B2 | 7/2018 | Trutna et al. |
| 10,043,261 B2 | 8/2018 | Bhaskar et al. |
| 10,049,173 B2 | 8/2018 | Liu et al. |
| 10,061,300 B1 | 8/2018 | Coffman et al. |
| 10,073,440 B1 | 9/2018 | Fenoglietto et al. |
| 10,084,536 B1 | 9/2018 | Schloemer |
| 10,085,200 B1 | 9/2018 | Schloemer |

(56)  References Cited

U.S. PATENT DOCUMENTS

| 10,102,476 B2 | 10/2018 | Caraviello et al. |
| 10,108,754 B2 | 10/2018 | Chen et al. |
| 10,127,342 B2 | 11/2018 | Xin et al. |
| 10,131,583 B2 | 11/2018 | Pearl, Jr. et al. |
| 10,133,852 B2 | 11/2018 | Lyakhov et al. |
| 10,194,295 B2 | 1/2019 | Agostinelli et al. |
| 10,196,555 B2 | 2/2019 | Fathi Najafabadi |
| 10,216,910 B2 | 2/2019 | Karthikeyan et al. |
| 10,223,499 B2 | 3/2019 | Weaver et al. |
| 10,241,426 B2 | 3/2019 | Tinnemans |
| 10,274,933 B2 | 4/2019 | Coffman et al. |
| 10,281,902 B2 | 5/2019 | Coffman et al. |
| 10,295,462 B1 | 5/2019 | Yap et al. |
| 10,311,214 B2 | 6/2019 | McLaughlin et al. |
| 10,318,881 B2 | 6/2019 | Rose et al. |
| 10,324,475 B2 | 6/2019 | Cui et al. |
| 10,338,565 B1 | 7/2019 | Coffman et al. |
| 10,345,252 B2 | 7/2019 | Vecchio et al. |
| 10,353,378 B2 | 7/2019 | Shapiro et al. |
| 10,360,506 B2 | 7/2019 | O'Brien et al. |
| 10,366,324 B2 | 7/2019 | Riley et al. |
| 10,366,779 B2 | 7/2019 | Hsu et al. |
| 10,392,669 B2 | 8/2019 | Sowadski |
| 10,401,224 B2 | 9/2019 | Bischoff et al. |
| 10,401,312 B2 | 9/2019 | Takis et al. |
| 10,402,520 B2 | 9/2019 | Oh et al. |
| 10,409,950 B2 | 9/2019 | Dweik |
| 10,415,370 B2 | 9/2019 | Pearl, Jr. et al. |
| 10,430,395 B2 | 10/2019 | Botea et al. |
| 10,434,716 B2 | 10/2019 | Morovic et al. |
| 10,460,220 B2 | 10/2019 | Church |
| 10,461,815 B2 | 10/2019 | Wang |
| 10,467,534 B1 | 11/2019 | Brent et al. |
| 10,474,976 B2 | 11/2019 | Clancy et al. |
| 10,489,525 B2 | 11/2019 | Joshi et al. |
| 10,495,590 B2 | 12/2019 | Vecchio et al. |
| 10,496,781 B2 | 12/2019 | Fang et al. |
| 10,497,464 B2 | 12/2019 | Siva Kimar et al. |
| 10,515,715 B1 | 12/2019 | Pappas et al. |
| 10,516,725 B2 | 12/2019 | Moroz et al. |
| 10,519,770 B2 | 12/2019 | Chen et al. |
| 10,529,444 B1 | 1/2020 | Zhou et al. |
| 10,532,330 B2 | 1/2020 | Diallo et al. |
| 10,533,937 B1 | 1/2020 | Shehri et al. |
| 10,535,422 B2 | 1/2020 | Lekivetz et al. |
| 10,546,072 B2 | 1/2020 | Holland et al. |
| 10,558,195 B2 | 2/2020 | Coffman et al. |
| 10,558,199 B2 | 2/2020 | Fenoglietto et al. |
| 10,566,079 B2 | 2/2020 | Martinis et al. |
| 10,607,109 B2 | 3/2020 | Sagong et al. |
| 10,614,258 B1 | 4/2020 | Ng et al. |
| 10,616,774 B2 | 4/2020 | Narasimha et al. |
| 10,628,868 B2 | 4/2020 | Bursey |
| 10,636,636 B2 | 4/2020 | Tautenhahn et al. |
| 10,637,142 B1 | 4/2020 | Tran et al. |
| 10,643,262 B2 | 5/2020 | Bursey |
| 10,643,324 B2 | 5/2020 | Al Shehri et al. |
| 10,649,440 B2 | 5/2020 | Fenoglietto et al. |
| 10,650,114 B2 | 5/2020 | Dweik |
| 10,650,427 B2 | 5/2020 | Bursey |
| 10,659,148 B2 * | 5/2020 | Trutna .............. H04B 7/18519 |
| 10,665,330 B2 | 5/2020 | Cecchi et al. |
| 10,684,388 B2 | 6/2020 | Perkins et al. |
| 10,706,626 B1 | 7/2020 | Brent et al. |
| 10,708,718 B1 | 7/2020 | Zavesky et al. |
| 10,712,727 B2 | 7/2020 | Coffman et al. |
| 10,748,198 B2 | 8/2020 | Bursey |
| 10,769,324 B2 | 9/2020 | Matusik et al. |
| 10,776,560 B2 | 9/2020 | Moroz et al. |
| 10,776,712 B2 | 9/2020 | Oono et al. |
| 10,779,146 B2 | 9/2020 | Agostinelli et al. |
| 10,790,045 B1 | 9/2020 | Goyal et al. |
| 10,803,211 B2 | 10/2020 | Dweik et al. |
| 10,810,469 B2 | 10/2020 | Sunkavalli et al. |
| 10,824,909 B2 | 11/2020 | Ros Sanchez et al. |
| 10,831,957 B2 | 11/2020 | Liu et al. |
| 10,837,931 B2 | 11/2020 | Donnangelo et al. |
| 10,838,939 B2 | 11/2020 | Walder et al. |
| 10,839,941 B1 | 11/2020 | Pappas et al. |
| 10,839,942 B1 | 11/2020 | Pappas et al. |
| 10,847,254 B2 | 11/2020 | Aykol |
| 10,857,736 B2 | 12/2020 | Morovic et al. |
| 10,860,001 B2 | 12/2020 | Fenoglietto et al. |
| 10,866,242 B2 | 12/2020 | Farokhzad et al. |
| 10,867,085 B2 | 12/2020 | Dweik et al. |
| 10,871,444 B2 | 12/2020 | Al Shehri et al. |
| 10,885,231 B2 | 1/2021 | Matsumura et al. |
| 10,885,383 B2 | 1/2021 | Sohn et al. |
| 10,891,277 B2 | 1/2021 | Botea et al. |
| 10,896,744 B2 | 1/2021 | Maxson et al. |
| 10,902,238 B2 | 1/2021 | Herring |
| 10,902,943 B2 | 1/2021 | Zhang et al. |
| 10,915,808 B2 | 2/2021 | Hara et al. |
| 10,922,617 B2 | 2/2021 | Babbush et al. |
| 10,923,214 B2 | 2/2021 | Fan et al. |
| 10,929,534 B2 | 2/2021 | Chistyakov et al. |
| 10,938,473 B1 | 3/2021 | Regada Alvarez et al. |
| 10,943,701 B2 | 3/2021 | Cole, Jr. et al. |
| 10,957,419 B2 | 3/2021 | Yoo et al. |
| 10,963,599 B2 | 3/2021 | Dweik |
| 10,965,529 B2 | 3/2021 | Magzimof et al. |
| 10,969,773 B2 | 4/2021 | Yennie et al. |
| 10,977,397 B2 | 4/2021 | Dweik et al. |
| 10,984,145 B1 | 4/2021 | Hutchinson et al. |
| 10,998,087 B2 | 5/2021 | McNamara et al. |
| 11,004,568 B2 | 5/2021 | Dweik et al. |
| 11,009,863 B2 | 5/2021 | Bharadwaj et al. |
| 11,010,513 B2 | 5/2021 | Weiss |
| 11,010,637 B2 | 5/2021 | Visentini Scarzanella et al. |
| 11,017,314 B2 | 5/2021 | Yoo et al. |
| 11,023,639 B2 | 6/2021 | Stokbro et al. |
| 11,023,837 B2 | 6/2021 | Furu et al. |
| 11,036,898 B2 | 6/2021 | Chouaib et al. |
| 11,048,831 B2 | 6/2021 | De Keyser et al. |
| 11,048,842 B2 | 6/2021 | Dittel et al. |
| 11,049,590 B1 | 6/2021 | Lee et al. |
| 11,049,605 B1 | 6/2021 | Peters |
| 11,055,356 B2 | 7/2021 | Ritchey et al. |
| 11,055,639 B1 | 7/2021 | Cay et al. |
| 11,068,631 B2 | 7/2021 | Oh et al. |
| 11,070,950 B2 | 7/2021 | Zavesky et al. |
| 11,080,607 B1 | 8/2021 | Demtchenko et al. |
| 11,086,292 B2 | 8/2021 | Coffman et al. |
| 11,087,025 B2 | 8/2021 | Santana de Oliveira et al. |
| 11,087,055 B2 | 8/2021 | Hegde et al. |
| 11,087,861 B2 | 8/2021 | Takeda et al. |
| 11,092,694 B2 | 8/2021 | Cui et al. |
| 11,105,942 B2 | 8/2021 | Alwon |
| 11,106,977 B2 | 8/2021 | Khomami Abadi et al. |
| 11,113,611 B2 | 9/2021 | Han et al. |
| 11,113,627 B2 | 9/2021 | Levy |
| 11,114,183 B2 | 9/2021 | McNamara et al. |
| 11,120,913 B2 | 9/2021 | Dey et al. |
| 11,120,914 B2 | 9/2021 | Dey et al. |
| 11,126,695 B2 | 9/2021 | Minami et al. |
| 11,127,488 B1 | 9/2021 | Bajpai et al. |
| 11,128,045 B2 | 9/2021 | Tran et al. |
| 11,132,621 B2 | 9/2021 | Botea et al. |
| 11,144,035 B2 | 10/2021 | Gupta et al. |
| 11,152,125 B2 | 10/2021 | Spiro et al. |
| 11,158,400 B2 | 10/2021 | Nichols et al. |
| 11,162,888 B2 | 11/2021 | Al Shehri et al. |
| 11,162,902 B2 | 11/2021 | Ragan et al. |
| 11,170,141 B2 | 11/2021 | Bai et al. |
| 11,173,477 B2 | 11/2021 | Zhong et al. |
| 11,175,250 B2 | 11/2021 | Vecchio et al. |
| 11,176,462 B1 | 11/2021 | Bastas et al. |
| 11,182,361 B2 | 11/2021 | Botea et al. |
| 11,187,826 B2 | 11/2021 | Laugier et al. |
| 11,189,362 B2 | 11/2021 | Liu et al. |
| 11,193,884 B2 | 12/2021 | Frenkel et al. |
| 11,196,503 B2 | 12/2021 | Lu et al. |
| 11,205,139 B2 | 12/2021 | Woodbury |
| 11,230,741 B2 | 1/2022 | Sowadski |

(56)  References Cited

U.S. PATENT DOCUMENTS

| | | |
|---|---|---|
| 11,232,241 B2 | 1/2022 | Narayanan et al. |
| 11,240,579 B2 | 2/2022 | Jumbe et al. |
| 11,256,995 B1 | 2/2022 | Bucher et al. |
| 11,263,534 B1 | 3/2022 | Prat et al. |
| 11,264,140 B1 | 3/2022 | Tal et al. |
| 11,267,972 B2 | 3/2022 | Short et al. |
| 11,281,820 B2 | 3/2022 | Roberts et al. |
| 11,282,269 B2 | 3/2022 | Laugier et al. |
| 11,288,757 B2 | 3/2022 | Lingras et al. |
| 11,289,178 B2 | 3/2022 | Dey et al. |
| 11,294,367 B2 | 4/2022 | Kludt et al. |
| 11,294,986 B2 | 4/2022 | Mezzacapo et al. |
| 11,301,756 B2 | 4/2022 | Yoon et al. |
| 11,308,055 B2 | 4/2022 | Walder et al. |
| 11,309,063 B2 | 4/2022 | Dey et al. |
| 11,309,753 B2 | 4/2022 | Kaul |
| 11,315,663 B2 | 4/2022 | Pappas et al. |
| 11,317,262 B2 | 4/2022 | Agostinelli et al. |
| 11,320,506 B2 | 5/2022 | Sun et al. |
| 11,327,201 B2 | 5/2022 | Wood et al. |
| 11,330,264 B2 | 5/2022 | Zhou et al. |
| 11,338,942 B2 | 5/2022 | Blomquist |
| 11,341,305 B2 | 5/2022 | Kim et al. |
| 11,342,046 B2 | 5/2022 | Sarmiento et al. |
| 11,342,049 B2 | 5/2022 | Pappas et al. |
| 11,347,201 B2 | 5/2022 | Coffman et al. |
| 11,347,810 B2 | 5/2022 | Kaufman et al. |
| 11,347,908 B2 | 5/2022 | Matusik et al. |
| 11,348,664 B1 | 5/2022 | Kaneko et al. |
| 11,353,394 B2 | 6/2022 | Murphy et al. |
| 11,355,240 B2 | 6/2022 | Hirsch et al. |
| 11,367,006 B1 | 6/2022 | Kamuntavicius et al. |
| 11,373,732 B2 | 6/2022 | Aliper et al. |
| 11,379,630 B2 | 7/2022 | Dweik |
| 11,379,637 B2 | 7/2022 | Collins et al. |
| 11,385,887 B2 | 7/2022 | Schmit et al. |
| 11,386,541 B2 | 7/2022 | Al Shehri et al. |
| 11,392,998 B1 | 7/2022 | Kwak et al. |
| 11,396,806 B2 | 7/2022 | Li et al. |
| 11,397,895 B2 | 7/2022 | Lu et al. |
| 11,398,297 B2 | 7/2022 | Chang |
| 11,403,496 B2 | 8/2022 | Elenes et al. |
| 11,404,144 B1 | 8/2022 | Kang et al. |
| 11,408,898 B2 | 8/2022 | Farokhzad et al. |
| 11,410,752 B2 | 8/2022 | Trice et al. |
| 11,416,683 B2 | 8/2022 | Park et al. |
| 11,423,196 B2 | 8/2022 | Herring |
| 11,424,008 B2 | 8/2022 | Lee et al. |
| 11,429,662 B2 | 8/2022 | Malkosh et al. |
| 11,429,822 B2 | 8/2022 | Chae |
| 11,435,360 B2 | 9/2022 | Farokhzad et al. |
| 11,443,417 B2 | 9/2022 | Nipe et al. |
| 11,446,253 B2 | 9/2022 | Mitragotri et al. |
| 11,449,462 B2 | 9/2022 | Chen et al. |
| 11,449,708 B2 | 9/2022 | Sohn et al. |
| 11,450,225 B1 | 9/2022 | Kilari et al. |
| 11,450,407 B1 | 9/2022 | Laniado et al. |
| 11,450,410 B2 | 9/2022 | Yoo et al. |
| 11,455,439 B2 | 9/2022 | Mailoa et al. |
| 11,455,440 B2 | 9/2022 | Takeda |
| 11,461,519 B2 | 10/2022 | Lu et al. |
| 11,462,303 B2 | 10/2022 | Elemento et al. |
| 11,462,304 B2 | 10/2022 | Lee et al. |
| 11,475,187 B2 | 10/2022 | Teplinsky et al. |
| 11,475,340 B2 | 10/2022 | Han et al. |
| 11,476,964 B2 | 10/2022 | Lu et al. |
| 11,481,549 B2 | 10/2022 | McCarthy et al. |
| 11,488,062 B1 | 11/2022 | Earthman et al. |
| 11,488,226 B2 | 11/2022 | Daware et al. |
| 11,491,729 B2 | 11/2022 | Prabha Narra et al. |
| 11,493,475 B2 | 11/2022 | Suram et al. |
| 11,495,326 B2 | 11/2022 | Liu et al. |
| 11,501,037 B2 | 11/2022 | Gecer Ulu et al. |
| 11,501,042 B2 | 11/2022 | Steingrimsson et al. |
| 11,501,195 B2 | 11/2022 | Rose et al. |
| 11,501,854 B2 | 11/2022 | Morieux et al. |
| 11,508,463 B2 | 11/2022 | Kubis et al. |
| 11,510,405 B2 | 11/2022 | Grant |
| 11,511,491 B2 | 11/2022 | Dheeradhada et al. |
| 11,512,345 B1 | 11/2022 | Lee et al. |
| 11,520,310 B2 | 12/2022 | Zubarev et al. |
| 11,520,953 B2 | 12/2022 | Lill et al. |
| 11,521,711 B2 | 12/2022 | Murthy |
| 11,535,954 B2 | 12/2022 | Czinner et al. |
| 11,537,898 B2 | 12/2022 | Hegde et al. |
| 11,538,591 B2 | 12/2022 | Dweik |
| 11,539,587 B2 | 12/2022 | Magzimof et al. |
| 11,545,238 B2 | 1/2023 | Greving et al. |
| 11,545,239 B1 | 1/2023 | Zhang et al. |
| 11,551,037 B2 | 1/2023 | Gavranovic et al. |
| 11,551,083 B2 | 1/2023 | Li et al. |
| 11,553,075 B2 | 1/2023 | Hwang et al. |
| 11,558,451 B2 | 1/2023 | Sgobba et al. |
| 11,562,226 B2 | 1/2023 | Saito |
| 11,562,807 B2 | 1/2023 | Maiti et al. |
| 11,567,086 B2 | 1/2023 | Farokhzad et al. |
| 11,570,030 B2 | 1/2023 | Sahin et al. |
| 11,574,168 B1 | 2/2023 | Yan |
| 11,574,253 B2 | 2/2023 | Santos et al. |
| 11,574,702 B2 | 2/2023 | Jafri et al. |
| 11,574,703 B2 | 2/2023 | Abeliuk et al. |
| 11,578,481 B1 | 2/2023 | Kohut |
| 11,581,067 B2 | 2/2023 | Kwon et al. |
| 11,581,965 B2 | 2/2023 | O'Shea et al. |
| 11,586,161 B2 | 2/2023 | Lammens |
| 11,586,172 B2 | 2/2023 | Lobo Fenoglietto et al. |
| 11,586,968 B2 | 2/2023 | King et al. |
| 11,586,982 B2 | 2/2023 | Hegde |
| 11,587,643 B2 | 2/2023 | Lee et al. |
| 11,587,645 B2 | 2/2023 | Amimeur et al. |
| 11,587,646 B2 | 2/2023 | Colby et al. |
| 11,590,634 B2 | 2/2023 | Beacham, Jr. et al. |
| 11,593,814 B2 | 2/2023 | Routray et al. |
| 11,594,305 B2 | 2/2023 | Tregger et al. |
| 11,596,917 B2 | 3/2023 | Woods et al. |
| 11,599,794 B1 | 3/2023 | Yan |
| 11,604,984 B2 | 3/2023 | Sharma et al. |
| 11,610,132 B2 | 3/2023 | Hewage et al. |
| 11,610,139 B2 | 3/2023 | Bucher et al. |
| 11,610,238 B1 | 3/2023 | Kwak et al. |
| 11,615,324 B2 | 3/2023 | Pabrinkis et al. |
| 11,621,059 B2 | 4/2023 | Miao et al. |
| 11,629,593 B2 | 4/2023 | Knight et al. |
| 11,630,057 B2 | 4/2023 | Murphy et al. |
| 11,636,395 B2 | 4/2023 | Dupont De Dinechin |
| 11,645,435 B2 | 5/2023 | Van der Velden |
| 11,650,348 B2 | 5/2023 | Perkins et al. |
| 11,651,122 B2 | 5/2023 | Chen |
| 11,651,838 B2 | 5/2023 | Narayanan et al. |
| 11,651,839 B2 | 5/2023 | Sankaranarayanan et al. |
| 11,651,841 B2 | 5/2023 | Oskooei et al. |
| 11,651,860 B2 | 5/2023 | Oskooei et al. |
| 11,663,462 B2 | 5/2023 | Wang et al. |
| 11,664,093 B2 | 5/2023 | Denmark et al. |
| 11,664,094 B2 | 5/2023 | Lin et al. |
| 11,664,690 B2 | 5/2023 | Kaul |
| 11,666,598 B2 | 6/2023 | Davenport Huyer et al. |
| 11,669,063 B2 | 6/2023 | De Waele et al. |
| 11,669,781 B2 | 6/2023 | Han |
| 11,670,042 B2 | 6/2023 | Boubekeur et al. |
| 11,670,403 B2 | 6/2023 | Kim et al. |
| 11,675,334 B2 | 6/2023 | Zubarev et al. |
| 11,680,063 B2 | 6/2023 | Polykovskiy et al. |
| 11,681,775 B2 | 6/2023 | Babbush |
| 11,681,953 B2 | 6/2023 | Drake et al. |
| 11,693,388 B2 | 7/2023 | Coffman et al. |
| 11,696,735 B2 | 7/2023 | Buckler et al. |
| 11,698,623 B2 | 7/2023 | Coffman et al. |
| 11,699,505 B2 | 7/2023 | Kanamarlapudi et al. |
| 11,704,541 B2 | 7/2023 | Li et al. |
| 11,710,045 B2 | 7/2023 | Lee |
| 11,710,049 B2 | 7/2023 | Tal et al. |
| 11,710,542 B2 | 7/2023 | Bowman |
| 11,714,933 B2 | 8/2023 | Dweik |

(56) References Cited

U.S. PATENT DOCUMENTS

| | | |
|---|---|---|
| 11,721,413 B2 | 8/2023 | Tagade et al. |
| 11,727,282 B2 | 8/2023 | Feinberg et al. |
| 11,728,011 B2 | 8/2023 | Tavernelli et al. |
| 11,728,012 B2 | 8/2023 | Pappas et al. |
| 11,731,317 B1 | 8/2023 | Stewart et al. |
| 11,734,387 B2 | 8/2023 | Mezzacapo et al. |
| 11,735,291 B2 | 8/2023 | Stober et al. |
| 11,735,292 B2 | 8/2023 | Kishimoto et al. |
| 11,742,057 B2 | 8/2023 | Laniado et al. |
| 11,742,060 B2 | 8/2023 | Stec et al. |
| 11,747,314 B2 | 9/2023 | Choi et al. |
| 11,747,480 B2 | 9/2023 | Goldstein et al. |
| 11,748,640 B2 | 9/2023 | Kudva et al. |
| 11,754,536 B2 | 9/2023 | Kassis et al. |
| 11,763,181 B2 | 9/2023 | Rothstein et al. |
| 11,776,666 B2 | 10/2023 | Neukart et al. |
| 11,782,396 B2 | 10/2023 | Lovell et al. |
| 11,787,947 B2 | 10/2023 | Knowlton et al. |
| 11,790,044 B2 | 10/2023 | Elenes et al. |
| 11,790,264 B2 | 10/2023 | Duerig et al. |
| 11,791,018 B1 | 10/2023 | Kolouri et al. |
| 11,797,744 B1 | 10/2023 | Chuang et al. |
| 11,798,655 B2 | 10/2023 | Hama |
| 11,798,657 B2 | 10/2023 | Bhavnagri |
| 11,798,658 B2 | 10/2023 | Song et al. |
| 11,803,522 B2 | 10/2023 | Nishiuchi et al. |
| 11,816,122 B1 | 11/2023 | He et al. |
| 11,816,578 B2 | 11/2023 | Yoon et al. |
| 11,823,070 B2 | 11/2023 | Zahn et al. |
| 11,824,275 B2 | 11/2023 | Tran et al. |
| 11,827,381 B2 | 11/2023 | Blomquist |
| 11,829,390 B2 | 11/2023 | Fu |
| 11,829,692 B1 | 11/2023 | Zorian et al. |
| 11,836,109 B2 | 12/2023 | Chen et al. |
| 11,836,633 B2 | 12/2023 | Nemirovsky et al. |
| 11,837,327 B2 | 12/2023 | Westcott et al. |
| 11,837,333 B1 | 12/2023 | Shuang et al. |
| 11,842,794 B2 | 12/2023 | Luo et al. |
| 11,842,800 B2 | 12/2023 | Das et al. |
| 11,847,532 B2 | 12/2023 | Drake et al. |
| 11,848,076 B2 | 12/2023 | Lee et al. |
| 11,852,598 B2 | 12/2023 | Aguiar |
| 11,853,032 B2 | 12/2023 | Chan et al. |
| 11,854,670 B2 | 12/2023 | Georgopoulos et al. |
| 11,854,671 B2 | 12/2023 | Rong et al. |
| 11,854,672 B2 | 12/2023 | Kwon et al. |
| 11,861,880 B2 | 1/2024 | Cebulski et al. |
| 11,862,300 B1 | 1/2024 | Schmidt et al. |
| 11,869,629 B2 | 1/2024 | Laniado et al. |
| 11,869,756 B2 | 1/2024 | Shinagawa et al. |
| 11,891,882 B2 | 2/2024 | Zhang |
| 11,893,326 B2 | 2/2024 | Daware et al. |
| 11,893,498 B2 | 2/2024 | Aliper et al. |
| 11,894,107 B2 | 2/2024 | Setia et al. |
| 11,896,003 B2 | 2/2024 | Grant |
| 11,897,818 B2 | 2/2024 | Bauchy et al. |
| 11,900,191 B2 | 2/2024 | Church |
| 11,900,225 B2 | 2/2024 | Oono et al. |
| 11,900,277 B2 | 2/2024 | Thomsen et al. |
| 11,900,582 B2 | 2/2024 | Choi et al. |
| 11,901,045 B2 | 2/2024 | Katsuki |
| 11,906,424 B2 | 2/2024 | Jarrahi et al. |
| 11,907,812 B2 | 2/2024 | Yang et al. |
| 11,914,931 B2 | 2/2024 | Kumar et al. |
| 11,915,103 B2 | 2/2024 | McClean |
| 11,915,105 B2 | 2/2024 | Steingrimsson et al. |
| 11,915,108 B2 | 2/2024 | Kabir et al. |
| 11,915,798 B2 | 2/2024 | Jippo |
| 11,915,799 B2 | 2/2024 | Minami et al. |
| 11,923,050 B2 | 3/2024 | Pyzer-Knapp et al. |
| 11,928,182 B1 | 3/2024 | Arici et al. |
| 11,933,453 B2 | 3/2024 | Swift et al. |
| 11,934,360 B2 | 3/2024 | Nishiuchi et al. |
| 11,934,929 B2 | 3/2024 | Woodbury |
| 11,934,938 B2 | 3/2024 | Hara et al. |
| 11,940,488 B2 | 3/2024 | Chism, II |
| 11,942,191 B2 | 3/2024 | Rong et al. |
| 11,942,192 B2 | 3/2024 | Tavernelli et al. |
| 11,945,994 B1 | 4/2024 | Jandhyala et al. |
| 11,947,882 B2 | 4/2024 | Dweik et al. |
| 11,948,665 B2 | 4/2024 | Madani et al. |
| 11,955,208 B2 | 4/2024 | Elemento et al. |
| 11,960,518 B2 | 4/2024 | Kappel |
| 11,961,595 B2 | 4/2024 | Madrid et al. |
| 11,967,400 B2 | 4/2024 | Lee et al. |
| 11,967,434 B2 | 4/2024 | Dweik et al. |
| 12,368,503 B2 | 7/2025 | Prasad et al. |
| 2002/0081516 A1 | 6/2002 | Yoon |
| 2003/0014191 A1 | 1/2003 | Agrafiotis et al. |
| 2003/0171939 A1 | 9/2003 | Yagesh et al. |
| 2004/0088118 A1 | 5/2004 | Jensen et al. |
| 2004/0103218 A1 | 5/2004 | Blumrich et al. |
| 2004/0117164 A1 | 6/2004 | Elling et al. |
| 2005/0046584 A1 | 3/2005 | Breed |
| 2005/0065732 A1 | 3/2005 | Tilton et al. |
| 2005/0080502 A1 | 4/2005 | Chernyak et al. |
| 2005/0089923 A9 | 4/2005 | Levinson et al. |
| 2005/0118637 A9 | 6/2005 | Levinson et al. |
| 2005/0148346 A1 | 7/2005 | Maloney et al. |
| 2005/0228511 A1 | 10/2005 | Das et al. |
| 2005/0240355 A1 | 10/2005 | Brown et al. |
| 2005/0278124 A1 | 12/2005 | Duffy et al. |
| 2006/0031027 A1 | 2/2006 | Alman |
| 2006/0040322 A1 | 2/2006 | Archetti et al. |
| 2006/0136186 A1 | 6/2006 | Benight et al. |
| 2006/0167595 A1 | 7/2006 | Breed et al. |
| 2006/0208169 A1 | 9/2006 | Breed et al. |
| 2006/0217864 A1 | 9/2006 | Johnson et al. |
| 2006/0218107 A1 | 9/2006 | Young |
| 2007/0043511 A1 | 2/2007 | Jensen et al. |
| 2007/0061120 A1 | 3/2007 | Akkaram et al. |
| 2007/0085697 A1 | 4/2007 | Breed |
| 2007/0086624 A1 | 4/2007 | Breed et al. |
| 2007/0100565 A1 | 5/2007 | Gosse et al. |
| 2007/0177437 A1 | 8/2007 | Guo |
| 2007/0178561 A1 | 8/2007 | Anderson et al. |
| 2007/0202038 A1 | 8/2007 | Yaghi et al. |
| 2007/0208436 A1 | 9/2007 | Das et al. |
| 2007/0235592 A1 | 10/2007 | Horn et al. |
| 2007/0240242 A1 | 10/2007 | Modiano et al. |
| 2007/0254307 A1 | 11/2007 | Kita |
| 2007/0276610 A1 | 11/2007 | Korenberg |
| 2008/0010027 A1 | 1/2008 | Alman |
| 2008/0104001 A1 | 5/2008 | Kipp |
| 2008/0157940 A1 | 7/2008 | Breed et al. |
| 2008/0170338 A1 | 7/2008 | Guo et al. |
| 2008/0248811 A1 | 10/2008 | Maloney et al. |
| 2009/0089078 A1 | 4/2009 | Bursey |
| 2009/0112489 A1 | 4/2009 | Ghaboussi et al. |
| 2009/0157419 A1 | 6/2009 | Bursey |
| 2009/0182542 A9 | 7/2009 | Hilton et al. |
| 2009/0259607 A1 | 10/2009 | Fukunishi et al. |
| 2009/0259713 A1 | 10/2009 | Blumrich et al. |
| 2010/0010946 A1 | 1/2010 | De Winter et al. |
| 2010/0132549 A1 | 6/2010 | Yaghi et al. |
| 2010/0152953 A1 | 6/2010 | Hamilton |
| 2010/0161531 A1 | 6/2010 | Duffy |
| 2010/0179934 A1 | 7/2010 | Howley et al. |
| 2011/0066414 A1 | 3/2011 | Mills |
| 2011/0161361 A1 | 6/2011 | Csanyi et al. |
| 2011/0166039 A1 | 7/2011 | Tang et al. |
| 2011/0172931 A1 | 7/2011 | Murthy |
| 2011/0257023 A1 | 10/2011 | Gustafsson et al. |
| 2012/0013334 A1 | 1/2012 | Sheiretov et al. |
| 2012/0023948 A1 | 2/2012 | Janson |
| 2012/0116742 A1 | 5/2012 | Prakash et al. |
| 2012/0221501 A1 | 8/2012 | Duffy |
| 2012/0311299 A1 | 12/2012 | Blumrich et al. |
| 2013/0023402 A1 | 1/2013 | Yaghi et al. |
| 2013/0035923 A1 | 2/2013 | Chen et al. |
| 2013/0073221 A1 | 3/2013 | Attinger et al. |
| 2013/0112618 A1 | 5/2013 | Diallo et al. |
| 2013/0138338 A1 | 5/2013 | Behara et al. |
| 2013/0252280 A1 | 9/2013 | Weaver et al. |

(56) References Cited

U.S. PATENT DOCUMENTS

| | | |
|---|---|---|
| 2013/0303387 A1 | 11/2013 | Sander et al. |
| 2014/0100912 A1 | 4/2014 | Bursey |
| 2014/0236548 A1 | 8/2014 | Conduit et al. |
| 2014/0297201 A1 | 10/2014 | Knorr et al. |
| 2014/0297546 A1 | 10/2014 | Birdwell et al. |
| 2015/0120126 A1 | 4/2015 | So et al. |
| 2015/0124999 A1 | 5/2015 | Ren et al. |
| 2015/0134315 A1 | 5/2015 | Sarmiento et al. |
| 2015/0142398 A1 | 5/2015 | Miller, III et al. |
| 2015/0151000 A1 | 6/2015 | Khanna |
| 2015/0177906 A1 | 6/2015 | Yairi et al. |
| 2015/0269313 A1 | 9/2015 | Church |
| 2015/0310162 A1 | 10/2015 | Okuno et al. |
| 2015/0317344 A1 | 11/2015 | Birdwell et al. |
| 2016/0034614 A1 | 2/2016 | Wang et al. |
| 2016/0092660 A1 | 3/2016 | Martinis et al. |
| 2016/0147936 A1 | 5/2016 | Vendruscolo et al. |
| 2016/0188771 A1 | 6/2016 | Michalski |
| 2016/0225370 A1 | 8/2016 | Kannan et al. |
| 2016/0358055 A1 | 12/2016 | Church |
| 2017/0039469 A1 | 2/2017 | Majumdar et al. |
| 2017/0069009 A1 | 3/2017 | Bursey |
| 2017/0115646 A1 | 4/2017 | Chee et al. |
| 2017/0116517 A1 | 4/2017 | Chee et al. |
| 2017/0193200 A1 | 7/2017 | Hsu et al. |
| 2017/0204405 A1 | 7/2017 | Cope et al. |
| 2017/0211206 A1 | 7/2017 | Cope |
| 2017/0300839 A1 | 10/2017 | Bursey |
| 2017/0308856 A1 | 10/2017 | Bursey |
| 2017/0308946 A1 | 10/2017 | Bursey |
| 2018/0018408 A1 | 1/2018 | Matsumura et al. |
| 2018/0071693 A1 | 3/2018 | Diallo et al. |
| 2018/0113974 A1 | 4/2018 | Boday et al. |
| 2018/0121478 A1 | 5/2018 | Walder et al. |
| 2018/0157994 A1 | 6/2018 | Levy |
| 2018/0172694 A1 | 6/2018 | Farokhzad et al. |
| 2018/0181144 A1 | 6/2018 | Steinmann et al. |
| 2018/0196778 A1 | 7/2018 | Glaser et al. |
| 2018/0252087 A1 | 9/2018 | Dinariev et al. |
| 2018/0284815 A1 | 10/2018 | Cui et al. |
| 2018/0373826 A1 | 12/2018 | Klimeck et al. |
| 2019/0018933 A1 | 1/2019 | Oono et al. |
| 2019/0064074 A1 | 2/2019 | Ragan et al. |
| 2019/0064110 A1 | 2/2019 | Timp et al. |
| 2019/0065968 A1 | 2/2019 | Han et al. |
| 2019/0087529 A1 | 3/2019 | Steingrimsson et al. |
| 2019/0121665 A1 | 4/2019 | Clancy et al. |
| 2019/0171928 A1 | 6/2019 | Young |
| 2019/0189250 A1 | 6/2019 | Eiler |
| 2019/0228304 A1 | 7/2019 | Saito |
| 2019/0228843 A1 | 7/2019 | Hou et al. |
| 2019/0236489 A1 | 8/2019 | Koudal et al. |
| 2019/0250586 A1 | 8/2019 | Fenoglietto et al. |
| 2019/0251459 A1 | 8/2019 | Han et al. |
| 2019/0253900 A1 | 8/2019 | Narasimha et al. |
| 2019/0258909 A1 | 8/2019 | Church |
| 2019/0259474 A1 | 8/2019 | Wang et al. |
| 2019/0278880 A1 | 9/2019 | Ma et al. |
| 2019/0286169 A1 | 9/2019 | Cui et al. |
| 2019/0295685 A1 | 9/2019 | Elemento et al. |
| 2019/0303780 A1 | 10/2019 | Spangler et al. |
| 2019/0304568 A1 | 10/2019 | Wei et al. |
| 2019/0311781 A1 | 10/2019 | Stratford et al. |
| 2019/0312779 A1 | 10/2019 | Magzimof et al. |
| 2019/0315497 A1 | 10/2019 | Blomquist |
| 2019/0333604 A1 | 10/2019 | Weaver et al. |
| 2019/0340318 A1 | 11/2019 | Melchionna |
| 2019/0347526 A1 | 11/2019 | Sunkavalli et al. |
| 2020/0003678 A1 | 1/2020 | Wolf et al. |
| 2020/0003682 A1 | 1/2020 | Frenkel et al. |
| 2020/0058376 A1 | 2/2020 | Dean et al. |
| 2020/0072744 A1 | 3/2020 | Al Shehri et al. |
| 2020/0074616 A1 | 3/2020 | Al Shehri et al. |
| 2020/0098449 A1 | 3/2020 | Simonetta et al. |
| 2020/0098450 A1 | 3/2020 | Uesawa |
| 2020/0104465 A1 | 4/2020 | Martin et al. |
| 2020/0118650 A1 | 4/2020 | Yamada et al. |
| 2020/0167439 A1 | 5/2020 | Mailoa et al. |
| 2020/0168291 A1 | 5/2020 | Chowdhury et al. |
| 2020/0168300 A1 | 5/2020 | Goddard, III et al. |
| 2020/0168302 A1 | 5/2020 | Isayev et al. |
| 2020/0176088 A1 | 6/2020 | Kanamarlapudi et al. |
| 2020/0184381 A1 | 6/2020 | Persikov et al. |
| 2020/0201952 A1 | 6/2020 | Kim et al. |
| 2020/0210056 A1 | 7/2020 | Steppan et al. |
| 2020/0210635 A1 | 7/2020 | Washburn et al. |
| 2020/0217777 A1 | 7/2020 | Al Shehri et al. |
| 2020/0224035 A1 | 7/2020 | Knowlton et al. |
| 2020/0227143 A1 | 7/2020 | Katsuki |
| 2020/0234789 A1 | 7/2020 | DeGrado et al. |
| 2020/0243165 A1 | 7/2020 | Katsuki |
| 2020/0243166 A1 | 7/2020 | Tsumura et al. |
| 2020/0251941 A1 | 8/2020 | Kaul |
| 2020/0257933 A1 | 8/2020 | Steingrimsson et al. |
| 2020/0258598 A1 | 8/2020 | Liu et al. |
| 2020/0272702 A1 | 8/2020 | Takeda |
| 2020/0272872 A1 | 8/2020 | Church |
| 2020/0279148 A1 | 9/2020 | Motoki et al. |
| 2020/0283165 A1* | 9/2020 | Krishnamoorthy .... B64D 45/00 |
| 2020/0289421 A1 | 9/2020 | Mitragotri et al. |
| 2020/0294630 A1 | 9/2020 | Miller et al. |
| 2020/0302100 A1 | 9/2020 | Teplinsky et al. |
| 2020/0303042 A1 | 9/2020 | Fuji et al. |
| 2020/0304956 A1 | 9/2020 | Zavesky et al. |
| 2020/0320386 A1 | 10/2020 | Filippov et al. |
| 2020/0320402 A1 | 10/2020 | Yoon et al. |
| 2020/0340970 A1 | 10/2020 | Koseoglu et al. |
| 2020/0342511 A1 | 10/2020 | Bursey |
| 2020/0342953 A1 | 10/2020 | Morrone et al. |
| 2020/0349451 A1 | 11/2020 | Suzuki et al. |
| 2020/0358187 A1 | 11/2020 | Tran et al. |
| 2020/0358522 A1 | 11/2020 | Lee |
| 2020/0372369 A1 | 11/2020 | Gong et al. |
| 2020/0381085 A1 | 12/2020 | Jippo |
| 2020/0387818 A1 | 12/2020 | Chan et al. |
| 2020/0387831 A1 | 12/2020 | Oono et al. |
| 2020/0395099 A1 | 12/2020 | Meyer et al. |
| 2020/0401113 A1 | 12/2020 | Yuan et al. |
| 2020/0410288 A1 | 12/2020 | Capota et al. |
| 2020/0411140 A1 | 12/2020 | Pappas et al. |
| 2021/0008100 A1 | 1/2021 | Davenport Huyer et al. |
| 2021/0012862 A1 | 1/2021 | Plumbley et al. |
| 2021/0027860 A1 | 1/2021 | Zhang et al. |
| 2021/0027862 A1 | 1/2021 | Wei et al. |
| 2021/0027864 A1 | 1/2021 | Plumbley et al. |
| 2021/0045379 A1 | 2/2021 | Grant |
| 2021/0056678 A1 | 2/2021 | Al Shehri et al. |
| 2021/0057050 A1 | 2/2021 | Zavoronkovs et al. |
| 2021/0064801 A1 | 3/2021 | Dweik et al. |
| 2021/0065305 A1 | 3/2021 | Stevenson et al. |
| 2021/0065844 A1 | 3/2021 | Merril |
| 2021/0065853 A1 | 3/2021 | Lyding et al. |
| 2021/0065913 A1 | 3/2021 | Yuan et al. |
| 2021/0072255 A1 | 3/2021 | Farokhzad et al. |
| 2021/0081804 A1 | 3/2021 | Stojevic et al. |
| 2021/0081834 A1 | 3/2021 | Hegde |
| 2021/0082542 A1 | 3/2021 | Bhavnagri |
| 2021/0090690 A1 | 3/2021 | Plumbley et al. |
| 2021/0097211 A1 | 4/2021 | Beck et al. |
| 2021/0098074 A1 | 4/2021 | Wu et al. |
| 2021/0098083 A1 | 4/2021 | Ma et al. |
| 2021/0098084 A1 | 4/2021 | Park et al. |
| 2021/0103822 A1 | 4/2021 | Hegde et al. |
| 2021/0104302 A1 | 4/2021 | Bochevarov et al. |
| 2021/0110307 A1 | 4/2021 | Wakasugi et al. |
| 2021/0110892 A1 | 4/2021 | Kwon et al. |
| 2021/0117869 A1 | 4/2021 | Plumbley et al. |
| 2021/0119158 A1 | 4/2021 | Novotny |
| 2021/0125691 A1 | 4/2021 | Wlodarczyk-Pruszynski et al. |
| 2021/0129106 A1 | 5/2021 | Tabbi et al. |
| 2021/0133590 A1 | 5/2021 | Amroabadi et al. |
| 2021/0133635 A1 | 5/2021 | Hagawa et al. |
| 2021/0150330 A1 | 5/2021 | Sharma et al. |
| 2021/0150402 A1 | 5/2021 | Lienhard et al. |

(56) References Cited

U.S. PATENT DOCUMENTS

| | | |
|---|---|---|
| 2021/0162390 A1 | 6/2021 | Zhong et al. |
| 2021/0166194 A1 | 6/2021 | Ling et al. |
| 2021/0166791 A1 | 6/2021 | Hong et al. |
| 2021/0173117 A1 | 6/2021 | Laugier et al. |
| 2021/0174903 A1 | 6/2021 | Rothberg et al. |
| 2021/0174906 A1 | 6/2021 | Ul Ain et al. |
| 2021/0174908 A1 | 6/2021 | Benjamin et al. |
| 2021/0174909 A1 | 6/2021 | Rothberg et al. |
| 2021/0174910 A1 | 6/2021 | Kwon et al. |
| 2021/0183476 A1 | 6/2021 | Mitarai et al. |
| 2021/0191381 A1 | 6/2021 | Bharadwaj et al. |
| 2021/0193259 A1 | 6/2021 | Bikard et al. |
| 2021/0194768 A1 | 6/2021 | Magzimof et al. |
| 2021/0200915 A1 | 7/2021 | Kumar et al. |
| 2021/0201090 A1 | 7/2021 | Xu et al. |
| 2021/0202047 A1 | 7/2021 | Kang et al. |
| 2021/0210202 A1 | 7/2021 | Awiszus et al. |
| 2021/0216900 A1 | 7/2021 | Higgott et al. |
| 2021/0217498 A1 | 7/2021 | Pae et al. |
| 2021/0224970 A1 | 7/2021 | Roffilli |
| 2021/0225455 A1 | 7/2021 | Chowdhury et al. |
| 2021/0233618 A1 | 7/2021 | Thompson-Colón et al. |
| 2021/0233620 A1 | 7/2021 | Cronin |
| 2021/0233621 A1 | 7/2021 | Zavoronkovs et al. |
| 2021/0241059 A1 | 8/2021 | Church |
| 2021/0241176 A1 | 8/2021 | Yoo et al. |
| 2021/0241858 A1 | 8/2021 | Kurita et al. |
| 2021/0249104 A1 | 8/2021 | Madani et al. |
| 2021/0249105 A1 | 8/2021 | Madani et al. |
| 2021/0249108 A1 | 8/2021 | Lee et al. |
| 2021/0256394 A1 | 8/2021 | Tymoshenko et al. |
| 2021/0264080 A1 | 8/2021 | Ramprasad et al. |
| 2021/0265023 A1 | 8/2021 | Tabbi et al. |
| 2021/0279218 A1 | 9/2021 | Walder et al. |
| 2021/0280277 A1 | 9/2021 | Matsuda et al. |
| 2021/0284695 A1 | 9/2021 | Rocklin et al. |
| 2021/0287137 A1 | 9/2021 | Park et al. |
| 2021/0287762 A1 | 9/2021 | Erez |
| 2021/0287763 A1 | 9/2021 | Sharma |
| 2021/0293381 A1 | 9/2021 | Muthachikavil et al. |
| 2021/0293801 A1 | 9/2021 | Farokhzad et al. |
| 2021/0294301 A1 | 9/2021 | Flitsch et al. |
| 2021/0295167 A1 | 9/2021 | Hill |
| 2021/0303290 A1 | 9/2021 | Schmit et al. |
| 2021/0303757 A1 | 9/2021 | Pandey et al. |
| 2021/0303762 A1 | 9/2021 | Ristoski et al. |
| 2021/0303971 A1 | 9/2021 | Ranade et al. |
| 2021/0304847 A1 | 9/2021 | Senior et al. |
| 2021/0304851 A1 | 9/2021 | Schlifke |
| 2021/0304852 A1 | 9/2021 | Ristoski et al. |
| 2021/0304853 A1 | 9/2021 | Branson et al. |
| 2021/0304854 A1 | 9/2021 | Lee et al. |
| 2021/0311039 A1 | 10/2021 | Farokhzad et al. |
| 2021/0311040 A1 | 10/2021 | Farokhzad et al. |
| 2021/0311064 A1 | 10/2021 | Farokhzad et al. |
| 2021/0313008 A1 | 10/2021 | Senior et al. |
| 2021/0313015 A1 | 10/2021 | Sukegawa et al. |
| 2021/0318321 A1 | 10/2021 | Farokhzad et al. |
| 2021/0318670 A1 | 10/2021 | Cunningham et al. |
| 2021/0319098 A1 | 10/2021 | Pogorelik et al. |
| 2021/0319146 A1 | 10/2021 | Reinhart et al. |
| 2021/0319336 A1 | 10/2021 | Yano |
| 2021/0319847 A1 | 10/2021 | Min et al. |
| 2021/0326755 A1 | 10/2021 | Hashimoto et al. |
| 2021/0334655 A1 | 10/2021 | Obika et al. |
| 2021/0341625 A1 | 11/2021 | Gupta |
| 2021/0342508 A1 | 11/2021 | Arroyave et al. |
| 2021/0345939 A1 | 11/2021 | Jumbe et al. |
| 2021/0349041 A1 | 11/2021 | Gettemy et al. |
| 2021/0350312 A1 | 11/2021 | Swift et al. |
| 2021/0357555 A1 | 11/2021 | Liu et al. |
| 2021/0358205 A1 | 11/2021 | Laugier et al. |
| 2021/0358564 A1 | 11/2021 | Feinberg et al. |
| 2021/0363183 A1 | 11/2021 | Das et al. |
| 2021/0366580 A1 | 11/2021 | Das et al. |
| 2021/0366581 A1 | 11/2021 | Lee et al. |
| 2021/0372561 A1 | 12/2021 | Swift et al. |
| 2021/0372994 A1 | 12/2021 | Metzger et al. |
| 2021/0374295 A1 | 12/2021 | Beck et al. |
| 2021/0374551 A1 | 12/2021 | Vijil et al. |
| 2021/0375402 A1 | 12/2021 | Jin et al. |
| 2021/0375403 A1 | 12/2021 | Onishi et al. |
| 2021/0381992 A1 | 12/2021 | Aguiar |
| 2021/0382184 A1 | 12/2021 | Cui et al. |
| 2021/0383898 A1 | 12/2021 | Kuznetsov et al. |
| 2021/0385865 A1 | 12/2021 | Mueck et al. |
| 2021/0391037 A1 | 12/2021 | Lotrich et al. |
| 2021/0391038 A1 | 12/2021 | Sukegawa et al. |
| 2021/0397978 A1 | 12/2021 | Pae et al. |
| 2021/0398018 A1 | 12/2021 | Dao et al. |
| 2021/0398621 A1 | 12/2021 | Stojevic et al. |
| 2021/0407625 A1 | 12/2021 | Senior et al. |
| 2021/0409335 A1 | 12/2021 | Zhu et al. |
| 2022/0004887 A1 | 1/2022 | Spratt et al. |
| 2022/0005548 A1 | 1/2022 | Redei et al. |
| 2022/0009966 A1 | 1/2022 | Das et al. |
| 2022/0013197 A1 | 1/2022 | Walsh et al. |
| 2022/0014946 A1 | 1/2022 | Merwaday et al. |
| 2022/0014963 A1 | 1/2022 | Yeh et al. |
| 2022/0020454 A1 | 1/2022 | Pae et al. |
| 2022/0027374 A1 | 1/2022 | Brown et al. |
| 2022/0027759 A1 | 1/2022 | Tabbi et al. |
| 2022/0028499 A1 | 1/2022 | Tsumura et al. |
| 2022/0032215 A1 | 2/2022 | Blackman et al. |
| 2022/0032256 A1 | 2/2022 | Lackey et al. |
| 2022/0038554 A1 | 2/2022 | Merwaday et al. |
| 2022/0038902 A1 | 2/2022 | Mueck |
| 2022/0044767 A1 | 2/2022 | Rong et al. |
| 2022/0044769 A1 | 2/2022 | Ramprasad et al. |
| 2022/0045425 A1 | 2/2022 | Tran et al. |
| 2022/0051141 A1 | 2/2022 | Kabir et al. |
| 2022/0051759 A1 | 2/2022 | Brereton et al. |
| 2022/0052753 A1 | 2/2022 | Speidel et al. |
| 2022/0055997 A1 | 2/2022 | Akabayov |
| 2022/0057519 A1 | 2/2022 | Goldstein et al. |
| 2022/0058865 A1 | 2/2022 | Beltrand |
| 2022/0059196 A1 | 2/2022 | Lee et al. |
| 2022/0063986 A1 | 3/2022 | Suresh et al. |
| 2022/0064634 A1 | 3/2022 | Rickerby et al. |
| 2022/0067247 A1 | 3/2022 | Suresh et al. |
| 2022/0067249 A1 | 3/2022 | Steingrimsson |
| 2022/0068162 A1 | 3/2022 | Thöne et al. |
| 2022/0068440 A1 | 3/2022 | Mrziglod et al. |
| 2022/0068441 A1 | 3/2022 | Tsumura et al. |
| 2022/0068442 A1 | 3/2022 | Yang et al. |
| 2022/0072593 A1 | 3/2022 | Fujita et al. |
| 2022/0076137 A1 | 3/2022 | Hoffman et al. |
| 2022/0081472 A1 | 3/2022 | Greving et al. |
| 2022/0083700 A1 | 3/2022 | Takagi et al. |
| 2022/0084140 A1 | 3/2022 | Daczko et al. |
| 2022/0084627 A1 | 3/2022 | Roy et al. |
| 2022/0086218 A1 | 3/2022 | Sabella et al. |
| 2022/0091571 A1 | 3/2022 | Ivanov et al. |
| 2022/0100932 A1 | 3/2022 | Nakatsuji et al. |
| 2022/0101276 A1 | 3/2022 | Banatao et al. |
| 2022/0101277 A1 | 3/2022 | Banatao et al. |
| 2022/0101954 A1 | 3/2022 | Wang et al. |
| 2022/0101972 A1 | 3/2022 | Bajpai et al. |
| 2022/0103922 A1 | 3/2022 | Jumbe et al. |
| 2022/0108047 A1 | 4/2022 | Cheng et al. |
| 2022/0108175 A1 | 4/2022 | Lyske et al. |
| 2022/0108765 A1 | 4/2022 | Teshima et al. |
| 2022/0119318 A1 | 4/2022 | Kayello et al. |
| 2022/0121939 A1 | 4/2022 | Evans et al. |
| 2022/0122697 A1 | 4/2022 | Liu et al. |
| 2022/0129600 A1 | 4/2022 | Roberts et al. |
| 2022/0130033 A1 | 4/2022 | Rashidi et al. |
| 2022/0130490 A1 | 4/2022 | Min et al. |
| 2022/0130494 A1 | 4/2022 | Woodbury et al. |
| 2022/0130495 A1 | 4/2022 | Li et al. |
| 2022/0130496 A1 | 4/2022 | Li et al. |
| 2022/0139504 A1 | 5/2022 | Wiltschko et al. |
| 2022/0156440 A1 | 5/2022 | Masuko et al. |
| 2022/0157193 A1 | 5/2022 | Winter et al. |

(56) References Cited

U.S. PATENT DOCUMENTS

| | | |
|---|---|---|
| 2022/0157403 A1 | 5/2022 | Mason et al. |
| 2022/0157407 A1 | 5/2022 | Akiyama et al. |
| 2022/0164501 A1 | 5/2022 | Nosanow et al. |
| 2022/0164627 A1 | 5/2022 | Friedensohn et al. |
| 2022/0164685 A1 | 5/2022 | Shioga |
| 2022/0165359 A1 | 5/2022 | Lee et al. |
| 2022/0165364 A1 | 5/2022 | Qiao et al. |
| 2022/0165366 A1 | 5/2022 | Zubarev et al. |
| 2022/0165367 A1 | 5/2022 | Priyakumar et al. |
| 2022/0169865 A1 | 6/2022 | Short et al. |
| 2022/0170900 A1 | 6/2022 | Choi et al. |
| 2022/0171353 A1 | 6/2022 | Ramsundar |
| 2022/0172803 A1 | 6/2022 | Fuchiwaki et al. |
| 2022/0179400 A1 | 6/2022 | Deodhar et al. |
| 2022/0180975 A1 | 6/2022 | Regev et al. |
| 2022/0180977 A1 | 6/2022 | Kim |
| 2022/0180978 A1 | 6/2022 | Burnham et al. |
| 2022/0180991 A1 | 6/2022 | Peters |
| 2022/0189578 A1 | 6/2022 | Takeda |
| 2022/0190243 A1 | 6/2022 | Bagheri et al. |
| 2022/0196620 A1 | 6/2022 | Godin et al. |
| 2022/0198106 A1 | 6/2022 | Montoya et al. |
| 2022/0198280 A1 | 6/2022 | Yoon et al. |
| 2022/0198286 A1 | 6/2022 | Prat et al. |
| 2022/0198330 A1 | 6/2022 | Zhang et al. |
| 2022/0207218 A1 | 6/2022 | Lu et al. |
| 2022/0207370 A1 | 6/2022 | Motoki |
| 2022/0207393 A1 | 6/2022 | Umezawa et al. |
| 2022/0208311 A1 | 6/2022 | Kim |
| 2022/0208540 A1 | 6/2022 | Behsaz et al. |
| 2022/0210626 A1 | 6/2022 | Agostinelli et al. |
| 2022/0214810 A1 | 7/2022 | Adams et al. |
| 2022/0215233 A1 | 7/2022 | Buehler et al. |
| 2022/0223234 A1 | 7/2022 | Asahara et al. |
| 2022/0226922 A1 | 7/2022 | Albrecht et al. |
| 2022/0230712 A1 | 7/2022 | Sheberla et al. |
| 2022/0230713 A1 | 7/2022 | Maragakis et al. |
| 2022/0238179 A1 | 7/2022 | Sarmiento et al. |
| 2022/0238189 A1 | 7/2022 | Kim et al. |
| 2022/0238190 A1 | 7/2022 | Spagnoli |
| 2022/0238191 A1 | 7/2022 | Fan et al. |
| 2022/0242597 A1 | 8/2022 | Mukae |
| 2022/0245188 A1 | 8/2022 | Kappel |
| 2022/0246239 A1 | 8/2022 | Cho et al. |
| 2022/0246244 A1 | 8/2022 | Kappel |
| 2022/0246252 A1 | 8/2022 | Stache et al. |
| 2022/0253669 A1 | 8/2022 | Teramoto et al. |
| 2022/0254456 A1 | 8/2022 | Lingenfelser et al. |
| 2022/0261510 A1 | 8/2022 | Takemoto et al. |
| 2022/0262463 A1 | 8/2022 | Thompson-Colón |
| 2022/0270705 A1 | 8/2022 | Vijil et al. |
| 2022/0270706 A1 | 8/2022 | Vijil et al. |
| 2022/0270711 A1 | 8/2022 | Feala et al. |
| 2022/0270713 A1 | 8/2022 | Spagnoli |
| 2022/0270714 A1 | 8/2022 | Okamoto et al. |
| 2022/0272084 A1* | 8/2022 | Hyatt ..................... H04W 4/70 |
| 2022/0275714 A1 | 9/2022 | Madasu et al. |
| 2022/0277224 A1 | 9/2022 | Akiyama et al. |
| 2022/0277815 A1 | 9/2022 | Hosoumi et al. |
| 2022/0281619 A1 | 9/2022 | Blomquist |
| 2022/0284990 A1 | 9/2022 | Chi et al. |
| 2022/0284991 A1 | 9/2022 | Tabbi et al. |
| 2022/0291405 A1 | 9/2022 | Silveira de Albuquerque Martins et al. |
| 2022/0292229 A1 | 9/2022 | Aonuma et al. |
| 2022/0292762 A1 | 9/2022 | Boubekeur et al. |
| 2022/0293216 A1 | 9/2022 | Park et al. |
| 2022/0293223 A1 | 9/2022 | Ren et al. |
| 2022/0293225 A1 | 9/2022 | Park et al. |
| 2022/0301662 A1 | 9/2022 | Yamano et al. |
| 2022/0302776 A1 | 9/2022 | Kaul |
| 2022/0306476 A1 | 9/2022 | Cao et al. |
| 2022/0307997 A1 | 9/2022 | Meijer et al. |
| 2022/0310211 A1 | 9/2022 | Jippo et al. |
| 2022/0310213 A1 | 9/2022 | Noh et al. |
| 2022/0318658 A1 | 10/2022 | Ivankin et al. |
| 2022/0319634 A1 | 10/2022 | M. Kleber |
| 2022/0323924 A1 | 10/2022 | Lackey et al. |
| 2022/0323935 A1 | 10/2022 | Fairen-Jimenez et al. |
| 2022/0328141 A1 | 10/2022 | Gedeck et al. |
| 2022/0332350 A1 | 10/2022 | Jha et al. |
| 2022/0335281 A1 | 10/2022 | Spieker et al. |
| 2022/0336056 A1 | 10/2022 | Hamp et al. |
| 2022/0336057 A1 | 10/2022 | Hamp et al. |
| 2022/0348903 A1 | 11/2022 | Ranganathan et al. |
| 2022/0351053 A1 | 11/2022 | Norvaisas et al. |
| 2022/0351056 A1 | 11/2022 | de Bayser et al. |
| 2022/0351808 A1 | 11/2022 | Clyde et al. |
| 2022/0351809 A1 | 11/2022 | Kim et al. |
| 2022/0358438 A1 | 11/2022 | Asahara et al. |
| 2022/0359045 A1 | 11/2022 | Manica et al. |
| 2022/0359046 A1 | 11/2022 | Arneault et al. |
| 2022/0359047 A1 | 11/2022 | Kanazawa et al. |
| 2022/0365096 A1 | 11/2022 | Farokhzad et al. |
| 2022/0366232 A1 | 11/2022 | Vija et al. |
| 2022/0372068 A1 | 11/2022 | Kim et al. |
| 2022/0372643 A1 | 11/2022 | Wang et al. |
| 2022/0374334 A1 | 11/2022 | Brown et al. |
| 2022/0374336 A1 | 11/2022 | Brown et al. |
| 2022/0374337 A1 | 11/2022 | Brown |
| 2022/0374338 A1 | 11/2022 | Brown et al. |
| 2022/0374339 A1 | 11/2022 | Brown |
| 2022/0374344 A1 | 11/2022 | Brown |
| 2022/0374721 A1 | 11/2022 | Agarwal et al. |
| 2022/0375538 A1 | 11/2022 | Das et al. |
| 2022/0382938 A1 | 12/2022 | Ito et al. |
| 2022/0383064 A1 | 12/2022 | Li et al. |
| 2022/0383989 A1 | 12/2022 | Jonas |
| 2022/0383990 A1 | 12/2022 | Zhang |
| 2022/0383992 A1 | 12/2022 | Triendl et al. |
| 2022/0383993 A1 | 12/2022 | Yoo et al. |
| 2022/0383994 A1 | 12/2022 | Rabideau |
| 2022/0384058 A1 | 12/2022 | Lee et al. |
| 2022/0389511 A1 | 12/2022 | Kelley |
| 2022/0391699 A1 | 12/2022 | Hanaoka |
| 2022/0392580 A1 | 12/2022 | Elemento et al. |
| 2022/0392583 A1 | 12/2022 | Godin et al. |
| 2022/0392584 A1 | 12/2022 | Hanaoka |
| 2022/0392585 A1 | 12/2022 | Zhang et al. |
| 2022/0397886 A1 | 12/2022 | Hong et al. |
| 2022/0397917 A1 | 12/2022 | Arksey et al. |
| 2022/0398806 A1 | 12/2022 | Arksey et al. |
| 2022/0399082 A1 | 12/2022 | Lee et al. |
| 2022/0399083 A1 | 12/2022 | Ayral et al. |
| 2022/0399085 A1 | 12/2022 | Bowden, Jr. et al. |
| 2022/0399936 A1 | 12/2022 | Arksey et al. |
| 2022/0404361 A1 | 12/2022 | Sabry et al. |
| 2022/0405563 A1 | 12/2022 | Noh et al. |
| 2022/0405654 A1 | 12/2022 | Komikawa et al. |
| 2022/0406403 A1 | 12/2022 | Singh et al. |
| 2022/0406404 A1 | 12/2022 | Kuznetsov et al. |
| 2022/0406412 A1 | 12/2022 | Segler et al. |
| 2022/0406416 A1 | 12/2022 | Muthiah Ravinson et al. |
| 2022/0406417 A1 | 12/2022 | Kaneko et al. |
| 2022/0407001 A1 | 12/2022 | Takeuchi et al. |
| 2022/0414499 A1 | 12/2022 | Hosoumi et al. |
| 2022/0415433 A1 | 12/2022 | Xu et al. |
| 2022/0415446 A1 | 12/2022 | Lee et al. |
| 2022/0415450 A1 | 12/2022 | Nguyen et al. |
| 2022/0415452 A1 | 12/2022 | Ye et al. |
| 2022/0415453 A1 | 12/2022 | Ronneberger et al. |
| 2023/0004142 A1 | 1/2023 | Cetinkaya |
| 2023/0005128 A1 | 1/2023 | Niederhoefer et al. |
| 2023/0005572 A1 | 1/2023 | Chen et al. |
| 2023/0009725 A1 | 1/2023 | McDaniel et al. |
| 2023/0018216 A1 | 1/2023 | Lu |
| 2023/0018537 A1 | 1/2023 | Brandsma et al. |
| 2023/0019202 A1 | 1/2023 | Chen et al. |
| 2023/0023641 A1 | 1/2023 | Rosenfeld et al. |
| 2023/0027514 A1 | 1/2023 | Ma et al. |
| 2023/0027989 A1 | 1/2023 | Takakuwa et al. |
| 2023/0028046 A1 | 1/2023 | Xing et al. |
| 2023/0029474 A1 | 2/2023 | Wade et al. |
| 2023/0032092 A1 | 2/2023 | Teplinsky et al. |

(56) References Cited

U.S. PATENT DOCUMENTS

| | | |
|---|---|---|
| 2023/0034425 A1 | 2/2023 | Laniado et al. |
| 2023/0037091 A1 | 2/2023 | Jandhyala et al. |
| 2023/0037388 A1 | 2/2023 | Sakhinana et al. |
| 2023/0038256 A1 | 2/2023 | Tal et al. |
| 2023/0040576 A1 | 2/2023 | Laniado et al. |
| 2023/0040805 A1 | 2/2023 | Mitragotri et al. |
| 2023/0041431 A1 | 2/2023 | Poon et al. |
| 2023/0043363 A1 | 2/2023 | Neumann Barros Ferreira et al. |
| 2023/0043540 A1 | 2/2023 | Yu et al. |
| 2023/0044622 A1 | 2/2023 | Grant |
| 2023/0045690 A1 | 2/2023 | Sakhinana et al. |
| 2023/0049157 A1 | 2/2023 | Sawlani et al. |
| 2023/0050156 A1 | 2/2023 | Yu et al. |
| 2023/0050627 A1 | 2/2023 | Sattarov et al. |
| 2023/0051669 A1 | 2/2023 | Johri et al. |
| 2023/0052677 A1 | 2/2023 | Eser et al. |
| 2023/0054552 A1 | 2/2023 | Yang et al. |
| 2023/0054582 A1 | 2/2023 | Kishimoto et al. |
| 2023/0057311 A1* | 2/2023 | Moeykens ............. G06N 20/00 |
| 2023/0061483 A1 | 3/2023 | Alexander et al. |
| 2023/0063171 A1 | 3/2023 | Kwon et al. |
| 2023/0073351 A1 | 3/2023 | Akiva et al. |
| 2023/0075100 A1 | 3/2023 | Zavoronkovs et al. |
| 2023/0076608 A1 | 3/2023 | Kajino |
| 2023/0076840 A1 | 3/2023 | Farokhzad et al. |
| 2023/0078275 A1 | 3/2023 | Kubis et al. |
| 2023/0081412 A1 | 3/2023 | Fu et al. |
| 2023/0081583 A1 | 3/2023 | Kanazawa et al. |
| 2023/0088979 A1 | 3/2023 | Neogi et al. |
| 2023/0093875 A1 | 3/2023 | Mitragotri et al. |
| 2023/0095631 A1 | 3/2023 | Ganeshan et al. |
| 2023/0095685 A1 | 3/2023 | Greving et al. |
| 2023/0098398 A1 | 3/2023 | Xu et al. |
| 2023/0100584 A1 | 3/2023 | Diedam et al. |
| 2023/0103487 A1 | 4/2023 | Byrnes et al. |
| 2023/0104058 A1 | 4/2023 | Hopfmueller et al. |
| 2023/0105422 A1 | 4/2023 | Pickles et al. |
| 2023/0105998 A1 | 4/2023 | Yakovenko et al. |
| 2023/0111521 A1 | 4/2023 | Singh et al. |
| 2023/0113207 A1 | 4/2023 | Woo et al. |
| 2023/0115171 A1 | 4/2023 | Singh et al. |
| 2023/0115719 A1 | 4/2023 | Sakhinana et al. |
| 2023/0115984 A1 | 4/2023 | Chen et al. |
| 2023/0116680 A1 | 4/2023 | Sakhinana et al. |
| 2023/0117325 A1 | 4/2023 | Osakabe et al. |
| 2023/0118842 A1 | 4/2023 | Jafri et al. |
| 2023/0122101 A1 | 4/2023 | Kim et al. |
| 2023/0129485 A1 | 4/2023 | Pereyaslavets et al. |
| 2023/0130619 A1 | 4/2023 | Ma et al. |
| 2023/0131234 A1 | 4/2023 | Jastrzebski et al. |
| 2023/0134595 A1 | 5/2023 | Sakhinana et al. |
| 2023/0135041 A1 | 5/2023 | Aykol et al. |
| 2023/0137741 A1 | 5/2023 | Kassis et al. |
| 2023/0139766 A1 | 5/2023 | Kang et al. |
| 2023/0141266 A1 | 5/2023 | Alberts |
| 2023/0143768 A1 | 5/2023 | Asahara et al. |
| 2023/0145099 A1 | 5/2023 | Funakawa |
| 2023/0152823 A1* | 5/2023 | Wiegman ................. G08G 5/34 |
| 2023/0153491 A1 | 5/2023 | Kanazawa et al. |
| 2023/0153976 A1 | 5/2023 | Kiyokane et al. |
| 2023/0154571 A1 | 5/2023 | Terreux et al. |
| 2023/0154573 A1 | 5/2023 | Roy et al. |
| 2023/0158469 A1 | 5/2023 | Lackey et al. |
| 2023/0160019 A1 | 5/2023 | Armstrong et al. |
| 2023/0160097 A1 | 5/2023 | Qi et al. |
| 2023/0161844 A1 | 5/2023 | Lee et al. |
| 2023/0161996 A1 | 5/2023 | Bepler |
| 2023/0162093 A1 | 5/2023 | Dupont De Dinechin |
| 2023/0169751 A1 | 6/2023 | Geurts |
| 2023/0170053 A1 | 6/2023 | Gharakhanyan et al. |
| 2023/0170054 A1 | 6/2023 | Kubis et al. |
| 2023/0170055 A1 | 6/2023 | Qi et al. |
| 2023/0170056 A1 | 6/2023 | Yang et al. |
| 2023/0170059 A1 | 6/2023 | Gadhiya et al. |
| 2023/0170061 A1 | 6/2023 | Tanaka et al. |
| 2023/0175062 A1 | 6/2023 | Lackey et al. |
| 2023/0176058 A1 | 6/2023 | Warsinske et al. |
| 2023/0177327 A1 | 6/2023 | Pillai et al. |
| 2023/0177968 A1 | 6/2023 | Arksey et al. |
| 2023/0178185 A1 | 6/2023 | Gormley et al. |
| 2023/0178186 A1 | 6/2023 | Amimeur et al. |
| 2023/0183867 A1 | 6/2023 | Viswanathan et al. |
| 2023/0186057 A1 | 6/2023 | Musaelian et al. |
| 2023/0186615 A1 | 6/2023 | Cook et al. |
| 2023/0187016 A1 | 6/2023 | Araya et al. |
| 2023/0187027 A1 | 6/2023 | Liu et al. |
| 2023/0187029 A1 | 6/2023 | Jandhyala et al. |
| 2023/0196075 A1 | 6/2023 | Ishitani |
| 2023/0196132 A1 | 6/2023 | Horowitz et al. |
| 2023/0196629 A1 | 6/2023 | Teskey |
| 2023/0197209 A1 | 6/2023 | Yu et al. |
| 2023/0205175 A1 | 6/2023 | Zhao et al. |
| 2023/0207066 A1 | 6/2023 | Lee et al. |
| 2023/0213504 A1 | 7/2023 | Farokhzad et al. |
| 2023/0215278 A1* | 7/2023 | Kanagarajan ............ G08G 5/34 340/963 |
| 2023/0217956 A1 | 7/2023 | Navi et al. |
| 2023/0217957 A1 | 7/2023 | Navi et al. |
| 2023/0223101 A1 | 7/2023 | Navi et al. |
| 2023/0223112 A1 | 7/2023 | Sun et al. |
| 2023/0223113 A1 | 7/2023 | Ragan et al. |
| 2023/0230662 A1 | 7/2023 | Sarshogh et al. |
| 2023/0234989 A1 | 7/2023 | Liszka et al. |
| 2023/0237339 A1 | 7/2023 | Hummelshøj |
| 2023/0237365 A1 | 7/2023 | Hummelshøj |
| 2023/0238083 A1 | 7/2023 | Liu et al. |
| 2023/0238084 A1 | 7/2023 | Tsumura et al. |
| 2023/0238085 A1 | 7/2023 | Jang et al. |
| 2023/0244833 A1 | 8/2023 | Mechin et al. |
| 2023/0245003 A1 | 8/2023 | Hummelshøj |
| 2023/0245110 A1 | 8/2023 | Arneault et al. |
| 2023/0245725 A1 | 8/2023 | Rousseau et al. |
| 2023/0245726 A1 | 8/2023 | Fäcke |
| 2023/0245727 A1 | 8/2023 | He et al. |
| 2023/0251226 A1 | 8/2023 | Matsui et al. |
| 2023/0252355 A1 | 8/2023 | Tao et al. |
| 2023/0253076 A1 | 8/2023 | Safiulin et al. |
| 2023/0258838 A1 | 8/2023 | Roy et al. |
| 2023/0260602 A1 | 8/2023 | Sankaranarayanan et al. |
| 2023/0260603 A1 | 8/2023 | Montoya et al. |
| 2023/0268035 A1 | 8/2023 | Kim et al. |
| 2023/0268987 A1 | 8/2023 | Moyal et al. |
| 2023/0274789 A1 | 8/2023 | Li et al. |
| 2023/0274797 A1 | 8/2023 | Bian et al. |
| 2023/0274803 A1 | 8/2023 | Ueki et al. |
| 2023/0281465 A1 | 9/2023 | Feinberg et al. |
| 2023/0281474 A1 | 9/2023 | Steinmetz et al. |
| 2023/0282311 A1 | 9/2023 | Behsaz et al. |
| 2023/0284178 A1 | 9/2023 | Parker et al. |
| 2023/0285968 A1 | 9/2023 | Bentwich et al. |
| 2023/0288907 A1 | 9/2023 | Coffman et al. |
| 2023/0290114 A1 | 9/2023 | Prat et al. |
| 2023/0290434 A1 | 9/2023 | Castro et al. |
| 2023/0290435 A1 | 9/2023 | Madhusudhanan et al. |
| 2023/0290444 A1 | 9/2023 | Bronstein et al. |
| 2023/0290445 A1 | 9/2023 | Choi et al. |
| 2023/0292075 A1 | 9/2023 | Walther et al. |
| 2023/0297853 A1 | 9/2023 | Bucher et al. |
| 2023/0298706 A1 | 9/2023 | Vissers et al. |
| 2023/0302043 A1 | 9/2023 | Huyer et al. |
| 2023/0304391 A1 | 9/2023 | Sheng et al. |
| 2023/0315803 A1 | 10/2023 | Babbush |
| 2023/0315924 A1 | 10/2023 | Hummelshøj et al. |
| 2023/0317202 A1 | 10/2023 | Stojevic et al. |
| 2023/0321706 A1 | 10/2023 | Ojima et al. |
| 2023/0323503 A1 | 10/2023 | Ojima et al. |
| 2023/0325687 A1 | 10/2023 | Pabrinkis et al. |
| 2023/0325751 A1 | 10/2023 | Clavero et al. |
| 2023/0326543 A1 | 10/2023 | Ferguson et al. |
| 2023/0331723 A1 | 10/2023 | Polykovskiy et al. |
| 2023/0331990 A1 | 10/2023 | Knowlton et al. |
| 2023/0332967 A1 | 10/2023 | Earthman et al. |
| 2023/0333127 A1 | 10/2023 | Lenhert et al. |
| 2023/0334380 A1 | 10/2023 | Ivankin et al. |

(56)        References Cited

U.S. PATENT DOCUMENTS

| 2023/0334991 A1* | 10/2023 | Shapiro ................... G10L 15/22 |
| 2023/0335226 A1 | 10/2023 | Yarimizu et al. |
| 2023/0335229 A1 | 10/2023 | Li et al. |
| 2023/0335231 A1 | 10/2023 | Abdallah et al. |
| 2023/0339185 A1 | 10/2023 | Huang |
| 2023/0342525 A1 | 10/2023 | Yavas et al. |
| 2023/0347512 A1 | 11/2023 | Kwon |
| 2023/0350380 A1 | 11/2023 | Coffman et al. |
| 2023/0350395 A1 | 11/2023 | Winkler et al. |
| 2023/0350396 A1 | 11/2023 | Rudolph et al. |
| 2023/0352118 A1 | 11/2023 | Seif et al. |
| 2023/0352122 A1 | 11/2023 | Mawlod et al. |
| 2023/0352123 A1 | 11/2023 | Atkinson et al. |
| 2023/0359155 A1 | 11/2023 | Schockaert et al. |
| 2023/0359929 A1 | 11/2023 | Shmilovich et al. |
| 2023/0360736 A1 | 11/2023 | Stober et al. |
| 2023/0360739 A1 | 11/2023 | Kim et al. |
| 2023/0360743 A1 | 11/2023 | Gedeck et al. |
| 2023/0360744 A1 | 11/2023 | Sala et al. |
| 2023/0366863 A1 | 11/2023 | Tate et al. |
| 2023/0376646 A1 | 11/2023 | Krompiec |
| 2023/0376648 A1 | 11/2023 | Khan et al. |
| 2023/0377681 A1 | 11/2023 | Mukhopadhyay et al. |
| 2023/0377682 A1 | 11/2023 | Min et al. |
| 2023/0377690 A1 | 11/2023 | Anand et al. |
| 2023/0377693 A1 | 11/2023 | Krompiec |
| 2023/0385666 A1 | 11/2023 | Ghosh et al. |
| 2023/0385681 A1 | 11/2023 | Montanaro et al. |
| 2023/0386604 A1 | 11/2023 | Park et al. |
| 2023/0386616 A1 | 11/2023 | Kondo et al. |
| 2023/0386617 A1 | 11/2023 | Hagawa et al. |
| 2023/0386618 A1 | 11/2023 | Thomas et al. |
| 2023/0390725 A1 | 12/2023 | Winkler et al. |
| 2023/0393543 A1 | 12/2023 | Nixon et al. |
| 2023/0393564 A1 | 12/2023 | Nixon et al. |
| 2023/0394045 A1 | 12/2023 | Nixon et al. |
| 2023/0394196 A1 | 12/2023 | Liu et al. |
| 2023/0394283 A1 | 12/2023 | Pang et al. |
| 2023/0395186 A1 | 12/2023 | Kohl et al. |
| 2023/0395201 A1 | 12/2023 | Pappas et al. |
| 2023/0395202 A1 | 12/2023 | Das et al. |
| 2023/0401351 A1 | 12/2023 | Galchenko et al. |
| 2023/0401361 A1 | 12/2023 | Teskey et al. |
| 2023/0401430 A1 | 12/2023 | Zheng et al. |
| 2023/0402125 A1 | 12/2023 | Jin et al. |
| 2023/0402126 A1 | 12/2023 | Cheng et al. |
| 2023/0402127 A1 | 12/2023 | Altman et al. |
| 2023/0402134 A1 | 12/2023 | Bhattacharya et al. |
| 2023/0402135 A1 | 12/2023 | Wu et al. |
| 2023/0402136 A1 | 12/2023 | Zheng et al. |
| 2023/0402137 A1 | 12/2023 | Smith et al. |
| 2023/0406713 A1 | 12/2023 | Li et al. |
| 2023/0409015 A1 | 12/2023 | Winkler et al. |
| 2023/0409904 A1 | 12/2023 | Birru et al. |
| 2023/0410940 A1 | 12/2023 | Fonstein et al. |
| 2023/0410950 A1 | 12/2023 | Godin et al. |
| 2023/0410953 A1 | 12/2023 | Zhang et al. |
| 2023/0410970 A1 | 12/2023 | Bugay et al. |
| 2023/0411222 A1 | 12/2023 | Lee et al. |
| 2023/0416726 A1 | 12/2023 | Baker et al. |
| 2023/0417919 A1 | 12/2023 | Goldstein et al. |
| 2023/0418995 A1 | 12/2023 | Li et al. |
| 2023/0419086 A1 | 12/2023 | Pocajt et al. |
| 2023/0420069 A1 | 12/2023 | Stojevic et al. |
| 2023/0420085 A1 | 12/2023 | Mukherjee et al. |
| 2023/0420193 A1 | 12/2023 | Bevan et al. |
| 2023/0420729 A1 | 12/2023 | Yoon et al. |
| 2023/0420757 A1 | 12/2023 | Garapati et al. |
| 2023/0421246 A1 | 12/2023 | Mukae |
| 2024/0005147 A1 | 1/2024 | Hoseinabadi et al. |
| 2024/0005179 A1 | 1/2024 | Yu et al. |
| 2024/0006017 A1 | 1/2024 | Wang et al. |
| 2024/0006018 A1 | 1/2024 | Knowles et al. |
| 2024/0012399 A1 | 1/2024 | Stewart et al. |
| 2024/0012967 A1 | 1/2024 | Jinguu et al. |
| 2024/0013866 A1 | 1/2024 | Lee et al. |
| 2024/0013868 A1 | 1/2024 | Bhavnagri |
| 2024/0013870 A1 | 1/2024 | Jinguu et al. |
| 2024/0019600 A1 | 1/2024 | Holmes et al. |
| 2024/0019845 A1 | 1/2024 | Yoo et al. |
| 2024/0020433 A1 | 1/2024 | Cordes et al. |
| 2024/0020437 A1 | 1/2024 | Kubis et al. |
| 2024/0020968 A1 | 1/2024 | Haskin et al. |
| 2024/0021275 A1 | 1/2024 | Wiltschko et al. |
| 2024/0021276 A1 | 1/2024 | Jiao et al. |
| 2024/0021277 A1 | 1/2024 | Zaw et al. |
| 2024/0024839 A1 | 1/2024 | Winkler et al. |
| 2024/0028882 A1 | 1/2024 | Hopkins et al. |
| 2024/0028889 A1 | 1/2024 | Mudassir et al. |
| 2024/0028928 A1 | 1/2024 | Kudva et al. |
| 2024/0029833 A1 | 1/2024 | Thiry |
| 2024/0029834 A1 | 1/2024 | Nichita |
| 2024/0029836 A1 | 1/2024 | Nie et al. |
| 2024/0033801 A1 | 2/2024 | Kobayashi et al. |
| 2024/0034636 A1 | 2/2024 | Roche et al. |
| 2024/0036034 A1 | 2/2024 | Klie et al. |
| 2024/0037434 A1 | 2/2024 | Boutin et al. |
| 2024/0038329 A1 | 2/2024 | Abeliuk et al. |
| 2024/0038337 A1 | 2/2024 | Laniado et al. |
| 2024/0038340 A1 | 2/2024 | Maeda et al. |
| 2024/0038341 A1 | 2/2024 | Gu et al. |
| 2024/0044884 A1 | 2/2024 | Farokhzad et al. |
| 2024/0044885 A1 | 2/2024 | Farokhzad et al. |
| 2024/0046123 A1 | 2/2024 | Kim |
| 2024/0047006 A1 | 2/2024 | Pan |
| 2024/0047014 A1 | 2/2024 | Yang et al. |
| 2024/0047016 A1 | 2/2024 | Kim |
| 2024/0047018 A1 | 2/2024 | Hanaoka |
| 2024/0053524 A1 | 2/2024 | Schweizer et al. |
| 2024/0054101 A1 | 2/2024 | Chen et al. |
| 2024/0054184 A1 | 2/2024 | Hummelshøj |
| 2024/0054328 A1 | 2/2024 | Li et al. |
| 2024/0054531 A1 | 2/2024 | Tagawa |
| 2024/0055071 A1 | 2/2024 | Zhang et al. |
| 2024/0055080 A1 | 2/2024 | Yang et al. |
| 2024/0061383 A1 | 2/2024 | Lovell et al. |
| 2024/0061403 A1 | 2/2024 | Winkler et al. |
| 2024/0062039 A1 | 2/2024 | Liang et al. |
| 2024/0062131 A1 | 2/2024 | Hajnal et al. |
| 2024/0065613 A1 | 2/2024 | Kandlikar et al. |
| 2024/0070351 A1 | 2/2024 | Hummelshoj |
| 2024/0070353 A1 | 2/2024 | Wang et al. |
| 2024/0070422 A1 | 2/2024 | Church |
| 2024/0071567 A1 | 2/2024 | Westcott et al. |
| 2024/0071575 A1 | 2/2024 | Neumann Barros Ferreira et al. |
| 2024/0071576 A1 | 2/2024 | Neukart et al. |
| 2024/0071577 A1 | 2/2024 | Kirkpatrick et al. |
| 2024/0071578 A1 | 2/2024 | McGrath et al. |
| 2024/0077393 A1 | 3/2024 | Shanai et al. |
| 2024/0078450 A1 | 3/2024 | Rothstein et al. |
| 2024/0079084 A1 | 3/2024 | Townshend et al. |
| 2024/0079099 A1 | 3/2024 | Ishitani et al. |
| 2024/0085389 A1 | 3/2024 | Shanai et al. |
| 2024/0086733 A1 | 3/2024 | Imada |
| 2024/0087686 A1 | 3/2024 | Pritzel et al. |
| 2024/0087688 A1 | 3/2024 | Fain et al. |
| 2024/0093600 A1 | 3/2024 | Li et al. |
| 2024/0096442 A1 | 3/2024 | Bhavnagri |
| 2024/0096444 A1 | 3/2024 | Laniado et al. |
| 2024/0096454 A1 | 3/2024 | Schwartz et al. |
| 2024/0097184 A1 | 3/2024 | Cross et al. |
| 2024/0099165 A1 | 3/2024 | Yang et al. |
| 2024/0104387 A1 | 3/2024 | Alesiani et al. |
| 2024/0105277 A1 | 3/2024 | Kumar et al. |
| 2024/0105287 A1 | 3/2024 | Pan |
| 2024/0105288 A1 | 3/2024 | Takamoto et al. |
| 2024/0111931 A1 | 4/2024 | Oka Hashimoto et al. |
| 2024/0112760 A1 | 4/2024 | Frost et al. |
| 2024/0112762 A1 | 4/2024 | Oh et al. |
| 2024/0112763 A1 | 4/2024 | Garcia Perez et al. |
| 2024/0115742 A1 | 4/2024 | Montclare et al. |
| 2024/0119211 A1 | 4/2024 | Lee et al. |
| 2024/0119273 A1 | 4/2024 | Banerjee et al. |
| 2024/0120022 A1 | 4/2024 | Senior et al. |

(56)　　　　　References Cited

U.S. PATENT DOCUMENTS

| | | |
|---|---|---|
| 2024/0120033 A1 | 4/2024 | Suzuki et al. |
| 2024/0120034 A1 | 4/2024 | Hajnal et al. |
| 2024/0120036 A1 | 4/2024 | Yoshimoto et al. |
| 2024/0121719 A1 | 4/2024 | Vidal et al. |
| 2024/0126942 A1 | 4/2024 | Chen |
| 2024/0127121 A1 | 4/2024 | Shinagawa et al. |
| 2024/0127533 A1 | 4/2024 | Takamoto et al. |
| 2024/0127909 A1 | 4/2024 | Pai et al. |
| 2024/0135141 A1 | 4/2024 | Bae et al. |
| 2024/0136025 A1 | 4/2024 | Xie et al. |
| 2024/0136026 A1 | 4/2024 | Takemoto et al. |
| 2024/0136709 A1 | 4/2024 | Tran et al. |
| 2024/0136710 A1 | 4/2024 | Tran |
| 2024/0142394 A1 | 5/2024 | Pan et al. |
| 2024/0144045 A1 | 5/2024 | Amii et al. |
| 2024/0144046 A1 | 5/2024 | Amii et al. |
| 2024/0152668 A1 | 5/2024 | Yu et al. |
| 2024/0152750 A1 | 5/2024 | Schockaert |
| 2024/0152756 A1 | 5/2024 | Lakshmanan et al. |
| 2024/0152763 A1 | 5/2024 | Aliper et al. |
| 2024/0153188 A1 | 5/2024 | Wang et al. |
| 2024/0153595 A1 | 5/2024 | Alampara et al. |
| 2024/0160858 A1 | 5/2024 | Dai et al. |
| 2024/0267117 A1 | 8/2024 | Guiney et al. |
| 2024/0302532 A1 | 9/2024 | Reid et al. |
| 2024/0308696 A1 | 9/2024 | Mukae |
| 2024/0396626 A1 | 11/2024 | Atungsiri et al. |
| 2025/0219720 A1 | 7/2025 | Prasad et al. |

FOREIGN PATENT DOCUMENTS

| | | |
|---|---|---|
| AU | 2004311881 B2 | 7/2008 |
| CA | 2220216 A1 | 11/1996 |
| CA | 2548669 C | 5/2014 |
| CA | 2821652 C | 7/2014 |
| CN | 113434292 A | 9/2021 |
| CN | 117639885 A | 3/2024 |
| DK | 3430485 T3 | 8/2021 |
| EP | 0826205 B1 | 2/2003 |
| EP | 2600174 A1 | 6/2013 |
| EP | 3468868 B1 | 5/2021 |
| EP | 3430485 B1 | 6/2021 |
| EP | 3889719 A1 | 10/2021 |
| EP | 3965515 A1 | 3/2022 |
| EP | 3968675 A1 | 3/2022 |
| EP | 4002904 A1 | 5/2022 |
| EP | 4019413 A1 | 6/2022 |
| EP | 3830980 A4 | 8/2022 |
| EP | 4292945 A1 | 12/2023 |
| GB | 2426647 B | 2/2008 |
| GB | 2597192 B | 7/2023 |
| IL | 240069 B | 8/2018 |
| IN | 3236/DELNP/2006 B | 8/2007 |
| JP | S608199 A | 1/1985 |
| JP | S60051383 A | 3/1985 |
| JP | 4-78519 B2 | 12/1992 |
| NL | 2009635 C2 | 4/2014 |
| WO | 1996035197 A1 | 11/1996 |
| WO | 2004015878 A3 | 8/2004 |
| WO | 2005065320 A2 | 7/2005 |
| WO | 2008138996 A1 | 11/2008 |
| WO | 2014042718 A2 | 3/2014 |
| WO | 2014042718 A3 | 6/2014 |
| WO | 2017218696 A1 | 12/2017 |
| WO | 2018098588 A1 | 6/2018 |
| WO | 2018106289 A1 | 6/2018 |
| WO | 2018106290 A1 | 6/2018 |
| WO | 2018112460 A1 | 6/2018 |
| WO | 2018145262 A1 | 8/2018 |
| WO | 2019005908 A1 | 1/2019 |
| WO | 2019060268 A1 | 3/2019 |
| WO | 2019154246 A1 | 8/2019 |
| WO | 2019199651 A1 | 10/2019 |
| WO | 2019209888 A1 | 10/2019 |
| WO | 2019244125 A2 | 12/2019 |
| WO | 2019244125 A3 | 3/2020 |
| WO | 2020047469 A2 | 3/2020 |
| WO | 2020051508 A1 | 3/2020 |
| WO | 2020056405 A1 | 3/2020 |
| WO | 2020065462 A1 | 4/2020 |
| WO | 2020065463 A1 | 4/2020 |
| WO | 2020096774 A1 | 5/2020 |
| WO | 2020123505 A1 | 6/2020 |
| WO | 2020047469 A3 | 7/2020 |
| WO | 2020148588 A1 | 7/2020 |
| WO | 2020163967 A1 | 8/2020 |
| WO | 2020188549 A2 | 9/2020 |
| WO | 2020209591 A1 | 10/2020 |
| WO | 2020215056 A1 | 10/2020 |
| WO | 2020263358 A1 | 12/2020 |
| WO | 2020263358 A8 | 2/2021 |
| WO | 2021034590 A1 | 2/2021 |
| WO | 2021034910 A1 | 2/2021 |
| WO | 2021040743 A1 | 3/2021 |
| WO | 2020188549 A3 | 4/2021 |
| WO | 2021092039 A1 | 5/2021 |
| WO | 2021113086 A1 | 6/2021 |
| WO | 2021231457 A1 | 11/2021 |
| WO | 2021252460 A1 | 12/2021 |
| WO | 2022040366 A1 | 2/2022 |
| WO | 2022067211 A1 | 3/2022 |
| WO | 2022074643 A1 | 4/2022 |
| WO | 2022090579 A1 | 5/2022 |
| WO | 2021252460 A9 | 6/2022 |
| WO | 2022117664 A1 | 6/2022 |
| WO | 2022132050 A1 | 6/2022 |
| WO | 2022182899 A1 | 9/2022 |
| WO | 2022204682 A1 | 9/2022 |
| WO | 2022212215 A1 | 10/2022 |
| WO | 2022261674 A1 | 12/2022 |
| WO | 2022261675 A1 | 12/2022 |
| WO | 2022261676 A1 | 12/2022 |
| WO | 2022261678 A1 | 12/2022 |
| WO | 2022266002 A1 | 12/2022 |
| WO | 2022266349 A2 | 12/2022 |
| WO | 2022269613 A1 | 12/2022 |
| WO | 2022266349 A3 | 1/2023 |
| WO | 2023003726 A1 | 1/2023 |
| WO | 2023003727 A1 | 1/2023 |
| WO | 2023283437 A1 | 1/2023 |
| WO | 2023012700 A1 | 2/2023 |
| WO | 2023003727 A4 | 3/2023 |
| WO | 2023031122 A1 | 3/2023 |
| WO | 2023064999 A1 | 4/2023 |
| WO | 2023081827 A1 | 5/2023 |
| WO | 2023113874 A1 | 6/2023 |
| WO | 2023115217 A1 | 6/2023 |
| WO | 2023156620 A1 | 8/2023 |
| WO | 2023164518 A2 | 8/2023 |
| WO | 2023192428 A1 | 10/2023 |
| WO | 2023205540 A1 | 10/2023 |
| WO | 2023213821 A1 | 11/2023 |
| WO | 2023242003 A1 | 12/2023 |
| WO | 2023250152 A1 | 12/2023 |
| WO | 2024018448 A2 | 1/2024 |
| WO | 2024030920 A2 | 2/2024 |
| WO | 2024042508 A1 | 2/2024 |
| WO | 2024046603 A1 | 3/2024 |
| WO | 2024047236 A1 | 3/2024 |
| WO | 2024082694 A1 | 4/2024 |
| WO | 2024091926 A1 | 5/2024 |

OTHER PUBLICATIONS

Szymanski et al., "An autonomous laboratory for the accelerated synthesis of novel materials," Nature, Nov. 2023, 12 pages.
Yang et al., "Scalable Diffusion for Materials Generation," Google DeepMind, Oct. 17, 2023, pp. 1-18.
Zeni et al., "MatterGen: a generative model for inorganic materials design," arXiv, 2023, 56 pages, retrieved from https://arxiv.org/abs/2312.03687#:~:text=Here%2C%20we%20present%20MatterGen%2C%20a,broad%20range%20of%20property%20constraints.

(56) References Cited

OTHER PUBLICATIONS

Xin et al., "Active learning based generative design for the discovery of wide band gap materials," arXiv, 2021, 16 pages, retrieved from https://arxiv.org/abs/2103.00608.

Anstine et al., "Generative Models as an Emerging Paradigm in the Chemical Sciences," Journal of the American Chemical Society, vol. 145, 2023, pp. 8736-8750.

Hu et al., "Deep language models for interpretative and predictive materials science," APL Machine Learning, vol. 1, Feb. 2023, 19 pages.

Agrawal et al., "Deep materials informatics: Applications of deep learning in materials science," MRS Communications, vol. 9, 2019, pp. 779-792.

Chen et al., "Leveraging Large-scale Computational Database and Deep Learning for Accurate Prediction of Material Properties," arXiv, 2021, 16 pages, retrieved from https://arxiv.org/abs/2112.14429.

Wang et al., "Inverse Design of Materials by Machine Learning," Materials, vol. 15, 2022, pp. 1-19.

Chen et al., "Generative Deep Neural Networks for Inverse Materials Design Using Backpropagation and Active Learning," Advanced Science News, vol. 7, 2020, pp. 1-10.

Weiss et al., "Guided diffusion for inverse molecular design," Nature Computational Science, vol. 3, Oct. 2023, pp. 873-882.

Song et al., "Computational Discovery of New 2D Materials Using Deep Learning Generative Models," Applied Materials & Interfaces, vol. 13, 2021, pp. 53303-53313.

Bajpai et al., "A scalable crystal representation for reverse engineering of novel inorganic materials using deep generative models," ChemRxiv, Mar. 2023, 29 pages, retrieved from https://chemrxiv.org/engage/chemrxiv/article-details/641b37052bfb3dc25130e17d.

Barrett, R., "Artificial Intelligence and Augmented Intelligence for Automated Investigations for Scientific Discovery," University of Warwick, Project Report, Sep. 15, 2021, 11 pages.

Song et al., "Predicting Material Structures and Properties Using Deep Learning and Machine Learning Algorithms," University of South Carolina Scholar Commons, Theses and Dissertations, 2023, 137 pages.

Zhang et al., "Generating and screening de novo compounds against given targets using ultrafast deep learning models as core components," Briefings in Bioinformatics, vol. 23, 2022, pp. 1-15.

Christensen et al., "Predictive and generative machine learning models for photonic crystals," Nanophotonics, vol. 9, 2020, pp. 4183-4192.

Baillif et al., "Deep generative models for 3D molecular structure," ScienceDirect, Current Opinion in Structural Biology, vol. 80, 2023, pp. 1-10.

Chen et al., "Generative models for inverse design of inorganic solid materials," Journal of Materials Informatics, 2021, pp. 1-15.

Kadulkar et al., "Machine Learning-Assisted Design of Material Properties," Annual Review of Chemical and Biomolecular Engineering, 2022, 23 pages.

Hu et al., "MaterialsAtlas.org: a materials informatics web app platform for materials discovery and survey of state-of-the-art," NPJ Computational Materials, 2022, pp. 1-12.

Fu et al., "Materials Transformers Language Models for Generative Materials Design: a benchmark study," 2022, pp. 1-19, retrieved from https://arxiv.org/abs/2206.13578.

Menon et al., "A Generative Approach to Materials Discovery, Design, and Optimization," ACS Omega, vol. 7, 2022, pp. 25958-25973.

Manica et al., "Accelerating material design with the generative toolkit for scientific discovery," NPJ Computational Materials, 2023, pp. 1-6.

Debnath et al., "Generative deep learning as a tool for inverse design of high-entropy refractory alloys," arXiv, 2021, 20 pages, retrieved from https://arxiv.org/pdf/2108.12019.pdf.

Regenwetter et al., "Deep Generative Models in Engineering Design: A Review," The Journal of Mechanical Design, vol. 144, Jul. 2022, 23 pages, retrieved from https://decode.mit.edu/assets/papers/2022_regenwetter_review.pdf.

Hsu et al., "Generative design, manufacturing, and molecular modeling of 3D architected materials based on natural language input," APL Materials, vol. 10, Apr. 13, 2022, pp. 14 pages.

Mamun et al., "Machine learning augmented predictive and generative model for rupture life in ferritic and austenitic steels," NPJ Materials Degradation, 2021, pp. 1-10.

Wei et a., "Probabilistic generative transformer language models for generative design of molecules," Journal of Cheminformatics, 2023, pp. 1-15.

Fuhr et al., "Deep Generative Models for Materials Discovery and Machine Learning-Accelerated Innovation," Frontiers in Materials, vol. 9, Mar. 2022, pp. 1-13.

Zhang et al., "Multi-objective Generative Design of Three-Dimensional Composite Materials," arXiv, 2023, 29 pages, retrieved from https://arxiv.org/abs/2302.13365.

Xue et al., "Machine learning generative models for automatic design of multi-material 3D printed composite solids," Extreme Mechanics Letters, vol. 41, 2020, pp. 1-7.

New et al., "Evaluating the diversity and utility of materials proposed by generative models," arXiv, 2023, 12 pages, retrieved from https://arxiv.org/abs/2309.12323.

Eguchi et al., "Ig-VAE: Generative modeling of protein structure by direct 3D coordinate generation," PLOS Computational Biology, Jun. 27, 2022, pp. 1-18.

Chu et al., "An all-atom protein generative model," bioRxiv, 2023, 20 pages, retrieved from https://www.biorxiv.org/content/10.1101/2023.05.24.542194v1.full.

Vasudevan et al., "Machine learning for materials design and discovery," Journal of Applied Physics, vol. 129, Feb. 2021, pp. 1-8.

Shen et al., "Nature-inspired architected materials using unsupervised deep learning," Communications Engineering, 2022, pp. 1-15.

Kong et al., "Materials representation and transfer learning for multi-property prediction," Applied Physics Reviews, Jun. 2021, 15 pages.

Rajak et al.,. "Predictive Synthesis of Quantum Materials by Probabilistic Reinforcement Learning," arXiv, 2020, 16 pages, retrieved from https://arxiv.org/abs/2009.06739.

Ni et al., "Generative design of de novo proteins based on secondary-structure constraints using an attention-based diffusion model," Chem, vol. 9, Jul. 13, 2023, pp. 1828-1849.

Jackson et al., "Recent advances in machine learning towards multiscale soft materials design," Current Opinion in Chemical Engineering, vol. 23, 2019, pp. 106-114.

Choung et al., "Extracting medicinal chemistry intuition via preference machine learning," Nature Communications, vol. 14, Oct. 31, 2023, pp. 1-10.

Dan et al., "Generative adversarial networks (GAN) based efficient sampling of chemical composition space for inverse design of inorganic materials," NPJ Computational Materials, Jun. 26, 2020, pp. 1-7.

Iovanac et al., "Improving the generative performance of chemical autoencoders through transfer learning," Machine Learning Science and Technology, vol. 1, 2020, 12 pages.

Liu et al., "Tackling Photonic Inverse Design with Machine Learning," Advanced Science, vol. 8, 2021, pp. 1-15.

Garland et al., "Pragmatic generative optimization of novel structural lattice metamaterials with machine learning," Materials and Design, vol. 203, 2021, pp. 1-13.

Mobarak et al., "Scope of machine learning in materials research-A review," Applied Surface Science Advances, vol. 18, 2023, pp. 1-24.

Lu et al., "Computational discovery of energy materials in the era of big data and machine learning: A critical review," Materials Reports: Energy, vol. 1, 2021, pp. 1-18.

Bandi et al., "The Power of Generative AI: A Review of Requirements, Models, Input-Output Formats, Evaluation Metrics, and Challenges," Future Internet, vol. 15, 2023, pp. 1-60.

Wan et al., "Machine Learning Paves the Way for High Entropy Compounds Exploration: Challenges, Progress, and Outlook," Advanced Materials, 2023, pp. 1-26.

(56) References Cited

OTHER PUBLICATIONS

Hoja et al., "First-principles modeling of molecular crystals: structures and stabilities, temperature and pressure," Advanced Reviews, vol. 7, 2017, pp. 1-26.

Non-Final Office Action from U.S. Appl. No. 18/397,993, dated Aug. 29, 2024.

Bogojeski et al., "Quantum Chemical Accuracy from Density Functional Approximations via Machine Learning," Nature Communications, 2020, with supplementary information, 36 pages.

Antoniuk et al., "Predicting the Synthesizability of Crystalline Inorganic Materials from the Data of Known Material Compositions," npj Computational Materials, 2023, pp. 1-11.

Fedik et al., "Extending Machine Learning beyond Interatomic Potentials for Predicting Molecular Properties," Nature Reviews, vol. 6, Sep. 2022, pp. 653-672.

Ramprasad et al., "Machine Learning in Materials Informatics: Recent Applications and Prospects," npj Computational Materials, 2017, pp. 1-13.

Ceriotti, M., "Beyond Potentials: Integrated Machine Learning Models for Materials," MRS Bulletin, vol. 47, Oct. 2022, pp. 1045-1053.

Huang et al., "Application of Machine Learning in Material Synthesis and Property Prediction," Materials, 2023, pp. 1-30.

Prasad et al., U.S. Appl. No. 18/889,200, filed Sep. 18, 2024.

Prasad et al., U.S. Appl. No. 18/889,213, filed Sep. 18, 2024.

Prasad et al., U.S. Appl. No. 18/889,227, filed Sep. 18, 2024.

Li et al., "A Machine Learning-based Approach for Improved Orbit Predictions of LEO Space Debris With Sparse Tracking Data From a Single Station," IEEE Transactions on Aerospace and Electronic Systems, vol. 56, 2020, pp. 1-15.

Haidar-Ahmad et al., "A Hybrid Analytical-Machine Learning Approach for LEO Satellite Orbit Prediction," IEEE 25th International Conference on Information Fusion (Fusion), 2022, 7 pages.

Wrona et al., "Artifcial Intelligence-Based Data Path Control in LEO Satellites-Driven Optical Communications," International Journal of Satellite Communications and Networking, 2023, 24 pages.

Brenna, M., "CubeSat mission design for in-orbit environment characterisation," Master Thesis, Politecnico di Milano, Dec. 2020, 150 pages.

Homssi et al., "Deep Learning Forecasting and Statistical Modeling for Q/V-Band LEO Satellite Channels," IEEE Transactions on Machine Learning in Communications and Networking, vol. 1, Jun. 2023, pp. 78-89.

Gorooh et al., "Integrating LEO and GEO Observations: Toward Optimal Summertime Satellite Precipitation Retrieval," Journal of Hydrometeorology, vol. 24, Nov. 2023, pp. 1939-1954.

Chen et al., "Orbit Manoeuvre Strategies for Very Low Earth Orbit (VLEO) Satellites," 74th International Astronautical Congress (IAC), Oct. 2023, pp. 1-6.

Kim et al., "ARMA Prediction of SBAS Ephemeris and Clock Corrections for Low Earth Orbiting Satellites," Hindawi International Journal of Aerospace Engineering, 2015, 8 pages.

Kozhaya et al., "Comparison of Neural Network Architectures for Simultaneous Tracking and Navigation with LEO Satellites," Preprint of the 2021 ION GNSS+ Conference, Sep. 2021, 14 pages.

Lee et al., "Machine Learning Approach to Initial Orbit Determination of Unknown LEO Satellites," SpaceOps Conferences, Jun. 2018, pp. 1-11.

Ge et al., "LEO Enhanced Global Navigation Satellite System (LeGNSS): progress, opportunities, and challenges," Geo-spatial Information Science, vol. 25, Oct. 2021, pp. 1-13.

Mortlock et al., "Assessing Machine Learning for LEO Satellite Orbit Determination in Simultaneous Tracking and Navigation," Ohio State University, 2022, 8 pages, retrieved from https://ece.osu.edu/sites/default/files/2022-09/Assessing_machine_learning_for_LEO_satellite_orbit_determination_in_simultaneous_tracking_and_navigation.pdf.

O'Meara et al., "Applications of Deep Learning Neural Networks to Satellite Telemetry Monitoring," SpaceOps Conferences, Jun. 2018, pp. 1-16.

Ibrahim et al., "Anticipating Optical Availability in Hybrid RF/FSO Links Using RF Beacons and Deep Learning," arXiv, 2024, 11 pages, retrieved from https://arxiv.org/abs/2405.13366.

Prol et al., "Position, Navigation, and Timing (PNT) Through Low Earth Orbit (LEO) Satellites: A Survey on Current Status, Challenges, and Opportunities," IEEE Access, vol. 10, 2022, pp. 83971-84002.

Najder et al., "Quality of Orbit Predictions for Satellites Tracked by SLR Stations," Remote Sensing, vol. 13, Apr. 3, 2021, pp. 1-20.

Carr et al., "Multi-LEO Satellite Stereo Winds," Remote Sensing, vol. 15, pp. 1-31.

Hornillo-Mellado et al., "Prediction of Satellite Shadowing in Smart Cities with Application to loT," Sensors, vol. 20, 2020, pp. 1-19.

Celikbilek et al., "Survey on Optimization Methods for LEO-Satellite-Based Networks with Applications in Future Autonomous Transportation," Sensors, vol. 22, 2022, pp. 1-52.

Na et al., "Distributed Routing Strategy Based on Machine Learning for LEO Satellite Network," Hindawi Wireless Communications and Mobile Computing, Jun. 2018, pp. 1-10.

Yao et al., "Machine learning for a sustainable energy future," Perspectives, vol. 8, Mar. 2023, pp. 202-215.

Bhowmik et al., "A perspective on inverse design of battery interphases using multi-scale modelling, experiments and generative deep learning," Energy Storage Materials, vol. 21, 2019, pp. 446-456.

Willard et al., "Integrating Scientific Knowledge with Machine Learning for Engineering and Environmental Systems," ACM Computing Surveys, vol. 55, No. 4, Nov. 2022, pp. 1-37.

Kaszuba et al., "Compositional Search of Stable Crystalline Structures in Multi-Component Alloys Using Generative Diffusion Models," arXiv, 2023, 14 pages, retrieved from https://arxiv.org/abs/2312.16073.

Wei et al., "Perspective: Predicting and optimizing thermal transport properties with machine learning methods," Energy and Al, vol. 8, 2022, pp. 1-14.

Keith et al., "Combining Machine Learning and Computational Chemistry for Predictive Insights Into Chemical Systems," Chemical Reviews, vol. 121, 2021, pp. 9816-9872.

Marani et al., "Predicting Ultra-High-Performance Concrete Compressive Strength Using Tabular Generative Adversarial Networks," Materials, Oct. 24, 2020, vol. 13, pp. 1-24.

Dash et al., "A review of Generative Adversarial Networks (GANs) and its applications in a wide variety of disciplines—From Medical to Remote Sensing," arXiv, 2021, 41 pages, retrieved from.

Noh et al., "Machine-enabled inverse design of inorganic solid materials: promises and challenges," Chemical Science, vol. 11, 2020, pp. 4871-4881.

Nguyen et al., "Synthesizing controlled microstructures of porous media using generative adversarial networks and reinforcement learning," Scientific Reports, 2022, pp. 1-16.

Zhang et al., "An equivariant generative framework for molecular graph-structure Co-design," Chemical Science, vol. 14, 2023, pp. 8380-8392.

Jablonka et al., "Big-Data Science in Porous Materials: Materials Genomics and Machine Learning," Chemical Reviews, vol. 120, 2020, pp. 8066-8129.

Vlassis et al., "Denoising diffusion algorithm for inverse design of microstructures with fine-tuned nonlinear material properties," arXiv, 2023, 21 pages, retrieved from https://arxiv.org/abs/2302.12881.

Bellovin et al., "Privacy and Synthetic Datasets," Stanford Technology Law Review, Forthcoming, SSRN, 2018, 39 pages, retrieved from https://papers.ssrn.com/sol3/papers.cfm?abstract_id=3255766.

Biron, L., "Google DeepMind Adds Nearly 400,000 New Compounds to Berkeley Lab's Materials Project," News From Berkeley Lab, Nov. 29, 2023, 11 pages, retrieved from https://newscenter.lbl.gov/2023/11/29/google-deepmind-new-compounds-materials-project/.

Kim, J., "Google DeepMind's new AI tool helped create more than 700 new materials," MIT Technology Review, Nov. 29, 2023, 10 pages, retrieved from https://www.technologyreview.com/2023/11/29/1084061/deepmind-ai-tool-for-new-materials-discovery/.

(56) References Cited

OTHER PUBLICATIONS

Berkley Lab, "The Materials Project," Berkley Lab, 2023, 5 pages, retrieved from https://next-gen.materialsproject.org/.

Restriction Requirement from U.S. Appl. No. 18/397,993, dated May 3, 2024.

Vikoren et al., U.S. Appl. No. 18/397,993, filed Dec. 27, 2023.

Kulik et al., "Roadmap on Machine learning in electronic structure," Electronic Structure, vol. 4, 2022, pp. 1-60.

Su et al. "Efficient determination of the Hamiltonian and electronic properties using graph neural network with complete local coordinates," Machine Learning Science and Technology, vol. 4, 2023, pp. 1-13.

Yu et al., "QH9: A Quantum Hamiltonian Prediction Benchmark for QM9 Molecules," 37th Conference on Neural Information Processing Systems (NeurIPS), 2023, 17 pages.

Garrity et al., "Database of Wannier tightbinding Hamiltonians using high-throughput density functional theory," Scientific Data, 2021, pp. 1-10.

Mueller et al., "Machine learning for interatomic potential models," The Journal of Chemical Physics, vol. 152, Feb. 5, 2020, pp. 1-13.

Bai et al., "Graph Neural Network for Hamiltonian-Based Material Property Prediction," arXiv, 2020, pp. 1-9, retrieved from https://arxiv.org/pdf/2005.13352.

Rodriguez, A., "Development of Atomistic Machine Learning Approaches for Thermal Properties of Multi-Component Solids and Liquids," Thesis, University of South Carolina, Summer 2023, 242 pages.

Reiser et al., "Graph neural networks for materials science and chemistry," Communications Materials, 2022, pp. 1-18.

Bao et al., "Deep-Learning Database of Density Functional Theory Hamiltonians for Twisted Materials," arXiv, 2024, pp. 1-12, retrieved from https://arxiv.org/pdf/2404.06449.

Khrabrov et al., "nablaDFT: Large-Scale Conformational Energy and Hamiltonian Prediction benchmark and dataset," Physical Chemistry Chemical Physics, vol. 24, 2022, pp. 25853-25863.

Hegde et al., "Machine-learned approximations to Density Functional Theory Hamiltonians," Scientific Reports, Feb. 15, 2017, pp. 1-11.

Anker et al., "Machine learning for analysis of experimental scattering and spectroscopy data in materials chemistry," Chemical Science, vol. 14, 2023, pp. 14003-14019.

Ryu et al., "Quantum Graph Neural Network Models for Materials Search," Materials, vol. 16, 2023, pp. 1-26.

Lu et al., "When Machine Learning Meets 2D Materials: A Review," Advanced Science, vol. 11, 2024, pp. 1-40.

Zhong et al., "Universal Machine Learning Kohn-Sham Hamiltonian for Materials," arXiv, 2024, 20 pages, retrieved from https://arxiv.org/abs/2402.09251.

Ojih et al., "Graph theory and graph neural network assisted high-throughput crystal structure prediction and screening for energy conversion and storage," Journal of Materials Chemistry A, vol. 12, 2024, pp. 8502-8515.

Farahvash et al., "Machine learning Frenkel Hamiltonian parameters to accelerate simulations of exciton dynamics," The Journal of Chemical Physics, vol. 153, 2020, 14 pages.

Conway et al., "3.12—First principles crystal structure prediction," Comprehensive Inorganic Chemistry III (Third Edition), 2023, pp. 393-420.

Zhou et al., "Deep learning of dynamically responsive chemical Hamiltonians with semiempirical quantum mechanics," PNAS, vol. 119, No. 27, 2022, pp. 1-10.

Yu et al., "Efficient and Equivariant Graph Networks for Predicting Quantum Hamiltonian," Proceedings of the 40 th International Conference on Machine Learning, 2023, pp. 1-13.

Alibakhshi et al., "Implicitly perturbed Hamiltonian as a class of versatile and general-purpose molecular representations for machine learning," Nature Communications, 2022, pp. 1-10.

Lal et al., "AI-Based Nano-Scale Material Property Prediction for Li-Ion Batteries," Batteries, vol. 10, pp. 1-13.

Cheng et al., "Revealing Topology in Metals using Experimental Protocols Inspired by K-Theory," arXiv, 2023, 12 pages, retrieved from https://arxiv.org/pdf/2209.02891.

Schleder et al., "From DFT to machine learning: recent approaches to materials science—a review," Journal of Physics: Materials, vol. 2, 2019, pp. 1-46.

Neves et al., "Crystal net catalog of model flat band materials," npj Computational Materials, 2024, pp. 1-9.

Yin et al., "Harmonizing SO(3)-Equivariance with Neural Expressiveness: a Hybrid Deep Learning Framework Oriented to the Prediction of Electronic Structure Hamiltonian," arXiv, 2024, 37 pages, retrieved from https://arxiv.org/pdf/2401.00744v9.

Beran, G., "Frontiers of molecular crystal structure prediction for pharmaceuticals and functional organic materials," Chemical Science, vol. 14, 2023, pp. 13290-13312.

Sander et al., "Towards Hamiltonian Simulation with Decision Diagrams," arXiv, 2024, 12 pages, retrieved from https://arxiv.org/pdf/2305.02337.

Zhang et al., "Equivariant analytical mapping of first principles Hamiltonians to accurate and transferable materials models," npj Computational Materials, 2022, pp. 1-14.

Hegde, R., "Deep learning: a new tool for photonic nanostructure design," Nanoscale Advances, vol. 2, 2020, pp. 1007-1023.

Vasudevan et al., "Materials Science in the AI age: high-throughput library generation, machine learning and a pathway from correlations to the underpinning physics," Author Manuscript, MRS Comm., 2019, pp. 1-34.

Non-Final Office Action from U.S. Appl. No. 18/889,227, dated Dec. 18, 2024.

Notice of Allowance from U.S. Appl. No. 18/889,227, dated Apr. 7, 2025.

Corrected Notice of Allowance from U.S. Appl. No. 18/889,227, dated Apr. 23, 2025.

Non-Final Office Action from U.S. Appl. No. 18/889,213, dated Aug. 12, 2025.

* cited by examiner

101

SATELLITE(s)
AND PAYLOAD
MANAGEMENT
107

105
SATELLITE OPTIMIZATION SYSTEM
BASED ON MACHINE LEARNING

103
NATURAL LANGUAGE
BASED INPUT

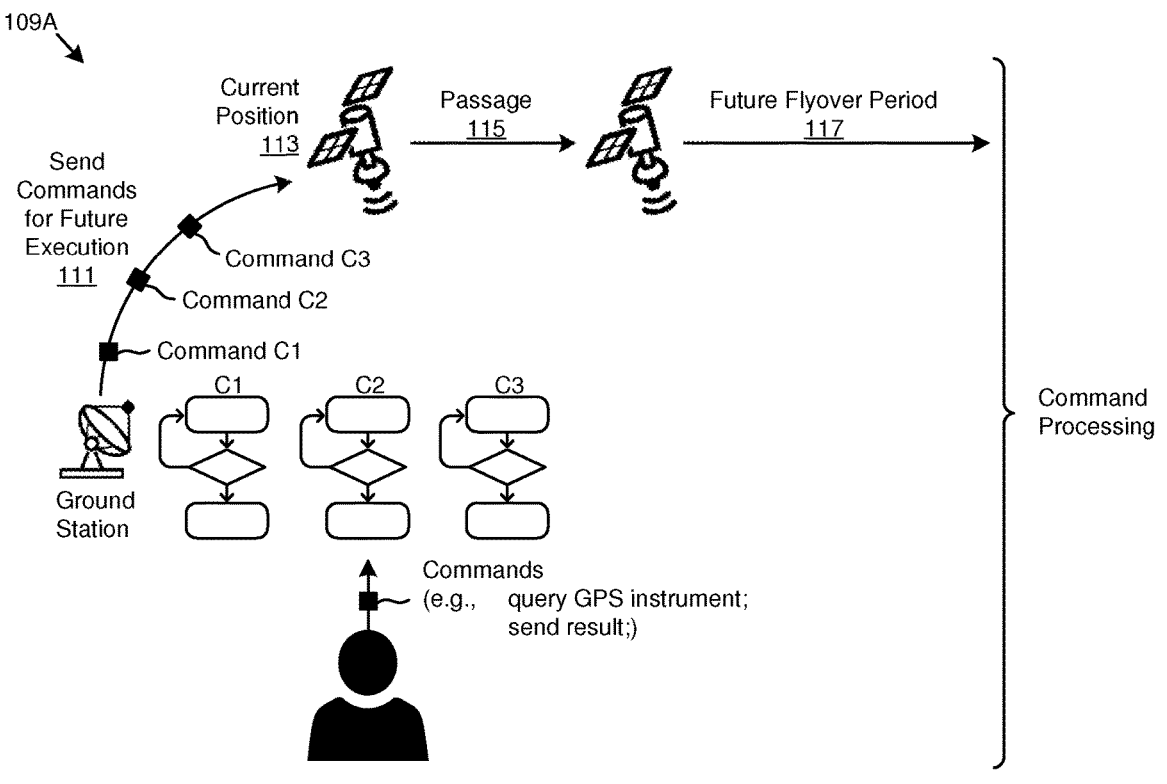
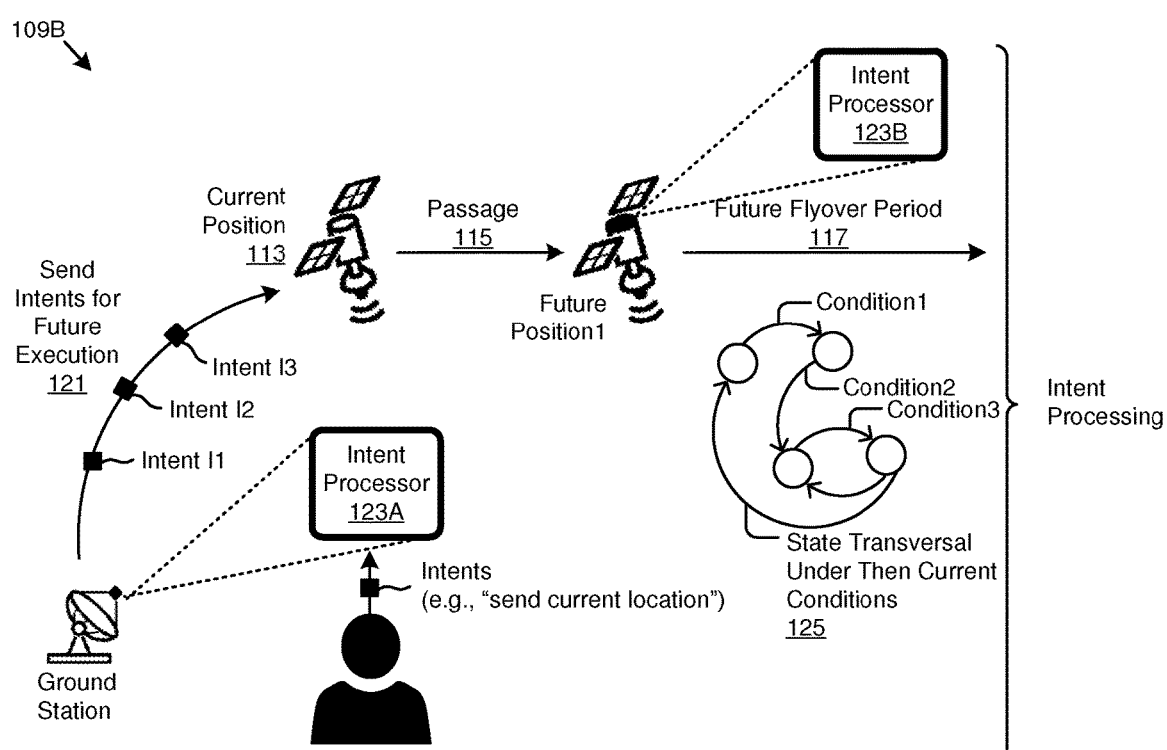
FIG. 1B

500

700

| | | | |
|---|---|---|---|
| = GROUND STATIONS 704 | = CLOUD DATACENTER 706 | = MISSION CONTROL 708 | = BACK OFFICE 710 |

800

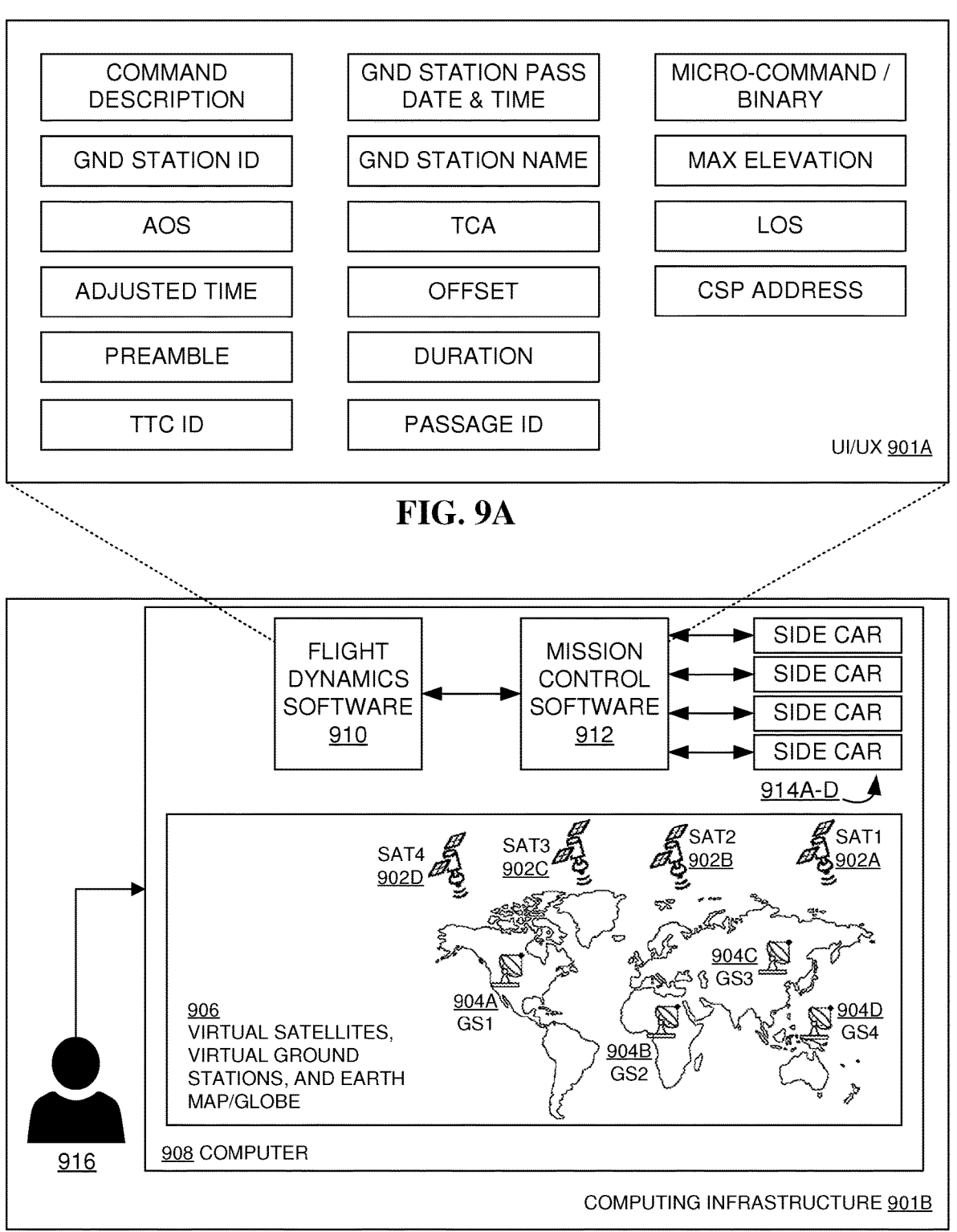

| COMMAND DESCRIPTION | GND STATION PASS DATE & TIME | MICRO-COMMAND / BINARY |
|---|---|---|
| GND STATION ID | GND STATION NAME | MAX ELEVATION |
| AOS | TCA | LOS |
| ADJUSTED TIME | OFFSET | CSP ADDRESS |
| PREAMBLE | DURATION | |
| TTC ID | PASSAGE ID | |

FLIGHT DYNAMICS SOFTWARE 910

MISSION CONTROL SOFTWARE 912

SIDE CAR
SIDE CAR
SIDE CAR
SIDE CAR
914A-D

SAT4 902D    SAT3 902C    SAT2 902B    SAT1 902A

904C GS3

904A GS1

904D GS4

904B GS2

906
VIRTUAL SATELLITES, VIRTUAL GROUND STATIONS, AND EARTH MAP/GLOBE

908 COMPUTER

916

COMPUTING INFRASTRUCTURE 901B

FIG. 9B

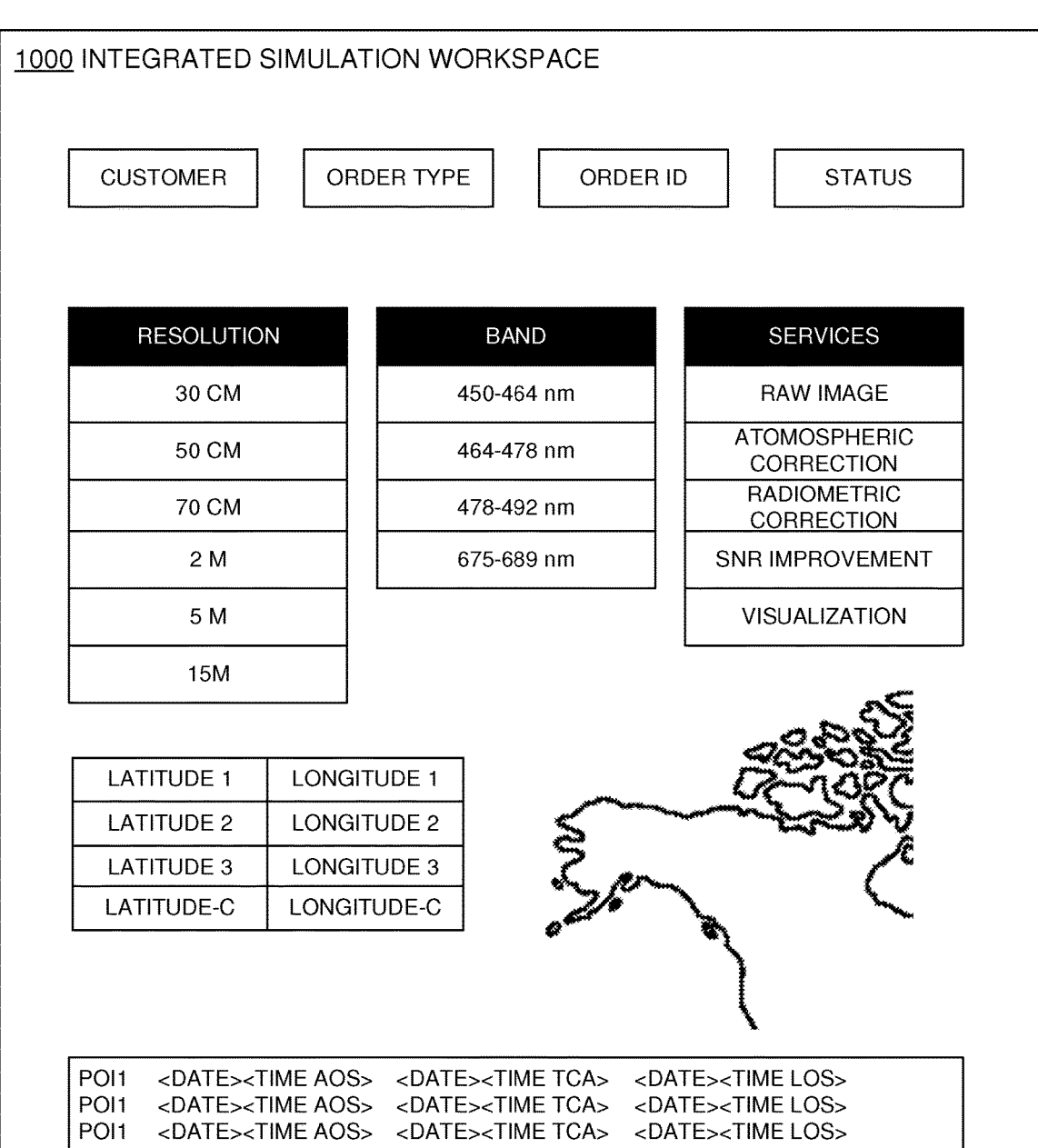

1000 INTEGRATED SIMULATION WORKSPACE

| CUSTOMER | ORDER TYPE | ORDER ID | STATUS |

| RESOLUTION |
| --- |
| 30 CM |
| 50 CM |
| 70 CM |
| 2 M |
| 5 M |
| 15M |

| BAND |
| --- |
| 450-464 nm |
| 464-478 nm |
| 478-492 nm |
| 675-689 nm |

| SERVICES |
| --- |
| RAW IMAGE |
| ATOMOSPHERIC CORRECTION |
| RADIOMETRIC CORRECTION |
| SNR IMPROVEMENT |
| VISUALIZATION |

| LATITUDE 1 | LONGITUDE 1 |
| --- | --- |
| LATITUDE 2 | LONGITUDE 2 |
| LATITUDE 3 | LONGITUDE 3 |
| LATITUDE-C | LONGITUDE-C |

POI1   <DATE><TIME AOS>   <DATE><TIME TCA>   <DATE><TIME LOS>
POI1   <DATE><TIME AOS>   <DATE><TIME TCA>   <DATE><TIME LOS>
POI1   <DATE><TIME AOS>   <DATE><TIME TCA>   <DATE><TIME LOS>

POI2   <DATE><TIME AOS>   <DATE><TIME TCA>   <DATE><TIME LOS>
POI2   <DATE><TIME AOS>   <DATE><TIME TCA>   <DATE><TIME LOS>
POI2   <DATE><TIME AOS>   <DATE><TIME TCA>   <DATE><TIME LOS>

SIMULATION RESULT

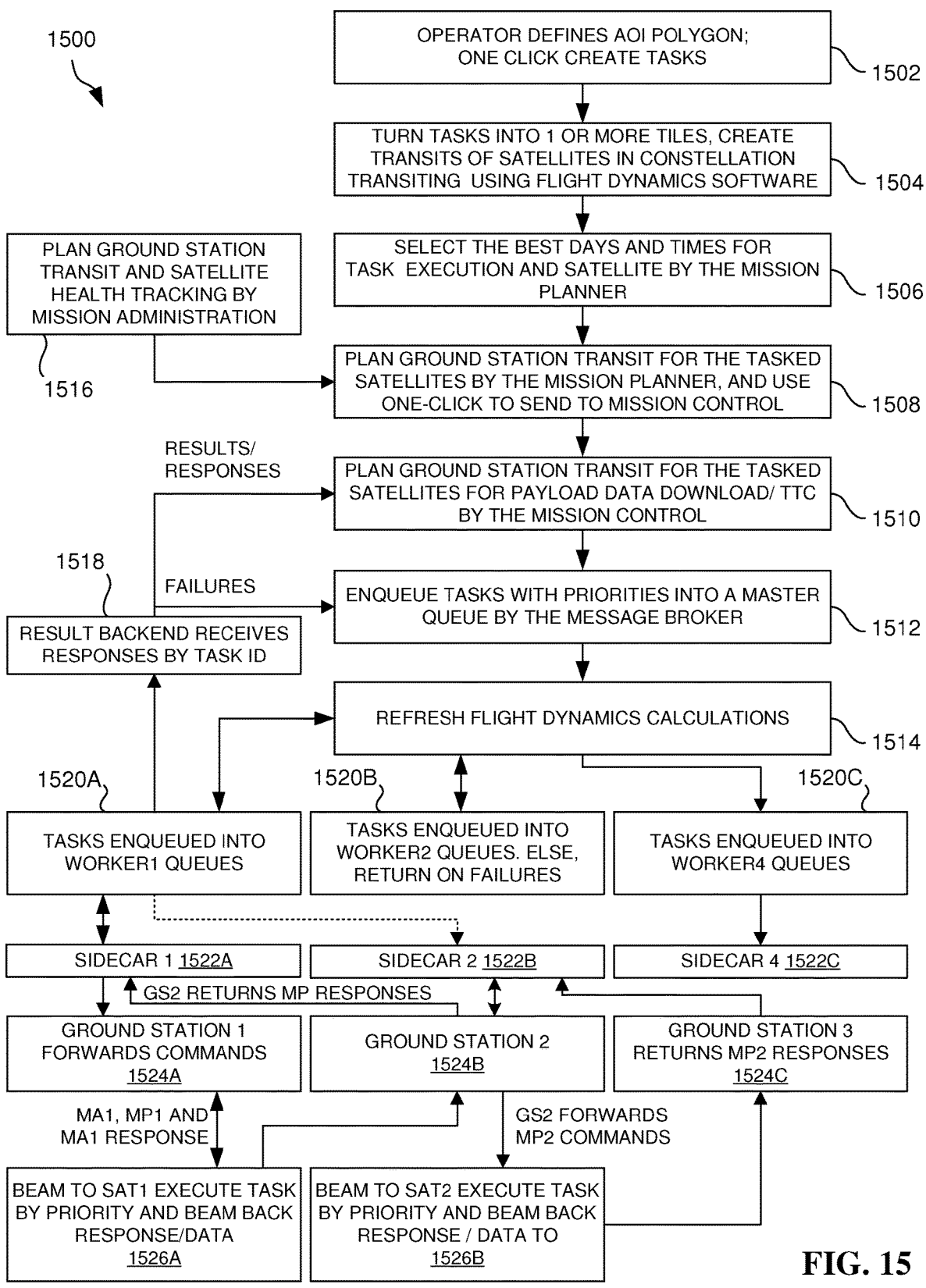

1500

OPERATOR DEFINES AOI POLYGON; ONE CLICK CREATE TASKS — 1502

TURN TASKS INTO 1 OR MORE TILES, CREATE TRANSITS OF SATELLITES IN CONSTELLATION TRANSITING USING FLIGHT DYNAMICS SOFTWARE — 1504

PLAN GROUND STATION TRANSIT AND SATELLITE HEALTH TRACKING BY MISSION ADMINISTRATION — 1516

SELECT THE BEST DAYS AND TIMES FOR TASK EXECUTION AND SATELLITE BY THE MISSION PLANNER — 1506

PLAN GROUND STATION TRANSIT FOR THE TASKED SATELLITES BY THE MISSION PLANNER, AND USE ONE-CLICK TO SEND TO MISSION CONTROL — 1508

RESULTS/ RESPONSES

PLAN GROUND STATION TRANSIT FOR THE TASKED SATELLITES FOR PAYLOAD DATA DOWNLOAD/ TTC BY THE MISSION CONTROL — 1510

1518

FAILURES

RESULT BACKEND RECEIVES RESPONSES BY TASK ID

ENQUEUE TASKS WITH PRIORITIES INTO A MASTER QUEUE BY THE MESSAGE BROKER — 1512

REFRESH FLIGHT DYNAMICS CALCULATIONS — 1514

1520A

TASKS ENQUEUED INTO WORKER1 QUEUES

1520B

TASKS ENQUEUED INTO WORKER2 QUEUES. ELSE, RETURN ON FAILURES

1520C

TASKS ENQUEUED INTO WORKER4 QUEUES

SIDECAR 1 1522A

SIDECAR 2 1522B

SIDECAR 4 1522C

GS2 RETURNS MP RESPONSES

GROUND STATION 1 FORWARDS COMMANDS 1524A

GROUND STATION 2 1524B

GROUND STATION 3 RETURNS MP2 RESPONSES 1524C

MA1, MP1 AND MA1 RESPONSE

GS2 FORWARDS MP2 COMMANDS

BEAM TO SAT1 EXECUTE TASK BY PRIORITY AND BEAM BACK RESPONSE/DATA 1526A

BEAM TO SAT2 EXECUTE TASK BY PRIORITY AND BEAM BACK RESPONSE / DATA TO 1526B

GROUND
TRACK

GS1

GS2

= AREA OF INTEREST
1704

= GROUND STATIONS
1702

- - - - - - - - - = 1706 CURRENT PATH

——— — = 1708 FUTURE PATH

ELEVATION PROFILE WITH COMMAND STATUS
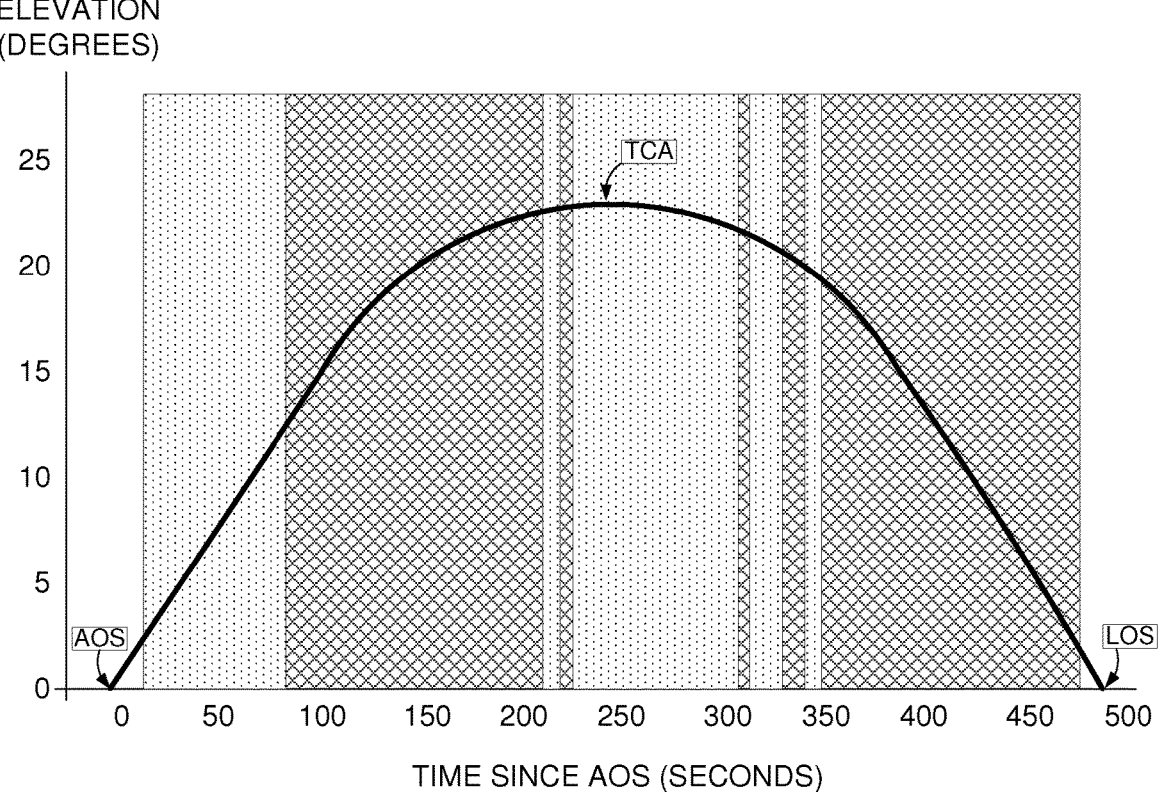
REGION 1
REGION 2
FIG. 19A

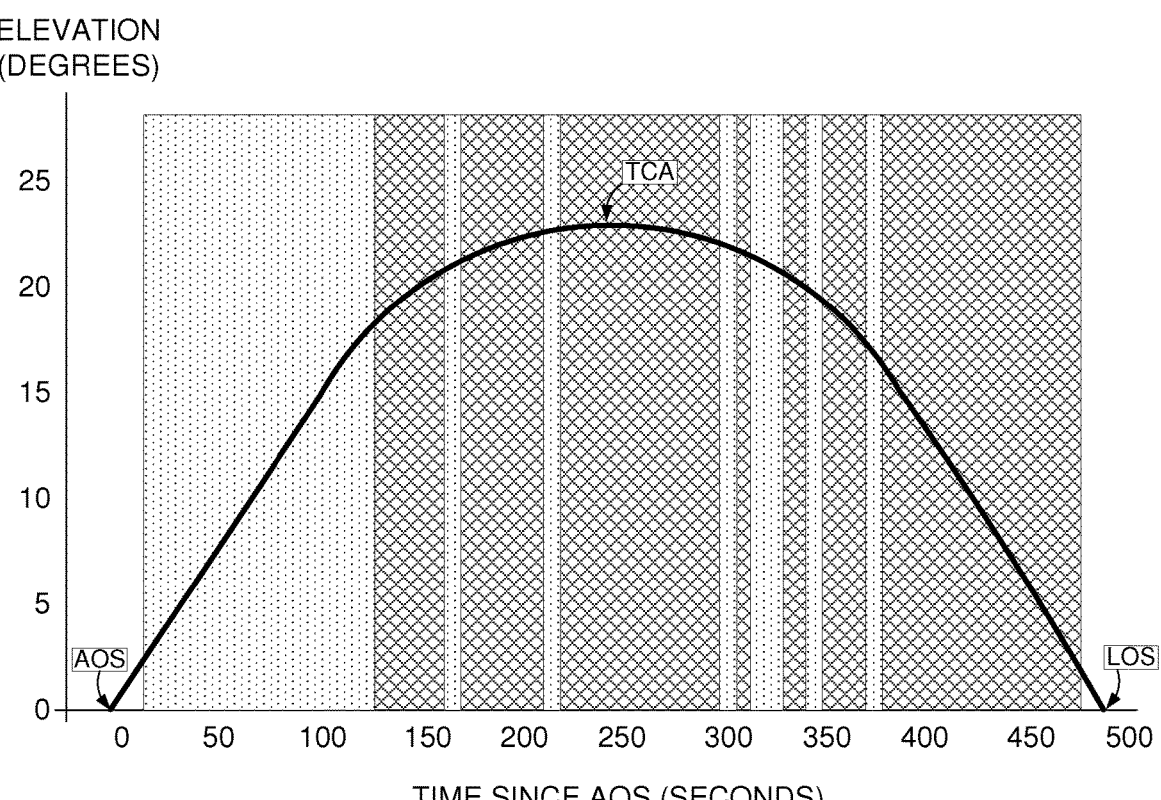
FIG. 19B

2000A

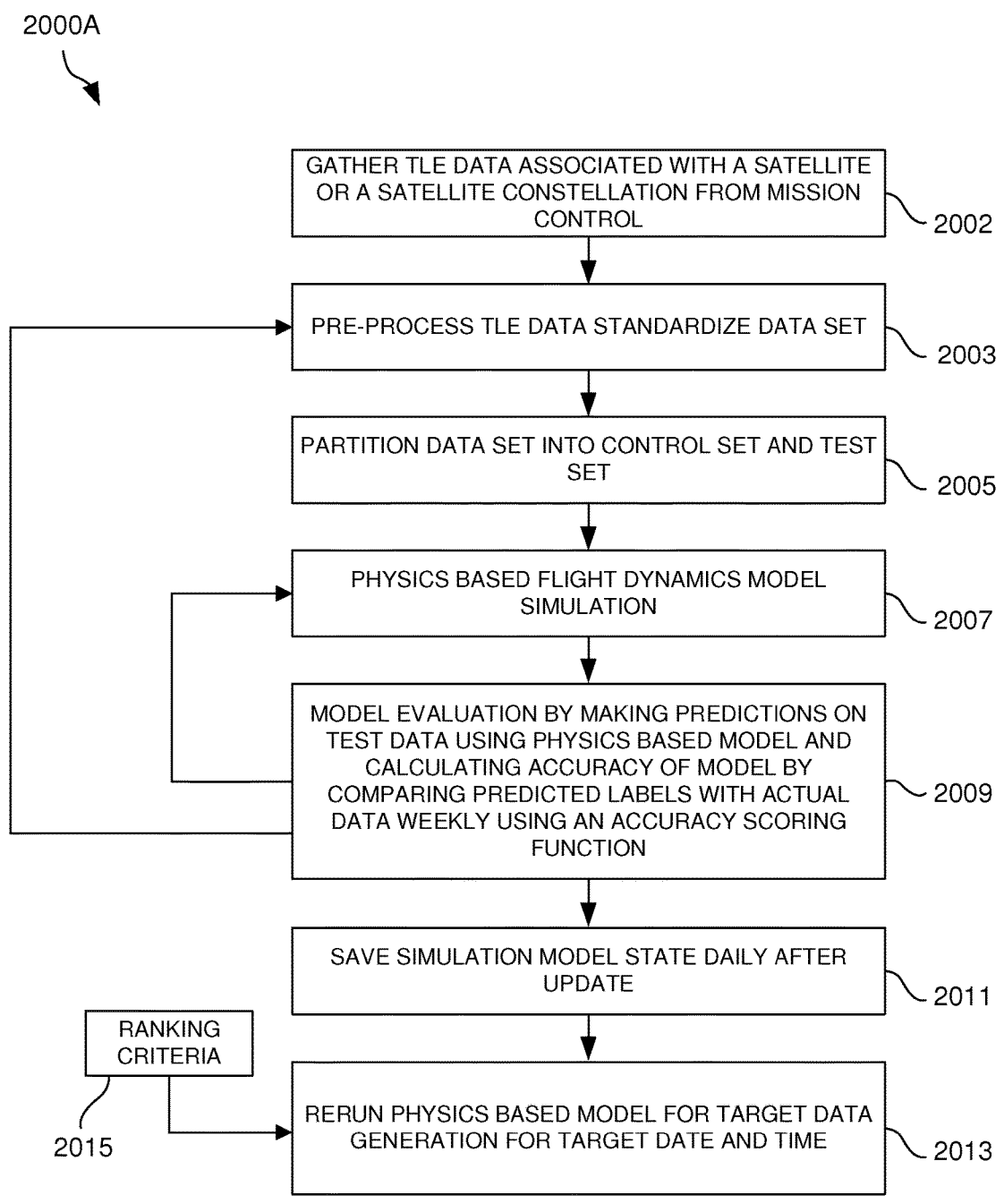

GATHER TLE DATA ASSOCIATED WITH A SATELLITE OR A SATELLITE CONSTELLATION FROM MISSION CONTROL — 2002

PRE-PROCESS TLE DATA STANDARDIZE DATA SET — 2003

PARTITION DATA SET INTO CONTROL SET AND TEST SET — 2005

PHYSICS BASED FLIGHT DYNAMICS MODEL SIMULATION — 2007

MODEL EVALUATION BY MAKING PREDICTIONS ON TEST DATA USING PHYSICS BASED MODEL AND CALCULATING ACCURACY OF MODEL BY COMPARING PREDICTED LABELS WITH ACTUAL DATA WEEKLY USING AN ACCURACY SCORING FUNCTION — 2009

SAVE SIMULATION MODEL STATE DAILY AFTER UPDATE — 2011

RANKING CRITERIA

2015

RERUN PHYSICS BASED MODEL FOR TARGET DATA GENERATION FOR TARGET DATE AND TIME — 2013

FIG. 20A

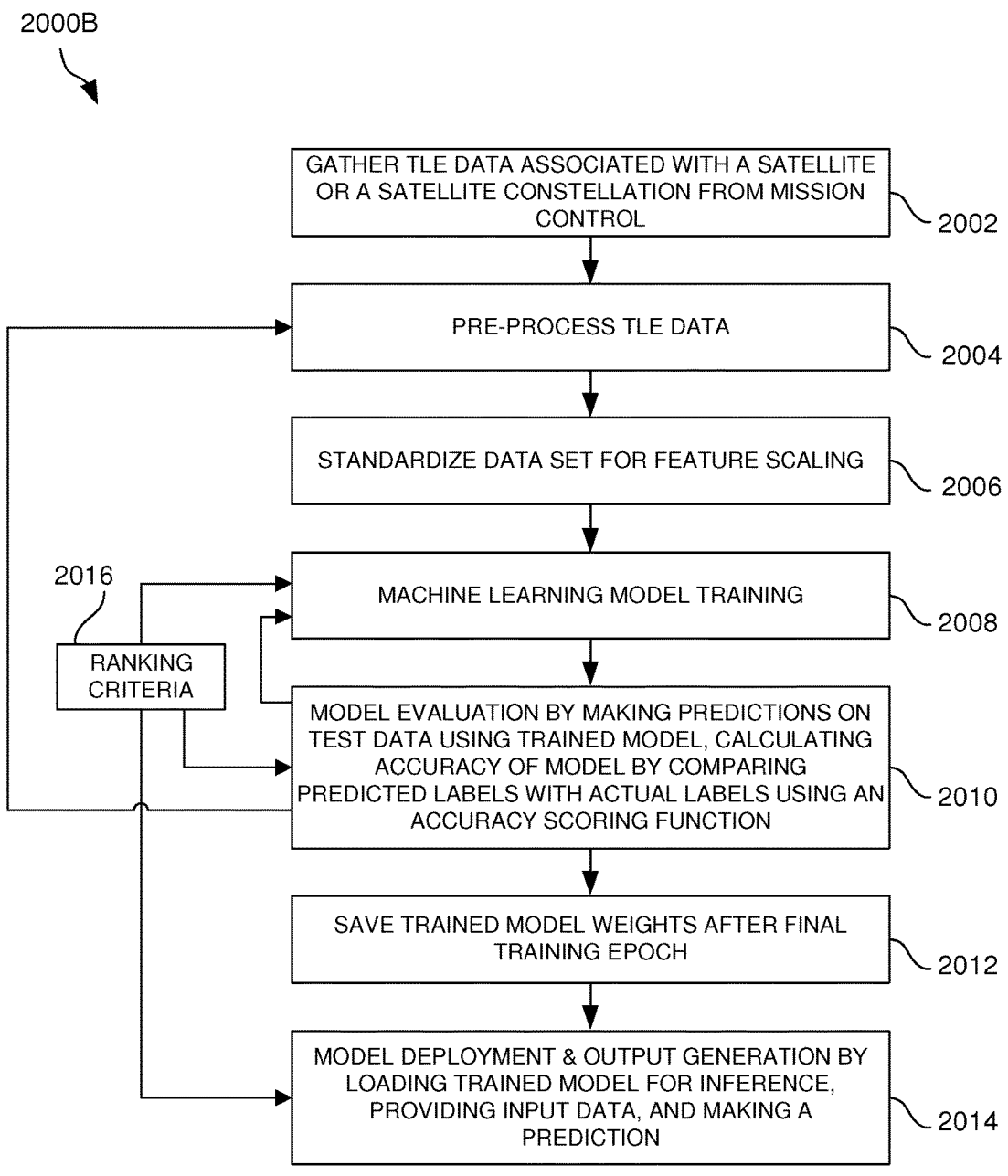

2000B

GATHER TLE DATA ASSOCIATED WITH A SATELLITE OR A SATELLITE CONSTELLATION FROM MISSION CONTROL — 2002

PRE-PROCESS TLE DATA — 2004

STANDARDIZE DATA SET FOR FEATURE SCALING — 2006

2016

RANKING CRITERIA

MACHINE LEARNING MODEL TRAINING — 2008

MODEL EVALUATION BY MAKING PREDICTIONS ON TEST DATA USING TRAINED MODEL, CALCULATING ACCURACY OF MODEL BY COMPARING PREDICTED LABELS WITH ACTUAL LABELS USING AN ACCURACY SCORING FUNCTION — 2010

SAVE TRAINED MODEL WEIGHTS AFTER FINAL TRAINING EPOCH — 2012

MODEL DEPLOYMENT & OUTPUT GENERATION BY LOADING TRAINED MODEL FOR INFERENCE, PROVIDING INPUT DATA, AND MAKING A PREDICTION — 2014

GND LOCATION AND DATE RANGE — 2202

ERROR COMPARISON

2203

GENERATIVE MACHINE LEARNING — 2204

GENERATED TLES OF HYPOTHETICAL TRANSITS OR PASSAGES — 2206

GND TRACKS — 2208

GENERATED LIST OF PASSAGES — 2210

CUSTOMER ORDER PARAMETERS

2218

PREDICTIVE MACHINE LEARNING — 2212

CANDIDATE TRANSITS / PASSAGES — 2214

MISSION PLANNING — 2216

2300

MISSION PLANNING / MISSION
ADMINISTRATION TRANSITS & PASSAGES
KNOWN AFTER RANKING — 2302

RULE BASED MACHINE LEARNING
RECOMMENDATION ENGINE — 2304

FLIGHT PARAMETERS AND/OR FLIGHT/TTC
COMMANDS PER PASSAGE — 2306

FAST DATA ENTRY USING ONE CLICK — 2308

COMMAND BATCHES — 2310

SEND TO REAL OR VIRTUAL SATELLITE — 2312

2400

2500

INTENT-BASED
SATELLITE
INSTRUCTION
2503

MACHINE
LEARNING
MODELS AND
PREDICTIVE
SATELLITE
TRANSIT
2505

EFFECTIVE
PAYLOAD
MANAGEMENT
2507

SATELLITE OPTIMIZATION MANAGEMENT SYSTEM BASED ON NATURAL LANGUAGE INPUT AND ARTIFICIAL INTELLIGENCE

CROSS-REFERENCE TO RELATED APPLICATIONS

This patent application claims the benefit of and priority to U.S. Provisional Patent Application No. 63/571,281, entitled "DISTRIBUTED SATELLITE CONSTELLATION MANAGEMENT AND CONTROL SYSTEM," filed Mar. 28, 2024; and U.S. Provisional Patent Application No. 63/574,141, entitled "DISTRIBUTED SATELLITE CON-STELLATION MANAGEMENT AND CONTROL SYS-TEM," filed Apr. 3, 2024, all of which are assigned to the assignee hereof; the disclosures of all prior Applications are considered part of and are incorporated by reference in this patent application.

This patent application is a continuation-in-part of and claims the benefit of and priority to U.S. patent application Ser. No. 18/600,486, entitled "DEEP GENERATIVE MOD-ELS FOR INVERSE DESIGN OF INORGANIC ATOM-ISTIC STRUCTURES," filed Mar. 8, 2024; and U.S. patent application Ser. No. 18/397,993, entitled "GENERATIVE ATOMISTIC DESIGN OF MATERIALS," filed Dec. 27, 2023, all of which are assigned to the assignee hereof; the disclosures of all prior Applications are considered part of and are incorporated by reference in this patent application.

FIELD OF THE INVENTION

The present disclosure generally relates to satellites, and more specifically, satellite constellation management and control.

BACKGROUND

Satellite constellations may include groups of satellites working together in a coordinated manner to provide global or near-global coverage for various applications such as communication, earth observation, and navigation. These constellations can range from a few satellites to hundreds or even thousands of satellites, depending on the specific application and coverage requirements.

Managing and controlling these satellite constellations can be a complex task due to the large number of satellites involved, the distance from a control point, and the dynamic and harsh space environment in which they operate. Such ability to control satellites typically may involve various aspects such as mission planning, satellite scheduling, communication management, and fault detection and recovery. However, current systems to control satellites are often confronting issues of delay (in delivering updates to satellite nodes), outdated infrastructure, lack of communication (such as when a satellite node exits a window of transmission), etc.

As such, there is thus a need for addressing these and/or other issues associated with the prior art.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

In some aspects, the techniques described herein relate to a satellite optimization management system, including: a natural language processing module configured to receive and interpret user input expressed in natural language to determine a user's intent and map it to specific tasks for a satellite, wherein the natural language processing module uses a neural network to determine the user's intent; an execution module configured to generate and execute satellite command sequences based on operational tasks derived from the user's intent; and a communication interface configured to facilitate data transmission between the satellite and ground control.

In some aspects, the techniques described herein relate to a satellite management system, including: a plurality one or more satellites in a constellation; a ground-based control system for managing operations of the one or more of satellites, the ground-based control system including satellite control and payload delivery systems, wherein the ground-based control system manages interaction between the one or more of satellites and at least one of: at least one ground station, at least one mission control station, or at least one data center; a messaging module configured to route messages between the one or more of satellites and the ground-based control system; and a micro-batch delivery module configured to transmit and receive the messages to and from the one or more of satellites.

In some aspects, the techniques described herein relate to an advanced mission control system, including: a ground-based satellite control system; a communication module for communicating between the ground-based satellite control system and one or more satellites; a satellite transit behavior prediction module configured to: receive current and past orbital transit paths of the one or more satellites, train a neural network based on the current and past orbital transit paths, and predict future orbital transit paths for the one or more satellites using the trained neural network; and a satellite management module for managing the one or more satellites based on the future orbital transit paths.

In some aspects, the techniques described herein relate to an intent-based satellite management system, including: one or more satellites in a constellation; a ground-based control system to manage the one or more satellites; a communication module configured to transmit intent-based instruction from the ground-based control system to the one or more satellites, wherein the intent-based instruction includes one or more predetermined outcomes; and an intent-based module, located on each satellite of the one or more satellites, configured to receive the intent-based instruction and instruct a processor to generate and execute command sequences in order to fulfill the intent-based instruction.

In some aspects, the techniques described herein relate to a satellite management system, further including a data processing module configured to analyze data collected by the one or more satellites and to provide feedback to the ground-based control system for adjusting future commands sent as micro-batch packets of data.

In some aspects, the techniques described herein relate to a satellite management system, further including a flight dynamics module for determining a correct Acquisition of Signal (AOS) and Loss of Signal (LOS) times for successful communication with the one or more satellites.

In some aspects, the techniques described herein relate to a satellite management system, further including a message broker of the messaging module, wherein the message broker is configured to route messages based on a location and availability of the plurality satellites in the constellation.

In some aspects, the techniques described herein relate to a satellite management system, further including a sidecar proxy of the micro-batch delivery module, wherein the sidecar proxy is configured to work with a send-queue and a receive-queue for messages to and from the one or more satellites using a secure database.

In some aspects, the techniques described herein relate to a satellite management system, further including a virtual satellite simulation infrastructure for creating new satellites to study what-if scenarios to pre-determine before-launch trajectories for new satellites of the one or more satellites or after-launch trajectories for existing satellites before a specific date.

In some aspects, the techniques described herein relate to a satellite management system, wherein the at least ground stations functions as the mission control station.

In some aspects, the techniques described herein relate to a satellite management system, wherein the at least one data center hosts a portion of a computing cloud and is further configured to provide storage of data and allow packetized transfer of the data.

In some aspects, the techniques described herein relate to a satellite management system, wherein the ground-based control system is configured to communicate with the satellites using micro-batching commands.

In some aspects, the techniques described herein relate to a satellite management system, wherein the ground-based control system is configured to provide fault tolerance by allowing remote rescheduling or reset of a satellite On-Board Computer (OBC) at another compliant ground station when at least one of the one or more satellites passes over the ground-based control system.

In some aspects, the techniques described herein relate to a satellite management system, wherein the micro-batch delivery module is configured to transmit micro-batch commands to the one or more satellites including instructions for at least one of: adjusting satellite positions, changing satellite orientations, or modifying operational parameters of the one or more satellites.

In some aspects, the techniques described herein relate to a satellite management system, wherein the micro-batch delivery module is further configured to optimize a timing and sequencing of data to or from the one or more satellites, wherein the sequencing of data includes segmenting the data into micro-batch packets of data.

In some aspects, the techniques described herein relate to a satellite management system, wherein the one or more satellites are equipped with sensors and instruments to perform data collection, imaging, or communication relay tasks in response to commands associated with the micro-batch packets of data.

In some aspects, the techniques described herein relate to a satellite management system, wherein the one or more satellites in the constellation are small satellites, wherein the small satellites are CubeSats.

In some aspects, the techniques described herein relate to a satellite management system, wherein the predetermined parameters include location, flight path, and times of Acquisition of Signal (AOS) and Loss of Signal (LOS) of the one or more satellites.

In some aspects, the techniques described herein relate to a satellite management system, wherein the satellite control and payload delivery systems are configured to segment the data based on a predictive model of satellite positions and operational requirements.

In some aspects, the techniques described herein relate to a satellite management system, wherein the virtual satellite simulation infrastructure is configured to simulate the trajectories of the one or more satellites based on predetermined parameters.

In some aspects, the techniques described herein relate to a satellite management system, wherein the virtual satellite simulation infrastructure is further configured to adjust the predetermined parameters based on real-time data received from the satellites.

In some aspects, the techniques described herein relate to a satellite optimization management system which uses an expert system coupled to and controlled by an intent-based processing system.

In some aspects, the techniques described herein relate to a satellite optimization management system, wherein the coarse-grained prediction includes workflow-based instructions pertaining to at least an entire orbit of the satellite, and the fine-grained prediction includes measurements to carry out the workflow-based instructions based on then-current information associated with the satellite.

In some aspects, the techniques described herein relate to a satellite optimization management system, wherein the communication interface includes a data compression system for optimizing the transmission.

In some aspects, the techniques described herein relate to a satellite optimization management system, wherein the communication interface includes a data encryption system for securing the transmission.

In some aspects, the techniques described herein relate to a satellite optimization management system, wherein the communication interface includes a data transmission error detection and correction system for detecting and correcting errors in the data transmission.

In some aspects, the techniques described herein relate to a satellite optimization management system, wherein the communication interface includes a data transmission logging system for logging the data transmission.

In some aspects, the techniques described herein relate to a satellite optimization management system, wherein the communication interface includes a data transmission monitoring system for monitoring the data transmission and providing feedback on the data transmission.

In some aspects, the techniques described herein relate to a satellite optimization management system, wherein the communication interface includes a data transmission protocol for managing the transmission.

In some aspects, the techniques described herein relate to a satellite optimization management system, wherein the communication interface includes a data transmission rate control system for controlling the rate of data transmission.

In some aspects, the techniques described herein relate to a satellite optimization management system, wherein the communication interface includes a data transmission scheduling system for scheduling the data transmission.

In some aspects, the techniques described herein relate to a satellite optimization management system, wherein the data compression system is configured to optimize a timing and sequencing of data to or from the satellite.

In some aspects, the techniques described herein relate to a satellite optimization management system, wherein the execution module includes a command generation system or command execution system for generating the satellite command sequences.

In some aspects, the techniques described herein relate to a satellite optimization management system, wherein the intent-based instructions are based on coarse-grained prediction and fine-grained in-flight measurements.

In some aspects, the techniques described herein relate to a satellite optimization management system, wherein the natural language processing module includes a speech recognition system for receiving voice-based user input.

In some aspects, the techniques described herein relate to a satellite optimization management system, wherein the natural language processing module includes a text analysis system for receiving text-based user input.

In some aspects, the techniques described herein relate to a satellite optimization management system, wherein the natural language processing module is configured to display a user interface to receive the user input.

In some aspects, the techniques described herein relate to a satellite optimization management system, wherein the neural network used by the natural language processing module is one of a recurrent neural network, or convolutional neural network.

In some aspects, the techniques described herein relate to a satellite optimization management system, wherein the sequencing of data includes segmenting the data into micro-batch packets of data.

In some aspects, the techniques described herein relate to a satellite optimization management system, wherein the user input includes unstructured text relating to intent-based instructions for the satellite.

In some aspects, the techniques described herein relate to a satellite optimization management system, wherein the user's intent is interpreted by the natural language processing module by at least one of tokenization, part-of-speech tagging, named entity recognition, stemming, lemmatization, sentiment analysis, syntax, or grammar.

In some aspects, the techniques described herein relate to an advanced mission control system, wherein the communication module is configured to optimize a timing and sequencing of data to or from the one or more satellites by segmenting the data into micro-batch packets of data.

In some aspects, the techniques described herein relate to an advanced mission control system, wherein the communication module uses radio frequency communication to communicate between the ground-based satellite control system and the one or more satellites.

In some aspects, the techniques described herein relate to an advanced mission control system, wherein the data processing module includes a data cleaning module for removing or correcting erroneous or missing data.

In some aspects, the techniques described herein relate to an advanced mission control system, wherein the data processing module includes a data normalization module for adjusting values of the satellite data to a common scale.

In some aspects, the techniques described herein relate to an advanced mission control system, wherein the data processing module includes a data transformation module for converting the satellite data into a suitable format or scale.

In some aspects, the techniques described herein relate to an advanced mission control system, wherein the ground-based satellite control system includes a data analysis module for analyzing satellite data.

In some aspects, the techniques described herein relate to an advanced mission control system, wherein the ground-based satellite control system includes a data mining module for mining satellite data.

In some aspects, the techniques described herein relate to an advanced mission control system, wherein the ground-based satellite control system includes a data processing module for preprocessing satellite data.

In some aspects, the techniques described herein relate to an advanced mission control system, wherein the ground-based satellite control system includes a data visualization module for visualizing satellite data.

In some aspects, the techniques described herein relate to an advanced mission control system, wherein the ground-based satellite control system includes a model training module for training machine learning models.

In some aspects, the techniques described herein relate to an advanced mission control system, wherein the ground-based satellite control system includes a user interface for managing operations of the one or more satellites.

In some aspects, the techniques described herein relate to an advanced mission control system, wherein the historical satellite transit data includes data related to orbital inclination, right ascension of an ascending node, eccentricity, argument of perigee, mean anomaly, and mean motion.

In some aspects, the techniques described herein relate to an advanced mission control system, wherein the machine learning model is trained using historical satellite transit data.

In some aspects, the techniques described herein relate to an advanced mission control system, wherein the model training module uses one of: a supervised learning model, an unsupervised learning model, a semi-supervised learning model, or a reinforcement learning model to train the machine learning models.

In some aspects, the techniques described herein relate to an advanced mission control system, wherein the satellite management module includes a scheduling module for scheduling satellite operations based on the future orbital transit paths.

In some aspects, the techniques described herein relate to an advanced mission control system, wherein the satellite transit behavior prediction module uses a machine learning model to predict the future orbital transit paths.

In some aspects, the techniques described herein relate to an advanced mission control system, wherein the segmenting is based on one or more areas of interest or a location of the ground-based satellite control system.

In some aspects, the techniques described herein relate to an advanced mission control system, wherein the segmenting is based on the future orbital paths.

In some aspects, the techniques described herein relate to an advanced mission control system, wherein the user interface includes a display for visualizing the current and future orbital transit paths of the one or more satellites.

In some aspects, the techniques described herein relate to an intent-based satellite management system, wherein the coarse-grained prediction includes workflow-based instructions pertaining to at least an entire orbit, and the fine-grained prediction includes measurements to carry out the workflow-based instructions based on then-current information associated with at least one satellite of the one or more satellites.

In some aspects, the techniques described herein relate to an intent-based satellite management system, wherein the command sequences are configured for future execution.

In some aspects, the techniques described herein relate to an intent-based satellite management system, wherein the command sequences are executed based on a schedule.

In some aspects, the techniques described herein relate to an intent-based satellite management system, wherein the command sequences are executed based on current and predicted future states of one or more of: a plurality of the satellite, a ground station, or a mission control station.

In some aspects, the techniques described herein relate to an intent-based satellite management system, wherein the command sequences are executed based on current and predicted future states of the satellite and the ground-based control system.

In some aspects, the techniques described herein relate to an intent-based satellite management system, wherein the command sequences are executed based on current and predicted future states of the satellite.

In some aspects, the techniques described herein relate to an intent-based satellite management system, wherein the command sequences are executed in real-time or near real-time.

In some aspects, the techniques described herein relate to an intent-based satellite management system, wherein the command sequences include flight dynamics commands.

In some aspects, the techniques described herein relate to an intent-based satellite management system, wherein the command sequences include payload delivery commands.

In some aspects, the techniques described herein relate to an intent-based satellite management system, wherein the command sequences include telemetry tracking and control (TTC) commands.

In some aspects, the techniques described herein relate to an intent-based satellite management system, wherein the intent-base instruction includes taking a predetermined action associated an area of interest.

In some aspects, the techniques described herein relate to an intent-based satellite management system, wherein the intent-based instruction includes a set of high-level goals for the one or more satellites.

In some aspects, the techniques described herein relate to an intent-based satellite management system, wherein the intent-based instruction includes an if-this-then-that configuration based on in-situ real-time measurements provided by any satellite of the one or more satellites.

In some aspects, the techniques described herein relate to an intent-based satellite management system, wherein the intent-based instruction is associated with a state of each satellite of the one or more satellites, and the command sequences are configured as real-time commands to achieve the state.

In some aspects, the techniques described herein relate to an intent-based satellite management system, wherein the intent-based instruction is based on coarse-grained prediction and fine-grained in-flight measurements.

In some aspects, the techniques described herein relate to an intent-based satellite management system, wherein the intent-based instruction is provided by a user through a user interface, wherein the user interface includes a natural language processing module for interpreting an intent of the user.

In some aspects, the techniques described herein relate to an intent-based satellite management system, wherein the intent-based module uses a neural network to generate the command sequences.

In some aspects, the techniques described herein relate to an intent-based satellite management system, wherein the intent-based module uses one of a deep learning model, a reinforcement learning model, a supervised learning model, an unsupervised learning model, or a semi-supervised learning model to generate the command sequences.

In some aspects, the techniques described herein relate to an intent-based satellite management system, wherein the natural language processing module uses a neural network to interpret the intent.

In some aspects, the techniques described herein relate to a rules-based expert system configured to create commands for any of the one or more pre-determined outcomes, the intent-based processing, and/or one or more actions implemented by a satellite.

The foregoing general description of the illustrative embodiments and the following detailed description thereof are merely exemplary aspects of the teachings of this disclosure and are not restrictive.

BRIEF DESCRIPTION OF THE DRAWINGS

FIG. 1B illustrates command-based and intent-based satellite instructions, in another embodiment.

FIG. 9A provides a UI/UX front-end for Mission Control and Flight Dynamics Software, in another embodiment.

FIG. 9B shows computing infrastructure for control of satellites, in another embodiment.

FIG. 10 shows an integrated simulation workspace for satellites, in another embodiment.

FIG. 15 shows a method for message passing, in another embodiment.

FIGS. 19A and 19B provide example scenarios for the elevation profile of a satellite in transit over a ground station, in another embodiment.

FIGS. 20A and 20B illustrate methods for gathering Two-Line Element (TLE) and mission control data to train a machine learning model, in another embodiment.

DETAILED DESCRIPTION

Figure 1A:
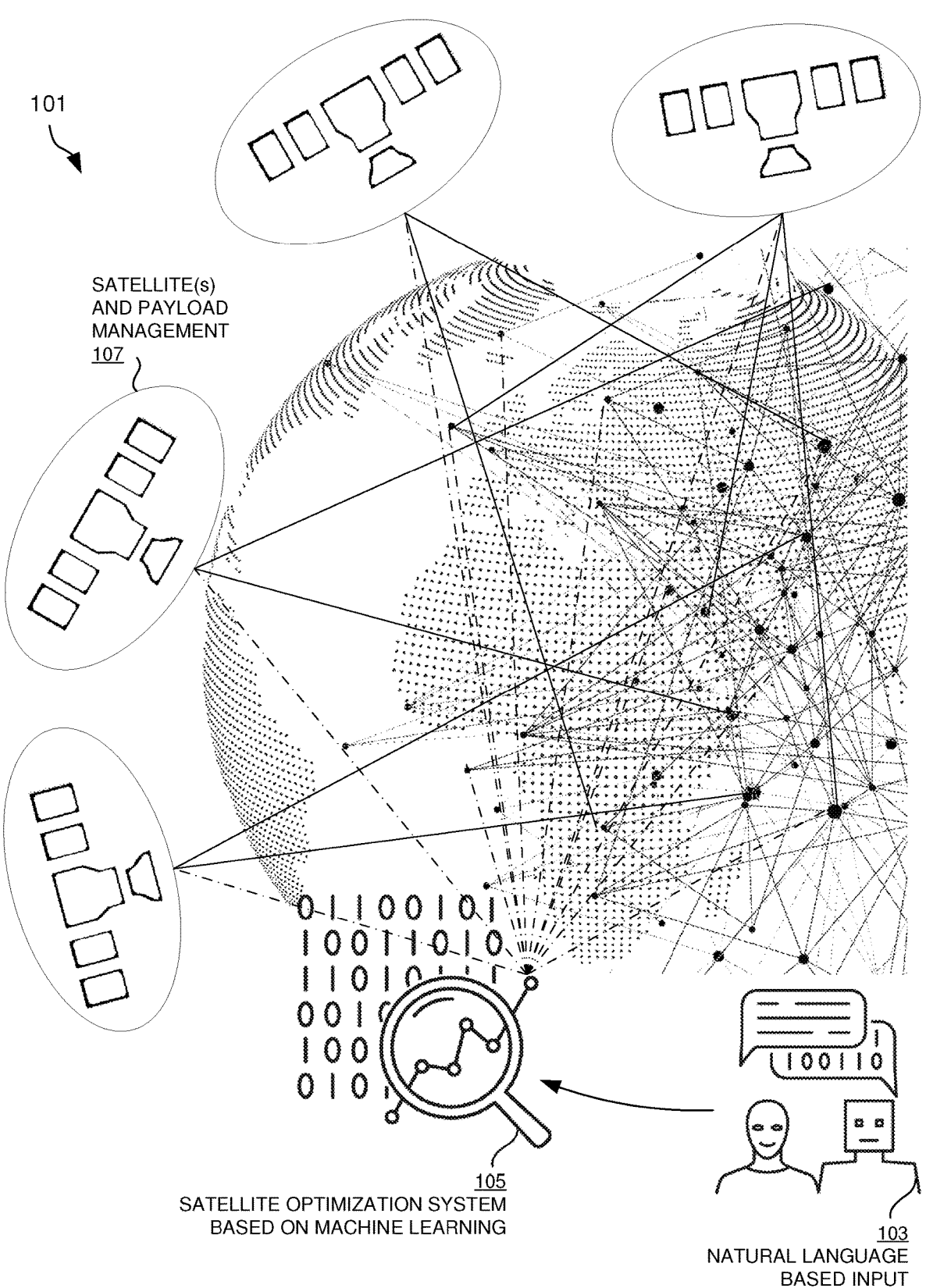
FIG. 1A illustrates satellite optimization management system based on natural language input and artificial intelligence, according to aspects of the present disclosure.

The following description sets forth exemplary aspects of the present disclosure. It should be recognized, however, that such description is not intended as a limitation on the scope of the present disclosure. Rather, the description also encompasses combinations and modifications to those exemplary aspects described herein.

The present disclosure pertains to the field of satellite constellation management and control, specifically focusing on systems, methods, and devices that facilitate distributed, scalable, and fault-tolerant management of satellite constellations. This may be achieved by leveraging modern distributed computing principles and technologies. In some aspects, the system comprises a constellation of satellites, one or more ground stations, a mission control station, and a data center hosting a portion of an internet cloud. The system may also include a message broker and send and receive queues for routing messages between the satellites, the ground stations, the mission control station, and the data center, and a sidecar proxy for communicating messages to and from the satellites.

In some cases, the satellites in the constellation may be small satellites, such as CubeSats. The message broker may be configured to route messages based on the location and availability of the satellites in the constellation. The sidecar proxy may work in conjunction with the send-queue and the receive-queue for messages to and from the satellites using a secure database. The system may also include a flight dynamics software for determining the correct Acquisition of Signal (AOS) and Loss of Signal (LOS) times for successful communication with the satellites. The mission control station may communicate with the satellites using micro-batching commands, and the data center hosting a portion of an internet cloud may provide storage of data and allow packetized transfer of data similar to the internet.

In some aspects, the system may provide fault tolerance by allowing remote rescheduling or reset of a satellite On-Board Computer (OBC) at another compliant ground station when the satellite passes over it. The system may also include a virtual satellite simulation infrastructure for creating new satellites to study what-if scenarios to predetermine the trajectories before launch for new satellites or the trajectories for existing satellites before a specific date. The virtual satellite simulation infrastructure may simulate one or more trajectories of the satellites based on predetermined parameters, which may include the location, flight path, and times of Acquisition of Signal (AOS) and Loss of Signal (LOS) of the satellites. The virtual satellite simulation infrastructure may further adjust the predetermined parameters based on real-time data received from the satellites.

This approach to satellite constellation management and control offers potential benefits such as increased efficiency, scalability, and fault tolerance, addressing some of the challenges associated with managing and controlling large numbers of satellites in a constellation.

A variety of benefits may be achieved by implementation of the framework and/or methods/systems disclosed herein, including: 1) increase speed of deployment (which may be achieved through standardized satellite infrastructure using on board computer(s)), 2) one click user interface (to control and/or manage satellite(s)), 3) accuracy of commands (which may be used to reduce human error and increase optimized commands sent in near real time), 4) case of use (via standardization of deployment such as of the Mission Control software platform), 5) decrease of cost (based in large part on the decrease in time to implement changes/management of satellites), and/or 6) reduced time of configuration (for example, an advertised life of a satellite may be only a few years, and configuration of the satellite may conventionally take a significant portion of such advertised life, whereas the present disclosure may reduce the time of configuration of the satellite, thereby maximizing an advertised life).

Definitions and Use of Figures

Some of the terms used in this description are defined below for easy reference. The presented terms and their respective definitions are not rigidly restricted to these definitions—a term may be further defined by the term's use within this disclosure. The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application and the appended claims, the term "or" is intended to mean an inclusive "or" rather than an exclusive "or". That is, unless specified otherwise, or is clear from the context, "X employs A or B" is intended to mean any of the natural inclusive permutations. That is, if X employs A, X employs B, or X employs both A and B, then "X employs A or B" is satisfied under any of the foregoing instances. As used herein, at least one of A or B means at least one of A, or at least one of B, or at least one of both A and B. In other words, this phrase is disjunctive. The articles "a" and "an" as used in this application and the appended claims should generally be construed to mean "one or more" unless specified otherwise or is clear from the context to be directed to a singular form.

Various embodiments are described herein with reference to the figures. It should be noted that the figures are not necessarily drawn to scale, and that elements of similar structures or functions are sometimes represented by like reference characters throughout the figures. It should also be noted that the figures are only intended to facilitate the description of the disclosed embodiments—they are not representative of an exhaustive treatment of all possible embodiments, and they are not intended to impute any limitation as to the scope of the claims. In addition, an illustrated embodiment need not portray all aspects or advantages of usage in any particular environment.

An aspect or an advantage described in conjunction with a particular embodiment is not necessarily limited to that embodiment and can be practiced in any other embodiments even if not so illustrated. References throughout this specification to "some embodiments" or "other embodiments" refer to a particular feature, structure, material or characteristic described in connection with the embodiments as being included in at least one embodiment. Thus, the appearance of the phrases "in some embodiments" or "in other embodiments" in various places throughout this specification are not necessarily referring to the same embodiment or embodiments. The disclosed embodiments are not intended to be limiting of the claims.

Ground stations may play a pivotal role in the management and control of satellite constellations. They serve as the primary interface between the satellites and the mission control center, facilitating the exchange of commands and data between them. The ground stations may be equipped with various types of equipment such as antennas, transceivers, and computers to enable this communication.

Mission control centers may be responsible for the overall management and control of the satellite constellations. They may be equipped with various types of software and hardware systems to perform tasks such as mission planning, satellite scheduling, data processing, and system monitoring. These centers typically may have a team of operators and engineers who monitor the status of the satellites and the constellation as a whole, and take appropriate actions as and when required.

Distributed computing principles and technologies, as applied to control of satellites, may enable the efficient and effective management of distributed systems by allowing the system components to work together in a coordinated manner, sharing resources and tasks, and providing fault tolerance and scalability.

Internet cloud technology may be used to provide for satellite control and/or management, thereby providing a scalable and flexible platform for hosting the various software and hardware systems involved in the management and control of satellite constellations.

Descriptions of Exemplary Embodiments

FIG. 1A shows a satellite optimization management system 101 based on natural language input and artificial intelligence, according to an embodiment. This system integrates advanced technologies based on natural language processing to streamline the management and control of satellite operations.

In operation, a natural language based input 103 may allow operators to manage and control satellite(s). Such a natural language based system may include a user-friendly interface to simplify the interaction between human operators and complex satellite systems, making it more accessible and efficient.

Within the context of the present description, natural language based input may include, but not be limited solely, to any form of communication that humans typically use. Such natural language may include colloquial terms, common phrases, everyday conversations, written expression, and/or thought conveyance. Additionally, natural language speech may encompass natural evolution of spoken writ, including languages spoken and written by people which may organically evolve within a community over time. As such, natural language speech may be characterized, in one embodiment, by its complexity, ambiguity, and/or the presence of cultural and contextual nuances.

It is recognized that understanding and processing natural language is a complex task for machines due to the intricacies, variations, and subtleties inherent in human communication. As such, machine learning may be adapted, in particular, to overcome such complexities, and may be configured to interact with, understand, and generate human language. See satellite optimization system based on machine learning 105. Such a system may be used to translate the natural language based input 103 into command sequence(s) to be implemented by one or more satellites.

It is to be appreciated that the command sequences may include explicit action-based commands and/or intent-based instruction, as discussed herein.

With respect to the processing of natural language, it is further recognized speech may be understood and interpreted using a variety of techniques to enable computers (including the machine learning systems) to comprehend, analyze, and generate human language. For example, such techniques may include tokenization (e.g. breaking down text into smaller units or tokens, facilitates subsequent analysis), part-of-speech tagging (e.g. assign grammatical categories to each word, aiding in understanding sentence structures), named entity recognition (e.g. identify and classify names, locations, and dates associated with the words, enabling the extraction of structured information), stemming and lemmatization (e.g. reduce words to their base form), sentiment analysis (e.g. understanding of emotional tone in the text), syntax and grammar analysis (e.g. provide understanding relationships between words), etc. As such, it is recognized and understood that a variety of methods may be used to interpret and process natural language text.

It is to be appreciated that the system 101 may include a text-to-satellite inference method where an inference of the intent may interpreted into satellite commands and/or actions. For example, the natural language based input 103 may include receiving a text prompt from a user wherein the text prompt is in the form of unstructured text requesting a satellite action and/or a specific task. Additionally, the natural language based input 103 may include processing the text prompt by a large language model that converts the text into a numerical representation of the text prompt, and may include providing an generative model (i.e. including but not limited to large language models, or atomistic generative models, or auto encoders, or transformers, or other generative machine learning models, etc.) with the numerical representation of the text prompt. Further, the text-to-satellite inference may include an expert system trained by mission experts that may be used to automatically create commands designed to control and/or communicate with a satellite.

In various embodiments, the large language model may be implemented in a neural network architecture, convolutional neural network, parameterized network system, rule-based system, or ensemble network system. Additionally, the unstructured text lacks a predefined structure or format, and/or the text prompt may include at least one of natural-language text string or an alphanumeric text string.

Further, the command sequences may be transmitted to satellites for satellite and payload management 107. Satellite and payload management 107 may include transmission from a ground-based control station to one or more satellites based on an output from the satellite optimization system based on machine learning 105. Additionally, the satellite and payload management 107 may include efficient transmission of payload (including micro-batch packet delivery) to one or more ground-based control stations (in a coordinated manner).

In some aspects, the techniques described herein relate to a satellite optimization management system, which may include a natural language processing module configured to receive and interpret user input expressed in natural language to determine a user's intent and map it to specific tasks for a satellite. The natural language processing module may use a neural network to determine the user's intent. Additionally, the system may include an execution module configured to generate and execute satellite command sequences based on the operational tasks derived from the user's intent, and a communication interface configured to facilitate data transmission between the satellite and ground control.

In various embodiments, the natural language processing module may include a speech recognition system for receiving voice-based user input, and/or a text analysis system for receiving text-based user input. Additionally, the neural network used by the natural language processing module may be one of a recurrent neural network, and/or convolutional neural network. The user's intent may be interpreted by the natural language processing module by at least one of tokenization, part-of-speech tagging, named entity recognition, stemming, lemmatization, sentiment analysis, syntax, or grammar.

In various embodiments, the execution module may include a command generation system and/or command execution system for generating the satellite command sequences. Additionally, the natural language processing module may be configured to display a user interface to receive the user input, and the user input may include unstructured text relating to intent-based instructions for a satellite.

In various embodiments, the intent-based instructions may be based on coarse-grained prediction and fine-grained in-flight measurements. Additionally, the coarse-grained prediction may include workflow-based instructions pertaining to at least an entire orbit of the satellite, and the fine-grained prediction may include measurements to carry out the workflow-based instructions based on then-current information associated with the satellite.

In various embodiments, the communication interface may includes a data compression system for optimizing the transmission, and the data compression system may be configured to optimize the timing and sequencing of data to or from the satellite. The sequencing of data may comprise segmenting the data into micro-batch packets of data.

In various embodiments, the communication interface may include or more of a data transmission protocol for managing the transmission, a data transmission rate control system for controlling the rate of data transmission, a data transmission error detection and correction system for detecting and correcting errors in the data transmission, a data transmission scheduling system for scheduling the data transmission, a data transmission logging system for logging the data transmission, a data transmission monitoring system for monitoring the data transmission and providing feedback on the data transmission, and/or a data encryption system for securing the transmission.

In one embodiment, the techniques described herein relate to a distributed satellite management system, including one or more satellites in a constellation, and a ground-based control system for managing operations of the one or more satellites, the ground-based control system including satellite control and payload delivery systems, where the ground-based control system manages interaction between the one or more satellites and at least one of: at least one ground station, at least one mission control station, or at least one data center. Additionally, the system may include a messaging module configured to route messages between the one or more satellites and the ground-based control system, and a micro-batch delivery module configured to transmit and receive the messages to and from the one or more satellites.

In various embodiments, the micro-batch delivery module may be further configured to optimize the timing and sequencing of data to or from the one or more satellites, where the sequencing of data comprises segmenting the data into micro-batch packets of data. Additionally, the satellite control and payload delivery systems may be configured to segment the data based on a predictive model of satellite positions and operational requirements. Further, the one or more satellites may be equipped with sensors and instruments to perform data collection, imaging, or communication relay tasks in response to commands associated with the micro-batch packets of data.

In various embodiments, a data processing module may be included and configured to analyze data collected by the one or more satellites and to provide feedback to the ground-based control system for adjusting future commands sent as micro-batch packets of data. The micro-batch delivery module may be configured to transmit micro-batch commands to the one or more satellites including instructions for at least one of: adjusting satellite positions, changing satellite orientations, or modifying operational parameters of the one or more satellites. The one or more satellites in the constellation may be small satellites, where the small satellites may include CubeSats. Additionally, the messaging module may include a message broker which may be configured to route messages based on a location and availability of a satellite in the constellation. Further, the micro-batch delivery module may include a sidecar proxy configured to work with the send-queue and the receive-queue for messages to and from the one or more satellites using a secure database.

In various embodiments, the system may include a flight dynamics module for determining the correct Acquisition of Signal (AOS) and Loss of Signal (LOS) times for successful communication with the one or more satellites. The ground-based control system may be configured to communicate with the satellites using micro-batching commands. Additionally, the at least one data center may host a portion of the computing cloud and may be further configured to provide storage of data and allow packetized transfer of the data. The ground-based control system may be configured to provide fault tolerance by allowing remote rescheduling or reset of a satellite On-Board Computer (OBC) at another compliant ground station when at least one of the one or more satellites passes over a first of the one or more ground stations. It is to be appreciated that the reset of a satellite may be tied to a particular satellite (e.g. Satellite X needs to be reset and a command is given specific to Satellite X to reset, etc.).

In various embodiments, a virtual satellite simulation infrastructure may be included for creating new satellites to study what-if scenarios to pre-determine the trajectories before launch for new satellites of the one or more satellites or the trajectories for existing satellites before a specific date. The virtual satellite simulation infrastructure may be configured to simulate the trajectories of the one or more satellites based on predetermined parameters. Additionally, the predetermined parameters may include the location, flight path, and/or times of Acquisition of Signal (AOS) and Loss of Signal (LOS) of the one or more satellites. The virtual satellite simulation infrastructure may be further configured to adjust the predetermined parameters based on real-time data received from the satellites. Further, the at least one ground stations may function as the mission control station.

It is to be appreciated that the system 101 displays a distribute network of ground resources and satellites, a multi-path fault-tolerant network, and/or smart-batching capabilities of the system.

Some types of satellite management systems involve issuing instructions that are optimally carried out in a future timeframe. Aspects of such instructions rely on accurate prediction, and accurate prediction relies on models that are both accurate and precise. An enormous amount of research and development effort has been applied to making models accurate and precise, however such models have not kept pace with the accuracy and precision needed for various critical satellite management functions (e.g., precise correlation of satellite positions with respect to multi-frame image capture, or precise correlation of satellite positions with respect to upload/download events). Virtually all of the efforts to ameliorate these deficiencies have relied on improvement of models. Unfortunately, models however well conceived and implemented will never be able to predict stochastic events that happen in space (e.g., encounters with space junk or other gravitational perturbations). As such, a different approach needs to be taken.

There needs to be some way to combine satellite behavior prediction with actual real-time in-situ information. That is, there needs to be both, a technique to combine model-based "coarse-grained" predictions of satellite behavior and techniques for actual real-time "fine-grained" in-flight measurements. Such a combination enables highly accurate and precise satellite command and control (e.g., based on the combination of coarse-grained predictions and "fine-grained" in-flight measurements that inform then current state traversal).

More specifically, one way to combine is to use (1) coarse-grained predictions to generate workflow-based instructions (e.g., pertaining to a long-running workflow that covers an entire orbit or more) and then to use (2) actual real-time "fine-grained" in-flight measurements to carry out those workflow-based instructions based on then-current information. In order to accomplish the foregoing, commands are delivered to the satellite as "intents". That is, rather than issuing a command like "start collecting data when the satellite's position is at <longitude, latitude, altitude>" an intent-based instruction may be sent, such as, "start collecting data when the satellite is in clear view of a particular terrestrial station". As can now be understood, this combination of (1) using coarse-grained predictions for delivering intents to a satellite, and then (2) using the satellite's in-situ, real-time measurement facilities to carry out operations based on then-current conditions to achieve the intents' demands coordination between the ground stations and the satellite. Moreover, the satellite must be equipped with one or more forms of an "intent processor" that takes in an intent specification in the form of a set of to-be-achieved states, and then, in a future time and based on the given to-be-achieved states, the satellite's intent processor generates low-level, real-time commands that do achieve the intents in a manner that is both accurate and precise.

With this context in place, therefore, the command-based satellite instructions 109A of FIG. 1B shows commands sent for future execution 111. Such commands may be sent from a ground station, and/or any earth-based system. Additionally, any number of commands (shown as Command C1—Command C3) may be sent to a satellite when it is in communication with the ground station (shown in current position 113). As the satellite moves (via passage 115), it seeks to implement the commands provided via the future flyover period 117. Such commands (per the commands sent for future execution 111) are static, in the sense that once they are sent by a ground station (or ground-based system), they are executed accordingly by the satellite as dictated and instructed.

In contrast, the intent-based satellite instructions 109B of FIG. 1B shows intents sent for future execution 121. Such instructions may be sent from a ground station, and/or any earth-based system. Additionally, any number of intents (shown as Intent I1-Intent I3) may be sent to a satellite when it is in communication with the ground station (shown in current position 113). As discussed herein, intent-based instructions may be based on coarse-grained predictions and actual real-time fine-grained in-flight measurements. As the satellite moves (via passage 115), an intent processor 123B may be used by the satellite to implement the appropriate commands that conform to the intent-based instruction originating from a ground station. In one embodiment, the ground station may include an intent processor 123A that may receive intent based instruction from a user. Such intent based instruction may be received by the intent processor 123A and implemented at a later time period by the intent processor 123B.

Thus, in one example, an intent-based instruction may indicate that when a satellite is over a specific (longitude and latitude) predetermined area of interest, and if the cloud cover is clear, to then take a predefined number of images. Thus, at the future flyover period 117, when the satellite is at a future position2, the intent processor 123B may first determine that the satellite is nearing the coarse-grained predicted location, and may use actual real-time fine grained in-flight measurements to determine when the satellite's position corresponds with the specific predetermined area of interest. The intent processor 123B may further determine if the cloud cover at the specific predetermined area of interest conforms with the intent-based instruction (namely whether it is clear). Having satisfied such conditions, the intent processor 123B may then execute instructions to capture images accordingly. This intent-based processing may include a determination of compliance (shown as state transversal under then current conditions 125) with the intent-based instructions by the intent processor 123B.

It is to be appreciated that any number and any form of intent-based instructions may be sent to the satellite. Thus, the intent-based instructions may relate to if-then type conditions that must be satisfied before a predetermined action is taken. Additionally, in another embodiment, the intent-based instructions may relate to satellite configuration and/or manipulation, such that the satellite is modified in real-time (orientation of satellite (including pitch, yaw, and roll adjustments including change in gyroscope configurations), change in orbital altitude, change in orbital inclination, change in orbit circularization, change in orbit transfer, change in orbital maintenance, etc. As such, the intent processor 123B may not only satisfy a compliance requirement, but may also be used to change one or more aspects of the movement of the satellite in order to have the satellite conform with the intent-based instruction provided. As one other example, an intent-based instruction may be given to photograph a predetermined area of interest. Upon nearing such area of interest, the intent processor 123B may determine that the trajectory of the satellite (using fine-grained in-flight measurements) will be over the specified area of interest at a precise time. The intent processor 123B may determine (based on the fine-grained in-flight measurements) that the satellite will not be optimized (in terms of attitude and angle of position) for the area of interest, and may therefore change the trajectory (using fine-grained changes) to maximize the capture of photos at the area of interest. In this manner, therefore, the intent processor 123B may be used to execute intent-based commands (including instruction from the intent processor 123A), and control the satellite to maximize the fulfillment of the intent-based commands. Further, in some embodiments, intents may be processed at mission control or any of the ground-stations, or at other ground locations on the network and converted into command batches that may be sent to the satellite as in FIG. 1B.

Figure 1C:
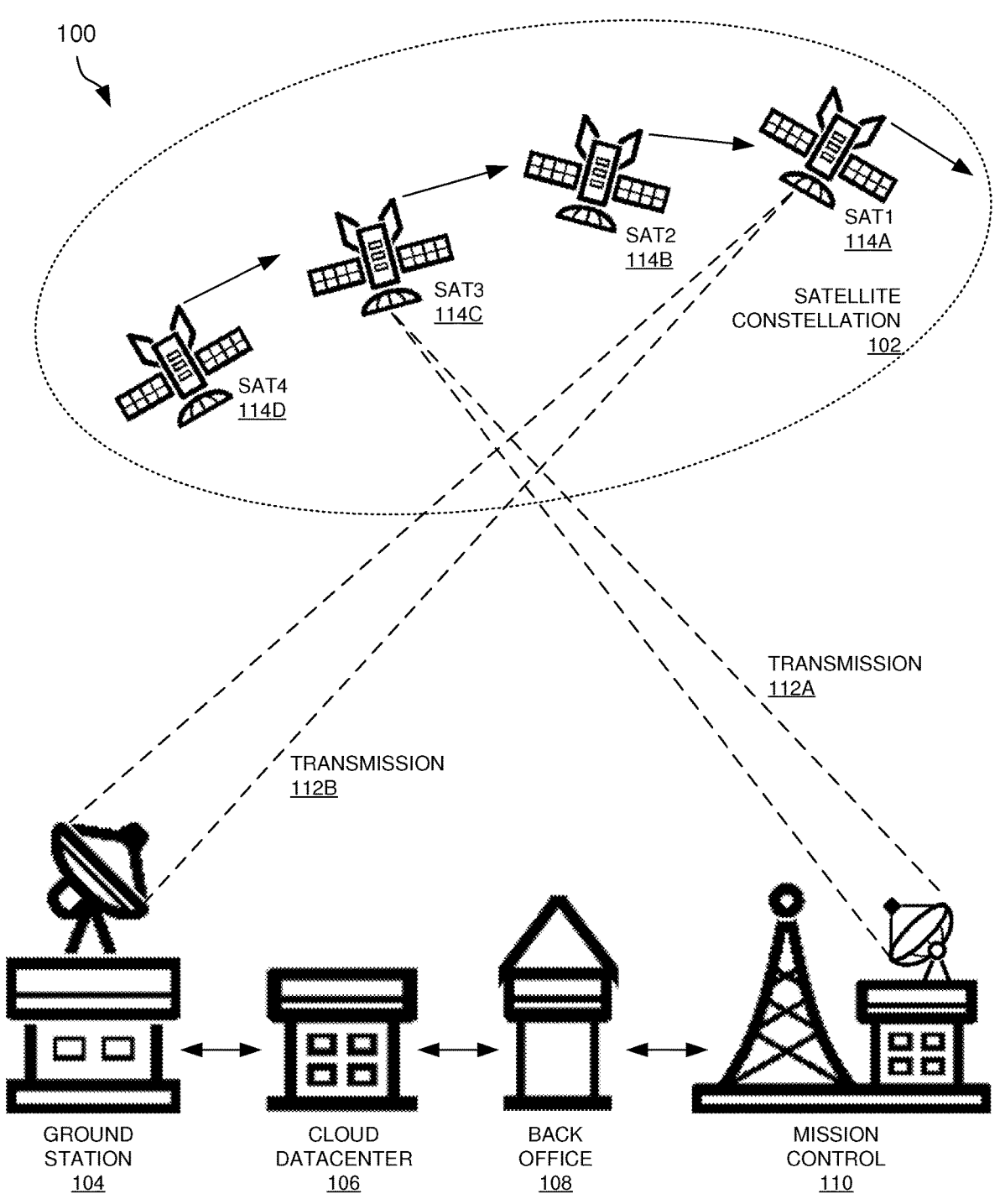
FIG. 1C illustrates a distributed system comprising satellites in a constellation, ground-stations, mission control, back-office(s), and datacenters, in another embodiment.

FIG. 1C illustrates a distributed system 100 comprising satellites in a constellation, ground-stations, mission control, back-office(s), and datacenters, according to aspects of the present disclosure. As an option, FIG. 1C may be implemented in the context of any one or more of the embodiments set forth in any previous and/or subsequent figure(s) and/or description thereof. Of course, however, FIG. 1C may be implemented in the context of any desired environment. Further, the aforementioned definitions may equally apply to the description below.

In some aspects, the distributed satellite constellation management and control system may comprise one or more satellites in a constellation 102. These satellites may include, but not be limited solely to, small satellites, such as Cube-Sats, in some cases. The system may also include one or more ground station(s) 104, mission control station(s) 110, and a cloud datacenter 106 hosting a portion of an internet cloud.

In some embodiments, the system may include a message broker. The message broker may be configured to route messages between the satellites, the ground station(s) 104, the mission control station(s) 110, and the cloud datacenter 106. The routing of messages may be based on the location and availability of one or more of the satellites 114A-114D in the constellation 102 in some cases.

The system may also include a sidecar proxy in some embodiments. In some embodiments, sidecar proxies may serve as ground interfaces for satellites, may encrypt and/or decrypt messages, and may work in conjunction with a send-queue and a receive-queue for messages to and from the satellites. The send-queue and the receive-queue may be maintained using a secure database in some cases.

In some aspects, the system may provide fault tolerance by allowing remote rescheduling or reset of a satellite On-Board Computer (OBC) at another compliant ground station when the satellite passes over it. The system may also include a virtual satellite simulation infrastructure for creating new satellites to study what-if scenarios to predetermine the trajectories before launch for new satellites or the trajectories for existing satellites before a specific date.

The virtual satellite simulation infrastructure may simulate one or more trajectories of the satellites based on predetermined parameters, which may include the location, flight path, and times of Acquisition of Signal (AOS) and Loss of Signal (LOS) of the satellites. The virtual satellite simulation infrastructure may further adjust the predetermined parameters based on real-time data received from the satellites in some cases.

This approach to satellite constellation management and control offers potential benefits such as increased efficiency, scalability, and fault tolerance, addressing some of the challenges associated with managing and controlling large numbers of satellites 114A-114D in a constellation 102.

In various embodiments, a distributed system may comprise one or more satellites in a constellation (such as SAT1 114A-SAT4 114D), one or more ground-station(s) 104, mission control 110, one or more back-office(s) 108, and/or one or more cloud datacenter(s) 106 hosting a portion of the internet cloud, the cloud being a public internet segment, a private intranet, etc.

Further, similar to modern distributed computing, the satellite configuration may be scaled from, for example, one satellite node to 100s of satellite nodes by few lines of code changes. For example, new satellite nodes may be added to a satellite constellation (such as the constellation 102), including when new satellites are launched. Configuring the new satellite nodes may additionally require minimal additional software. For example, each satellite node may include a beacon, a NORAD ID (e.g. which can be programmed to identify the satellite), software to enable Machine Message Queue Telemetry Transport (MQTT), and/or other protocol identification or other addresses or identifiers.

It is to be understood, that a portion of code can run either on a ground device, and/or an edge device, including but not limited to the satellite or a constellation 102 of satellites. Additionally, each satellite may include, but not be limited to, an onboard computer (OBC) and/or DSP (digital signal processor). Such satellites 114A-114D may be in direct communication via the transmission 112A and/or 112B with one or more of the ground station(s) 104, the mission control 110, etc. and indirectly in communication (via an intermediary node such as the ground station(s) 104 and/or the mission control 110) with the cloud datacenter 106 and/or the back-office 108.

More illustrative information will now be set forth regarding various optional architectures and uses in which the foregoing method may or may not be implemented, per the desires of the user. It should be strongly noted that the following information is set forth for illustrative purposes and should not be construed as limiting in any manner. Any of the following features may be optionally incorporated with or without the exclusion of other features described.

Figure 2:
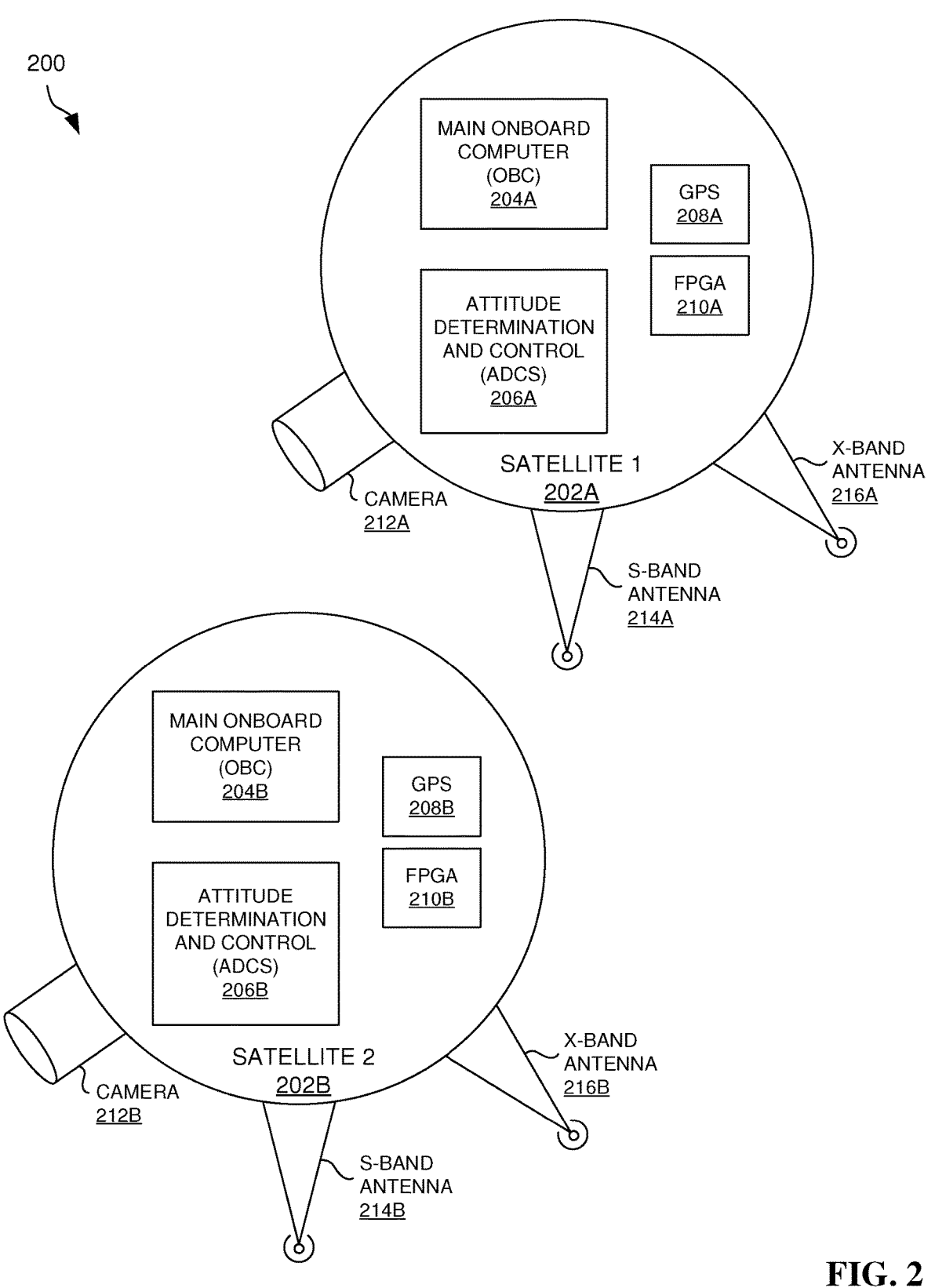
FIG. 2 depicts a satellite as a node in a distributed system, in another embodiment.

FIG. 2 illustrates a depiction 200 of a satellite as a node in a distributed system, in another embodiment. As an option, FIG. 2 may be implemented in the context of any one or more of the embodiments set forth in any previous and/or subsequent figure(s) and/or description thereof. Of course, however, FIG. 2 may be implemented in the context of any desired environment. Further, the aforementioned definitions may equally apply to the description below.

In some aspects, a satellite (Satellite 1 202A and/or Satellite 2 202B) may be represented as a node in a distributed system. It is to be understood that although the below description may be in reference to a particular satellite (such as the satellite 1 202A), such description may apply equally to one or more of other satellites as well. This node may be associated with specific ports of specific addresses in the distributed system. The satellite 202A, 202B node may include one or more On-Board Computers (OBCs) 204A, 204B residing on these specific ports. The OBCs 204A, 204B may be responsible for controlling and managing various operations of the satellite 202A, 202B, such as communication, navigation, and payload management.

In some cases, the satellite node may host re-programmable resources such as one or more Field Programmable Gate Arrays (FPGAs) 210A, 210B coupled to one or more ports associated with the satellite 202A, 202B. These FPGAs 210A, 210B may be programmed using the OBC 204A, 204B to pre-process, compress, or encrypt data from one or more resources on board the satellite. This may allow for enhancement and expansion of the functionality of the satellite 202A, 202B to maintain compatibility with newer models of the satellites in a constellation.

In some embodiments, the satellite node may also include various other resources such as camera(s) 212A, 212B, X-Band antenna(s) 216A, 216B, S-Band antenna(s) 214A, 214B, other antennas, GPS 208A, 208B, other sensors, and other equipment. These resources may be available on specific ports of the node that is the satellite. This configuration allows for efficient and effective management of the satellite resources and operations in the distributed system. Further, the satellite node may include attitude determination and control (ADCS) 206A, 206B to assist with controlling the satellite (including flight parameters, angle, speed, etc.).

In some aspects, the satellite node may also include a sidecar proxy for working with a send-queue and a receive-queue for messages to and from at least one satellite with a ground station. In some embodiments, sidecar proxies may serve as ground interfaces for satellites, may encrypt and/or decrypt messages, and may work in conjunction with a send-queue and a receive-queue for messages to and from the satellites. This allows for secure and efficient communication between the satellite and other nodes in the distributed system, such as ground stations, mission control stations, and datacenters. In one embodiment, the sidecar may be a separate discrete component of the satellite 202A, 202B, and/or may be included as a function of an existing component (such as of the OBC 204A, 204B).

In other embodiments, a satellite may function as a node in a distributed system. The satellite may include On-Board Computers 204A, 204B residing on specific ports of specific addresses in the Distributed System. The resources on the satellite 202A, 202B such as for e.g., a Camera 212A, 212B, an S-Band Antenna 214A, 214B, X-Band Antenna 216A, 216B, etc. may be available on specific ports of the node (e.g. Satellite 1 202A, Satellite 2 202B).

Further, encrypted Communication with Resources in the Distributed System of Satellites and Ground Stations may be required and may be achieved using Sidecar Proxies. It is to be understood that a sidecar proxy may be a dedicated component deployed alongside each microservice to handle a variety of issues (e.g. logging, security, monitoring, etc.). It may be used to intercept and manages inbound and outbound traffic to the microservice, providing a variety of functionalities, such as but not limited to load balancing, routing, security, encryption, authentication, logging, monitoring, etc.

A satellite may host re-programmable resources such as one or more FPGAs 210A, 210B coupled to one or more ports associated with the satellite(s) 202A, 202B. Hardware functions that were not implemented before the time of launch may be programmed into the FPGA 210A, 210B using the OBC 204A, 204B to pre-process or compress or encrypt data from one or more resources on board the satellite(s) 202A, 202B to allow for enhancement and expansion of the functionality of the satellite to maintain compatibility with newer models of the satellites in a constellation.

In one embodiment, a satellite may be assigned a desired state, and such state may be translated into a set of preconfigured operations. TLS 2.0 or TLS 3.0 may be used with each satellite in a constellation for communication, and public and private keys may be used to communicate with a satellite for encrypted communication using AES-256 or DES or any other encryption mechanism. Providing new keys or key changes or key rotations may be performed for the satellites as communicating nodes. Public key Infrastructure (PKI) mechanisms may be implemented in satellites to allow key rotation, etc. All these actions can be done using a declarative infra structure. As such, various options may be implemented to protect the integrity (security) of the satellite node.

For example, infrastructure as code and/or policy as code may help to ensure that a security posture (of the satellite and/or satellite constellation) is consistent and enforceable across a variety of environments.

It is to be understood that such configuration of satellite nodes may allow for minimal pre-processing operations (for configuring code) such that a variety of functions (sensor calibration, atmospheric correction, radiometric calibration, noise to signal processing, remote sensing) may occur as needed without complicated coding of each satellite node.

Further, automated security scanning may occur such that declarative configurations may be analyzed automatically by security tools to ensure the satellite (or constellation of satellites) meets predetermined security standards. This automated scanning may identify misconfigurations or policy violations before the satellite(s) are deployed.

With respect to compliance, it is to be understood that any change in compliance may be proliferated immediately using the declarative infrastructure to all the nodes, including but not limited to satellites, ground stations, mission control, etc. In various embodiments, a command (originated from a human and/or ground control center) may be broken into multiple commands, and in turn, micro-batching (as described in further detailed hereinbelow) may be used to send the commands to individual satellites. Further, compliance as code may be embedded into each satellite to facilitate management once deployed.

As such, this approach in managing security and encryption for satellite(s) allows for a more consistent, auditable, and automated way of enforcing security policies.

Figure 3:
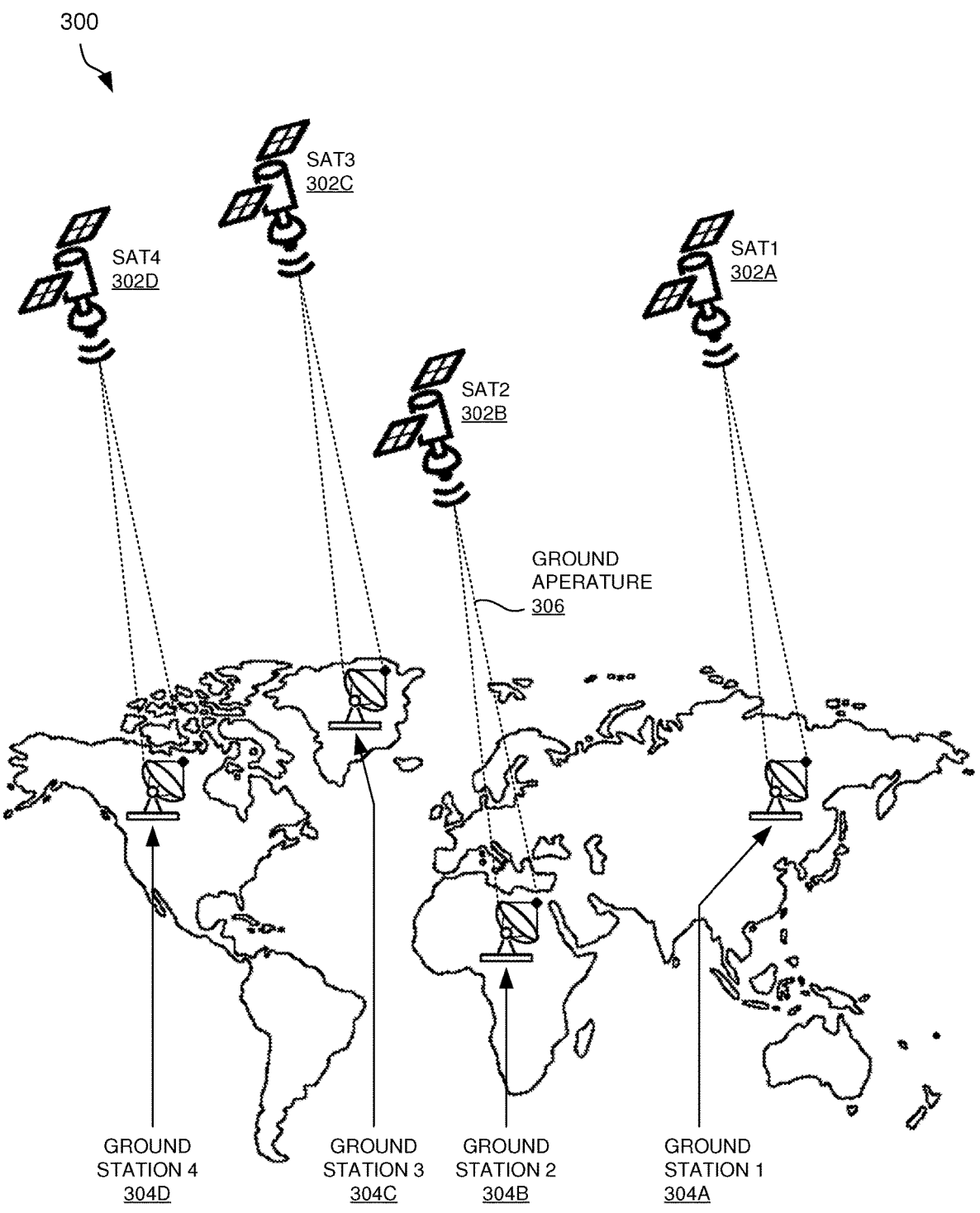
FIG. 3 shows a constellation of satellites in the sky over the earth where one or more satellites may be communicating with their nearest ground stations, in another embodiment.

FIG. 3 illustrates a depiction 300 of a constellation of satellites in the sky over the earth where one or more satellites may be communicating with their nearest ground stations, in another embodiment. As an option, FIG. 3 may be implemented in the context of any one or more of the embodiments set forth in any previous and/or subsequent figure(s) and/or description thereof. Of course, however, FIG. 3 may be implemented in the context of any desired environment. Further, the aforementioned definitions may equally apply to the description below.

In some aspects, the system may include a constellation of satellites in the sky over the earth where one or more satellites (such as satellites SAT1 302A-SAT4 302D) may be communicating with their nearest ground stations (such as ground station 1 304A-ground station 4 304D). The constellation of satellites (the satellites SAT1 302A-SAT4 302D) may be distributed in a manner that allows for efficient and effective communication with the ground stations (the ground station 1 403A-ground station 4 304D). The satellites (satellites SAT1 302A-SAT4 302D) may be positioned in various orbits around the earth, and their positions may be determined based on various factors such as the specific application requirements, the coverage requirements, and the availability of the satellites. For example, the ground aperture 306 shows the area on earth that can receive and send communication signals to the satellite (and hence can communicate data back- and forth to and from the satellite(s)).

In some cases, the system may include a message broker that is configured to route messages between the satellites (satellites SAT1 302A-SAT4 302D), the ground stations (ground station 1 304A-ground station 4 304D), the mission control station (not specifically shown in FIG. 3 but found in other figures), and the data center (not specifically shown in FIG. 3 but found in other figures). The message broker may be configured to route messages based on the location and availability of the satellites (satellites SAT1 302A-SAT4 302D) in the constellation. For example, the message broker may route messages to a satellite that is currently in a position to communicate with a ground station, and may route messages away from a satellite that is not currently in a position to communicate with a ground station. This allows for efficient use of the communication resources and ensures that the messages are delivered in a timely manner.

In some embodiments, the system may also include a sidecar proxy (not shown specifically in FIG. 3 but shown in other Figures herein) working with a send-queue and a receive-queue for messages to and from the satellites. In some embodiments, sidecar proxies may serve as ground interfaces for satellites, may encrypt and/or decrypt messages, and may work in conjunction with a send-queue and a receive-queue for communicating messages to and from the satellites. This allows for secure and efficient communication between the satellite and other nodes in the distributed system, such as ground stations, mission control stations, and datacenters.

Figure 4:
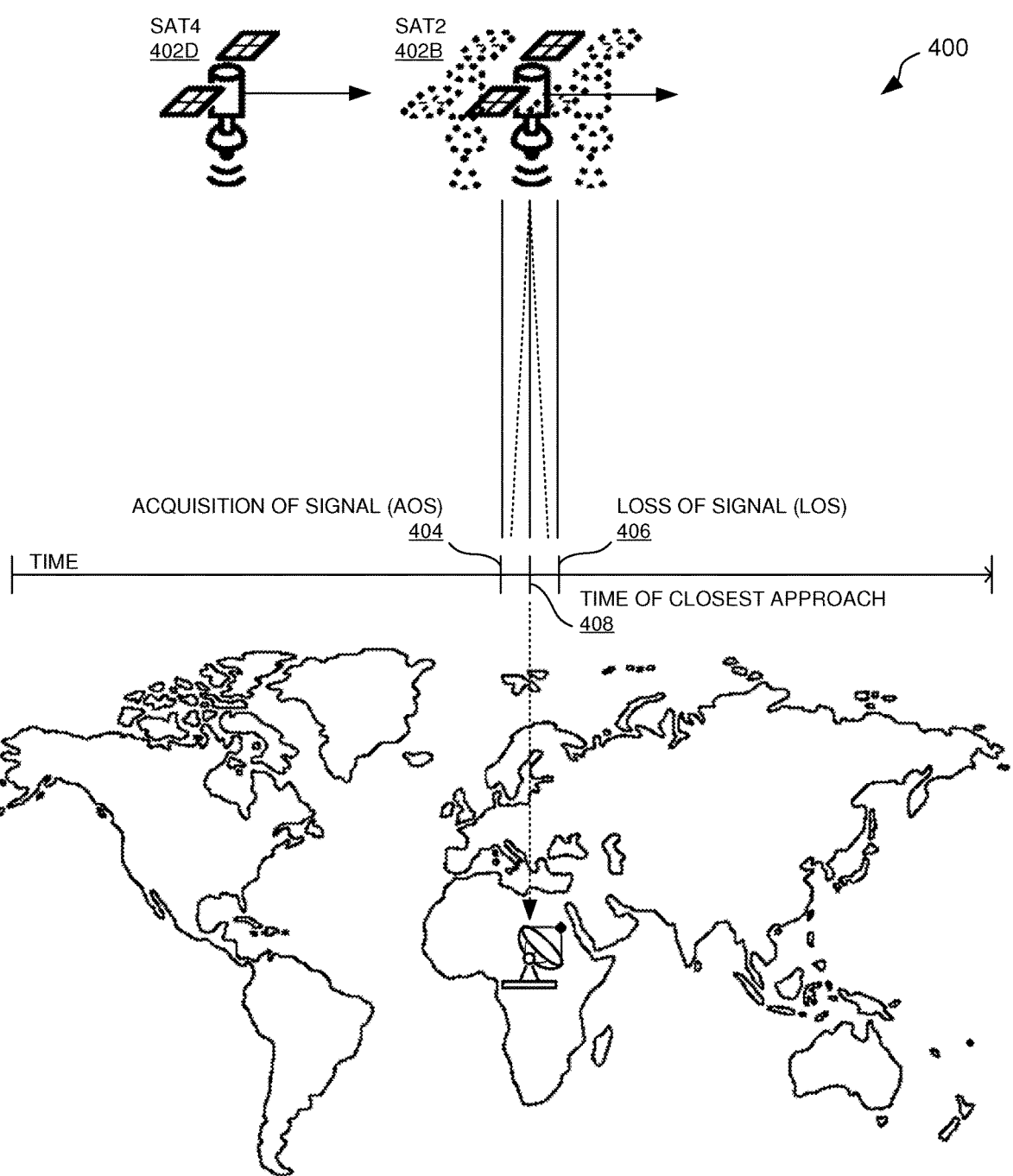
FIG. 4 presents satellites transiting over a ground location, in another embodiment.

FIG. 4 illustrates a depiction 400 satellites transiting over a ground location, in another embodiment. As an option, FIG. 4 may be implemented in the context of any one or more of the embodiments set forth in any previous and/or subsequent figure(s) and/or description thereof. Of course, however, FIG. 4 may be implemented in the context of any desired environment. Further, the aforementioned definitions may equally apply to the description below.

In some aspects, the system may include a satellite (SAT2 402B) transiting over a ground location and a second satellite (SAT4 402D) following it. The transit of the satellite (SAT2 402B) over the ground location may be determined based on various factors such as the satellite's orbit, the ground location's geographical coordinates, and the current time. The second satellite (SAT4 402D) following the first satellite (SAT2 402B) may be part of the same constellation and may be scheduled to transit over the same ground location at a later time, or it may be scheduled to transit over a different ground station if it is in a different orbit.

In some cases, the system may include a flight dynamics software for determining the correct Acquisition of Signal (AOS) 404 and Loss of Signal (LOS) 406 times for successful communication with the satellites. The AOS 404 time may be the time at which the satellite comes into the line of sight of the ground station, and the LOS 406 time may be the time at which the satellite goes out of the line of sight of the ground station. The flight dynamics software may calculate these times based on the satellite's orbit, the ground station's geographical coordinates, and the current time.

In some embodiments, the flight dynamics software may also calculate the Time of Closest Approach (TCA) 408, which is the time at which the satellite is closest to the ground station. The TCA 408 may be used to optimize the communication between the satellite (SAT2 402B) and the ground station, as the signal strength is typically strongest when the satellite is closest to the ground station.

In some aspects, the system may also include a mechanism for scheduling the communication between the satellites and the ground stations based on the AOS 404, LOS 406, and TCA 408 times. This scheduling mechanism may ensure that the communication is initiated at the AOS 404 time, maximized at the TCA 408 time, and terminated at the LOS 406 time, thereby optimizing the use of the communication resources.

In some cases, the system may also include a mechanism for rescheduling the communication in case of any disruptions or changes in the satellite's orbit or the ground station's availability. This rescheduling mechanism may ensure that the communication is seamlessly continued with the second satellite following the first satellite, thereby providing fault tolerance and ensuring uninterrupted communication in some cases. It should be noted that most satellites may be equipped with GPSs which allow the satellites to identify their own locations and may indicate its position to a ground station to initiate further communication upon Acquisition of Signal is completed.

Figure 5:
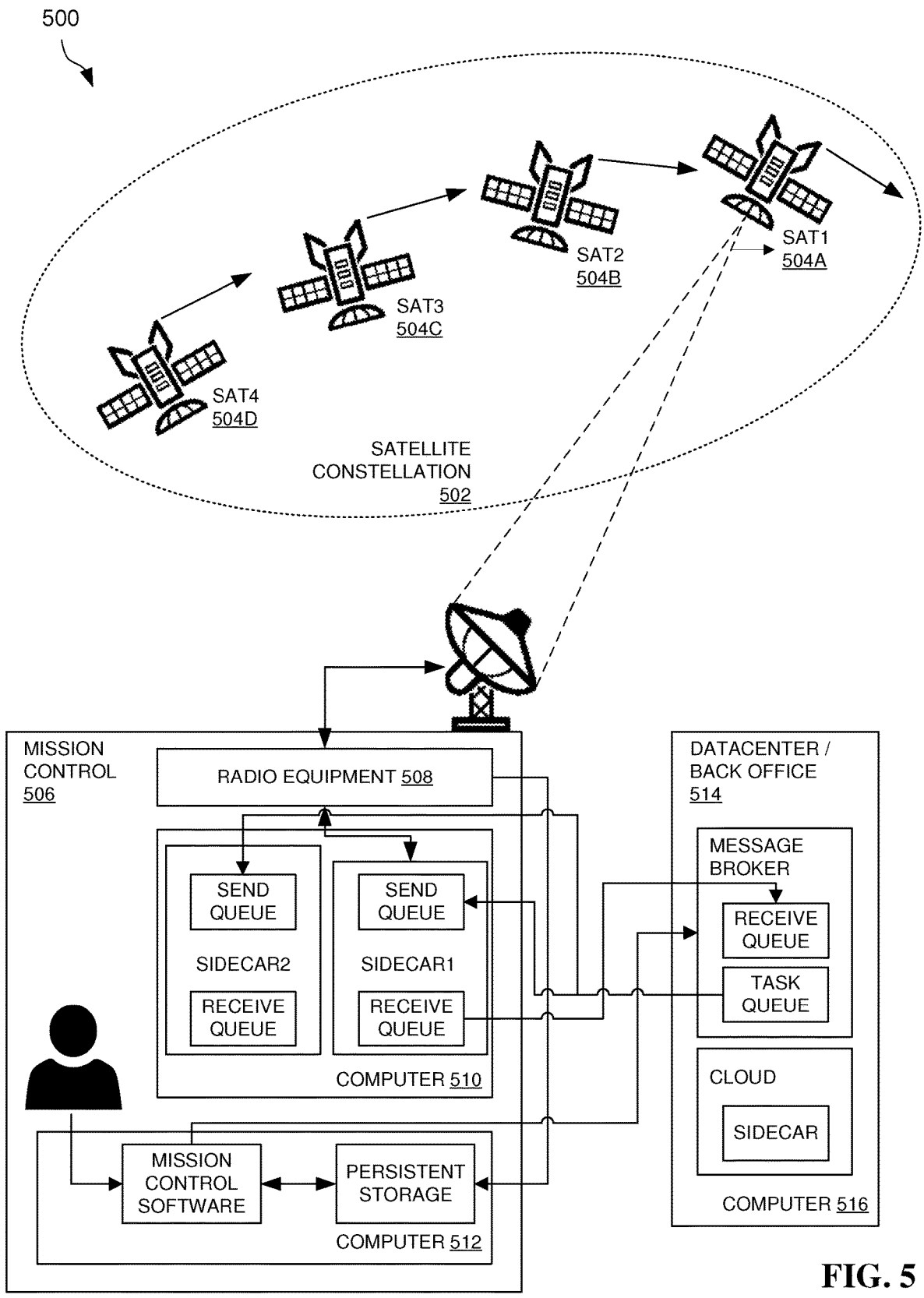
FIG. 5 demonstrates communication between Mission Control center and one or more satellites in the sky, in another embodiment.

FIG. 5 illustrates a depiction 500 of communication between Mission Control center and one or more satellites in the sky, in another embodiment. As an option, FIG. 5 may be implemented in the context of any one or more of the embodiments set forth in any previous and/or subsequent figure(s) and/or description thereof. Of course, however, FIG. 5 may be implemented in the context of any desired environment. Further, the aforementioned definitions may equally apply to the description below.

As shown, the satellites SAT 504A, SAT2 504B, SAT3 504C, and SAT4 504D may be included in the satellite constellation 502. It is to be appreciated that communication to any such satellites (such as with mission control 506) may occur individually, such as a direct communication between a single satellite such as SAT1 504A and the mission control 506, and/or between multiple satellites (such as satellite-to-satellite transmissions, or satellites-to-ground station transmissions). For purposes of the description herein, any transmission may be communicated to/from the mission control 506 to any or multiple of satellites in the satellite constellation 502.

The mission control 506 may comprise radio equipment 508, and a computer 510 including sidecar1 and sidecar2 proxies working with a send queue and receive queue. The mission control 506 may further comprise a computer 512 comprising mission control software and persistent storage. The computer 512 may be used to interface and/or receive commands from a user.

The datacenter/back-office 514 may comprise a computer 516 which may include a message broker configured with a receive queue and a task queue, as well as cloud-based sidecar proxy.

It is to be appreciated that the computer 510, the computer 512, and/or the computer 516 may be configured in a variety of alternative configurations. The intent is to have hardware sufficient for interaction with a user, storage of data generated using such systems, message brokers and sidecar proxies for sending/receive messages, etc. Further, such systems and configurations are intended to be scalable as needed such that multiple mission controls and/or datacenters/back-offices may be in communication in relation to the transmission to one or more satellites of the satellite constellation 502.

In some aspects, the system may include a communication mechanism between a human operator in a back-office or in Mission Control center (shown in FIG. 5 as mission control 506 and datacenter/back-office 514) and one or more satellites (via the satellite constellation 502 comprising but not limited or restricted to SAT1 504A-SAT4 504D) in the sky via a sidecar proxy (such as by using CELERY task queue framework) via the computer 510. The sidecar proxy via the computer 510 may be configured to work with a send-queue and a receive-queue for messages to and from the satellites. In some cases, the sidecar proxy via the computer 510 may work with the send-queue and the receive-queue using a secure database. This allows for secure and efficient communication between the satellite (and/or the constellation 502) and other nodes in the distributed system, such as ground stations, mission control stations (including the mission control 506), and datacenters (including the datacenter/back-office 514).

In some embodiments, the mission control 506 may communicate with the satellites of the satellite constellation 502 using micro-batching commands. This approach allows for efficient use of the communication window between the satellite and the ground station, ensuring that the maximum amount of data is transmitted within the available time.

In some cases, the datacenter/back-office 514 hosting a portion of an internet cloud may provide storage of data and allow packetized transfer of data similar to the internet. This enables the system to handle large volumes of data generated by the satellites and ensures that the data is readily available for processing and analysis.

In some aspects, the system may also include a mechanism for rescheduling the communication in case of any disruptions or changes in the satellite's orbit or the ground station's availability. This rescheduling mechanism may ensure that the communication is seamlessly continued with the second satellite following the first satellite, thereby providing fault tolerance and ensuring uninterrupted communication. Alternatively, the rescheduling mechanism may also ensure that the communication is seamlessly continued with the same satellite during a future passage over a ground station, as necessary.

In various embodiments, one or more operators may use mission control software (MCS) and Flight Dynamics Software/Simulator (FDS) (such as running on a local laptop or computer) via the computer 512 to determine and set up one or more commands to communicate to a satellite or a ground station and pass the one or more commands to a Message Broker (MB) of the computer 516. The message broker of the computer 516 may run as a process or thread in the datacenter/back-office 514. Additionally, it may run in a computer in mission control 506, etc. The message broker of the computer 516 can be implemented using a secure database that sets up a send-queue to send messages and a receive-queue to receive messages. The messages may be encrypted at any and all stages of such communication. The send-queue may receive messages from multiple operators and for one of more satellites. The message broker of the computer 516 may route the messages to the sidecar proxies (e.g. CELERYs) of the computer 510 of the appropriate satellites running as processes or threads on computers in the mission control 506 (or Ground Stations, etc.), and the sidecar proxies of the computer 510 may send the messages to the satellites (and/or the satellite constellation 502) via the radio equipment 508 and antennas of the mission control 506 (or a Ground Station) that is in communication with a satellite (or the constellation 502) in the sky transitioning to that ground location.

A sidecar proxy (e.g. CELERY, etc.) of the computer 510 may maintain a send-queue to send messages to the satellite using a predetermined radio channel of the radio equipment 508. Likewise, a sidecar proxy (e.g. CELERY, etc.) of the computer 510 may maintain a receive-queue to receive messages from the satellite (and/or the satellite constellation 502).

In one embodiment, it may be possible to implement a sidecar proxy even within a satellite for purposes of security, such as, for example, where the legacy code is running on the OBC (such as the OBC 204A, 204B) and all code on OBC executes and communicates only with the sidecar proxy inside the satellite to send messages to the ground or another node. Further, messages and responses may be received from the satellite (or the satellite constellation 502) by a sidecar proxy via the radio equipment 508 and the antennas of a ground station or the mission control 506. The sidecar proxy of the computer 510 may forward the messages to the message broker of the computer 516 which may route them to the appropriate/respective operators or software for analysis. Additionally, the operator may subscribe to the receive queue in the message broker of the computer 516 in order to view, listen, and/or act upon the messages received.

Overall, given the fact that the ground aperture (of a satellite trajectory) at a location and the interval between AOS and LOS may be limited, it is important to implement the procedures and methods disclosed herein such that active communication time with a satellite is as effective as possible.

Figure 6:
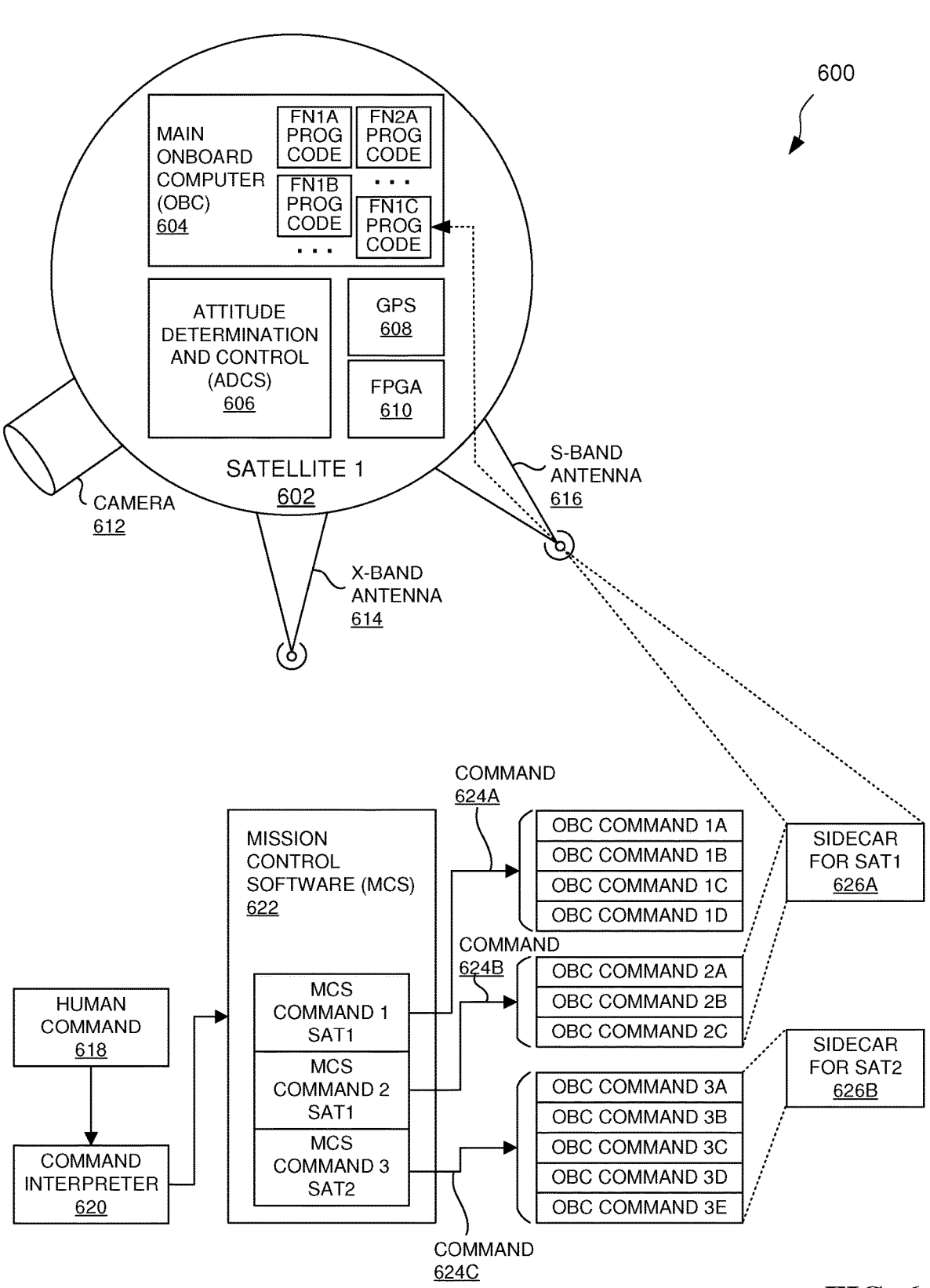
FIG. 6 highlights the concept of micro-batching commands, in another embodiment.

FIG. 6 highlights a depiction 600 of the concept of micro-batching commands, in another embodiment. As an option, FIG. 6 may be implemented in the context of any one or more of the embodiments set forth in any previous and/or subsequent figure(s) and/or description thereof. Of course, however, FIG. 6 may be implemented in the context of any desired environment. Further, the aforementioned definitions may equally apply to the description below.

In some aspects, the mission control station may be configured to communicate with the satellites using micro-batching commands. Within the context of the present disclosure, micro-batching includes separating data (or data streams) into small discrete batches. For example, micro-batching may include a technique that allows for efficient use of the communication window between the satellite and the ground station, ensuring that the maximum amount of data is transmitted within the available time. This approach can be particularly useful in scenarios where the communication window is limited, such as when the satellite is passing over a ground station.

In some cases, the micro-batching commands may be generated based on various factors such as the current state of the satellite, the type of data to be transmitted, and the available bandwidth. The micro-batching commands may include instructions for the satellite to perform various operations such as data collection, data processing, and data transmission. In a further embodiment, bulk data transmission may occur via protocols handling packetized data. However, scheduling the transmission of the data packets after packetizing may be dynamically controlled using commands sent via micro-batching.

In some embodiments, the micro-batching commands may be generated in a dynamic manner, taking into account the real-time conditions of the satellite and the ground station. For example, if the satellite is experiencing a high level of interference, the mission control station may generate micro-batching commands that instruct the satellite to reduce its data transmission rate or to switch to a different frequency band.

In some aspects, the micro-batching commands may be encrypted to ensure the security of the communication between the mission control station and the satellites. The encryption may be performed using various encryption algorithms and techniques, and the encrypted micro-batching commands may be decrypted by the satellites using corresponding decryption algorithms and techniques.

In some cases, the micro-batching commands may be transmitted to the satellites via a sidecar proxy, as described earlier, and shown as sidecar for SAT1 626A and sidecar for SAT2 626B. In some embodiments, sidecar proxies may serve as ground interfaces for satellites, may encrypt and/or decrypt messages, and may work in conjunction with a send-queue and a receive-queue for the micro-batching commands, and to transmit the micro-batching commands to the satellites in a timely and efficient manner.

In some embodiments, the system may also include a mechanism for rescheduling the communication in case of any disruptions or changes in the satellite's orbit or the ground station's availability. This rescheduling mechanism may ensure that the communication is seamlessly continued with the second satellite following the first satellite, thereby providing fault tolerance and ensuring uninterrupted communication. Alternatively, the rescheduling mechanism may also ensure that the communication is seamlessly continued with the same satellite during a future passage over a ground station, as necessary.

It is recognized that the amount of power available to a satellite to communicate with a ground station may be limited and be constrained by the charge in its batteries. As such, there exists a need to micro-batch such that commands and data may be effectively transmitted to and/or received from the satellite.

In one embodiment, FIG. 6 shows an example where a human operator may be given a task to determine one or more possible satellites to designate for the tasks and to transmit a set of commands (including a human command 618) associated with the task to mission control software (MCS) 622. In one embodiment, the task may be received by a command interpreter 620 software component for mission planning (MP) and mission administration (MA) which may work with mission planning software and flight dynamics software module. The MCS 622 may work with flight dynamics (FD) software module to determine the satellite trajectories and assignments. The MCS 622 may separate a set of commands from the command interpreter (CI) into satellite specific OBC Command Sets to be executed on the On-Board Computer(s) (OBC) of each of the satellites. These OBC commands may then be sent to appropriate sidecar proxies for each satellite. The OBC commands may be encrypted (such as the by the sidecar proxies) and routed to a designated ground station(s) (GS) that may communicate with the respective satellites. As such, therefore the MCS 622 may generate MCS commands (shown as MCS Command 1 SAT 1, MCS Command 2 SAT 1, MCS Command 3 SAT 2, etc.) via command signals command 624A, 624B, 624C, which may include OBC commands (shown as OBC Command 1A-1D, OBC Command 2A-2C, OBC Command 3A-3E, etc.). The OBC commands may then be sent to the appropriate sidecars and then communicated on to the appropriate satellite. Thus, OBC Command 2A-2C, for example, may be sent to sidecar for SAT1 626A, and communicate on to the S-Band antenna 616 of the satellite 1 602.

Consistent with the FIG. 2 description provided hereinabove, the satellite 1 may be configured to include a camera 612, a S-band antenna 616, a X-band antenna 614, an OBC 604, a ADCS 606, a GPS 608, a FPGA 610, etc. Further, data received, such as via the sidecar proxy for SAT 1 626A may be received via an antenna of the satellite 1 602, such as the S-band antenna 616, and communicated to the OBC 604 from processing, such as by a particular function program code module.

By way of example, a human command (such as the human command 618, control center command, and/or human task (e.g., various tasks such as 'use camera to survey polygon Area A on Earth', etc.) may be segmented into multiple commands and micro-batching may be used to send the commands to individual satellites. Further, the commands may be segmented into sets of OBC commands, which, in turn, may be sent as commands to the individual satellites. It is recognized that a variety of parameters may need to be configured (such as associated with motion of the satellite like the AOS, LOS, task queue, etc.). One advantage of using smart batching and micro-batching is that it may allow the human operator to guess and program certain parameters into a virtual satellite model and/or the flight dynamics software for a satellite approaching a ground station and iteratively determine the correct AOS and LOS and the interval size in time for the visibility of the satellite (e.g. 3 minutes, etc.). Smart batching allows the testing and readiness of the command set and its size before transit and/or passage over a ground station. It is to be appreciated that a mission control may also be a ground station.

As such, an integrated system (such as the system shown in FIG. 6) with micro-batching may assist in removing potential errors and automating correct and highly optimized commands in near real time. Further, in one embodiment, a command set sent to a satellite may be executed atomically.

In other embodiments, a human operator may target individual OBCs of individual satellites for communication and message passing. Further, such a distributed architecture mechanism may allow for load-balancing of tasks, or repurposing tasks between individual satellites of a cluster based on their location and availability. Such distribute architecture may therefore increase overall availability of satellite(s). Additionally, in various embodiments, the distributed architecture mechanism may allow for distributed message passing and queuing mechanism, thereby reducing human error and time (as the system can be used to determine parameters associated with motion of the satellite (such as AOS, LOS, task queue) and the programming of each parameter and/or individual OBC commands.

By way of example, if any satellite temporarily disappears from the ground aperture at a ground location or is disabled, the flight dynamics control and distributed system may allow remote rescheduling or reset of a satellite OBC at another compliant ground station when it passes over it.

In one embodiment, through having an architecture including sidecar proxies, the system may be scaled such that new satellites may be easily deployed within the system. In this manner, addition (and/or deletion) and management of satellite(s) may be facilitated by the distributed system disclosed herein.

In one embodiment, the movement of the earth may cause a satellite to be in a shadow and become unavailable for remote sensing or aerial survey over certain earth locations for several weeks sometimes. However, for a constellation of satellites spread geographically over the earth, at least one or more satellites of the constellation may be available for the survey or remote sensing at some of those locations. Therefore, re-balancing by re-purposing the individual satellites between themselves for the task can allow for task continuity and completion in a reasonable time without waiting several weeks.

As such, the present disclosure discusses such repurposing and rebalancing of tasks between satellites in a constellation, thereby significantly improving availability. In one embodiment, achieving continuous and meaningful coverage of a large area may occur via tiling (as shown herein with respect to FIG. 8, disclosed hereinbelow).

Figure 7:
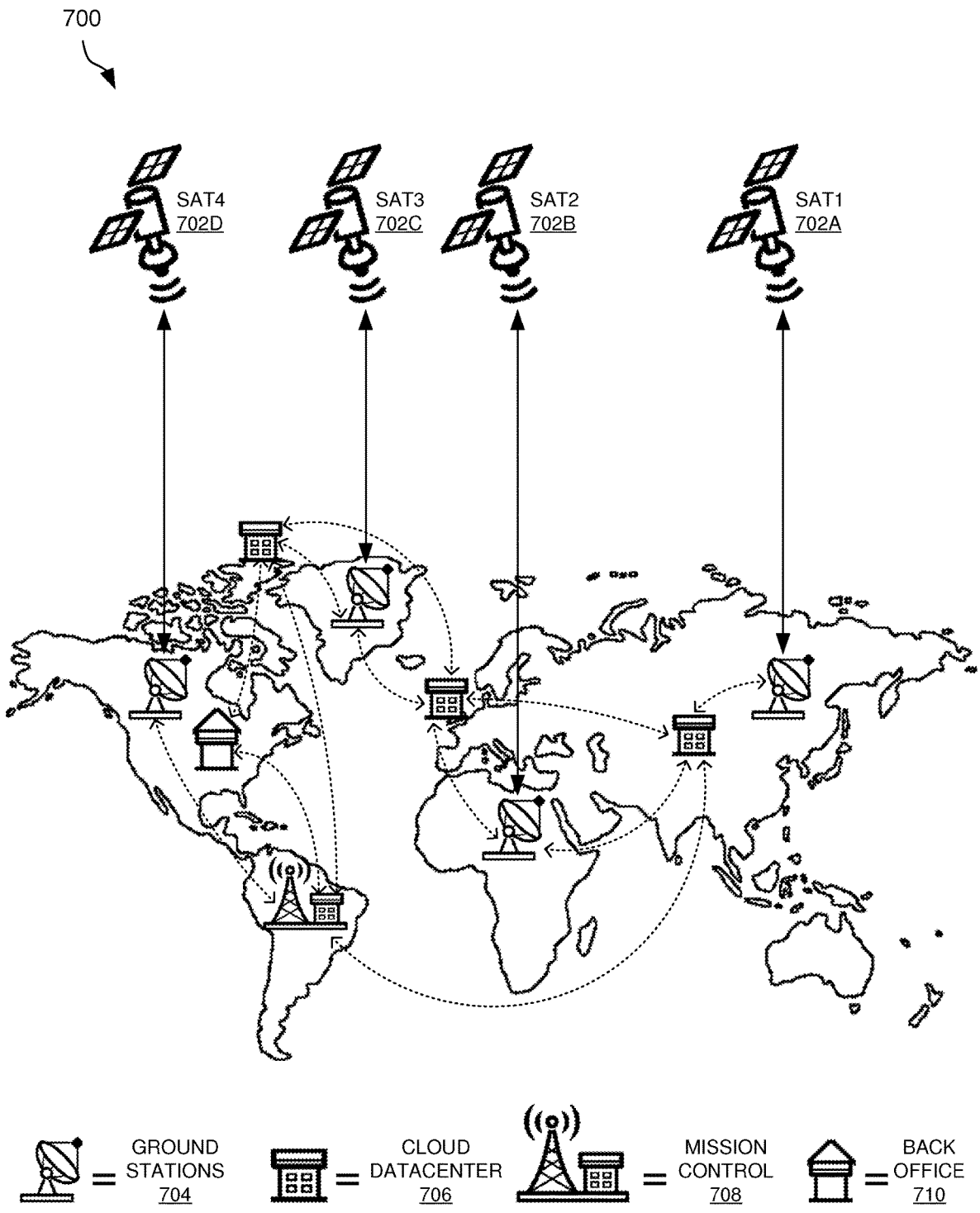
FIG. 7 illustrates a fault-tolerant and load balancing infrastructure, in another embodiment.

FIG. 7 illustrates a depiction 700 of a fault-tolerant and load balancing infrastructure, in another embodiment. As an option, FIG. 7 may be implemented in the context of any one or more of the embodiments set forth in any previous and/or subsequent figure(s) and/or description thereof. Of course, however, FIG. 7 may be implemented in the context of any desired environment. Further, the aforementioned definitions may equally apply to the description below.

In some aspects, the system may include a fault-tolerant infrastructure comprising a constellation of satellites SAT1 702A-SAT4 702D, mission control 708 and ground stations 704, cloud datacenters 706, and/or back-office 710. The cloud datacenters 706 may host a portion of an internet cloud, which in some cases, may be configured to provide storage of data and allow packetized transfer of data similar to the internet. This enables the system to handle large volumes of data generated by the satellites 702A-702D and ensures that the data is readily available for processing and analysis.

In some embodiments, the system may be configured to provide fault tolerance by allowing remote rescheduling or reset of a satellite On-Board Computer (OBC) at another compliant ground station of the ground stations 704 when the satellite passes over it. This feature may ensure that the communication is seamlessly continued with the second satellite following the first satellite, thereby providing fault tolerance and ensuring uninterrupted communication.

In some cases, the system may provide fault tolerance by allowing remote rescheduling or reset of a satellite On-Board Computer (OBC) at another compliant ground station of the ground stations 704 when the satellite passes over it. This rescheduling mechanism may ensure that the communication is seamlessly continued with the second satellite following the first satellite, thereby providing fault tolerance and ensuring uninterrupted communication. Alternatively, the rescheduling mechanism may also ensure that the communication is seamlessly continued with the same satellite during a future passage over a ground station, as necessary. This feature may be particularly useful in scenarios where a satellite temporarily disappears from the ground aperture at a ground location or is disabled.

In some aspects, the fault-tolerant infrastructure may be designed to handle various types of disruptions or changes in the satellite's orbit or the ground station's availability. This may include, for example, changes in the satellite's orbit due to space weather events, equipment failures, or other unforeseen circumstances. The infrastructure may also be designed to handle changes in the ground station's availability due to factors such as equipment failures, network outages, or other unforeseen circumstances.

In some embodiments, the fault-tolerant infrastructure may include various mechanisms for detecting and responding to these disruptions or changes. These mechanisms may include, for example, sensors and monitoring systems for detecting disruptions or changes, algorithms and decision-making systems for determining the appropriate response, and control systems for implementing the response. These mechanisms may be implemented in hardware, software, or a combination of both, and may be distributed across the various components of the infrastructure.

In various embodiments, a satellite may be configured to send messages via ground resources (such as a control center) using message passing protocols (such as similar to TCP/IP but with limited retries, Cubesat Space Protocol (CSP), GRPC, etc.). It is recognized that if a satellite of the satellites 702A-702D is in a location not visible to a ground station of the ground stations 704, then the message communicated by the satellite may be lost. As such, the time aperture for communication with a satellite may be bound by the time of Acquisition of Signal (AOS) and the time of Loss of Signal (LOS). Between the AOS and LOS there is a point in time when the satellite is closest to a location on earth called the TCA (Time of Closest Approach). The Flight Dynamics software may be used to determine the correct AOS and LOS times in order to successfully communicate with the satellite. For example, the Flight Dynamics may use NORADs and/or two line element (TLE) to predict/determine the ground track of a satellite.

Further, the ground aperture, the AOS, the TCA and/or the LOS at a ground location on earth may be used for communication, aerial survey, aerial photography, and system recalibration, repair, diagnosis, testing, etc. As such, communication at that location must be completed within the interval of time between the AOS and LOS. It is to be appreciated that any ground location (such as the ground stations 704, the cloud datacenter 706, the mission control 708, and/or the back-office 710) may be used singularly or in combination for communication between ground-based systems and/or the satellite systems.

In one embodiment, every time a new satellite is added, or an existing satellite is altered (such as being disabled, decommissioned, and/or temporarily absent, etc.), the software system may have to be reconfigured (in part and/or in whole, etc.). For example, the operator may substitute a first satellite with another one that is approaching the location with appropriate parameters. Further, the operator can modify the availability list of satellites that use the message broker, and the distributed system may affect such changes (such that the availability list is distributed throughout the system).

By way of example, in one case, a file transfer task from one ground location to another ground location may be interrupted if a satellite is outside the line of sight (LoS) and/or aperture of sight of the locations. However, if the file transfer task can be seamlessly transferred from one satellite moving out to another satellite moving into a location, then the task may continue without interruption. This distributed architecture therefore may allow such tasks to be seamlessly ported from one satellite to another in a constellation. The ground station of the ground stations 704, cloud datacenter 706, the mission control 708, and/or the back-office 710 can provide storage of data and allow packetized transfer (in a manner similar to the internet transmit/receipt of data packets). It is envisioned that isochronous channels may be integrated of short duration for voice and video communication using this distributed system of satellites.

In one embodiment, the mission control 708 may have to reset or even update the BIOS and the OS kernel in an older satellite. This can be done, in one embodiment, using commands (such as simple FTP commands) to the OBC on the satellites. Multiple versions of OS kernels can reside on the satellite and rollover of a non-working kernel to a previous revision is envisioned.

Figure 8:
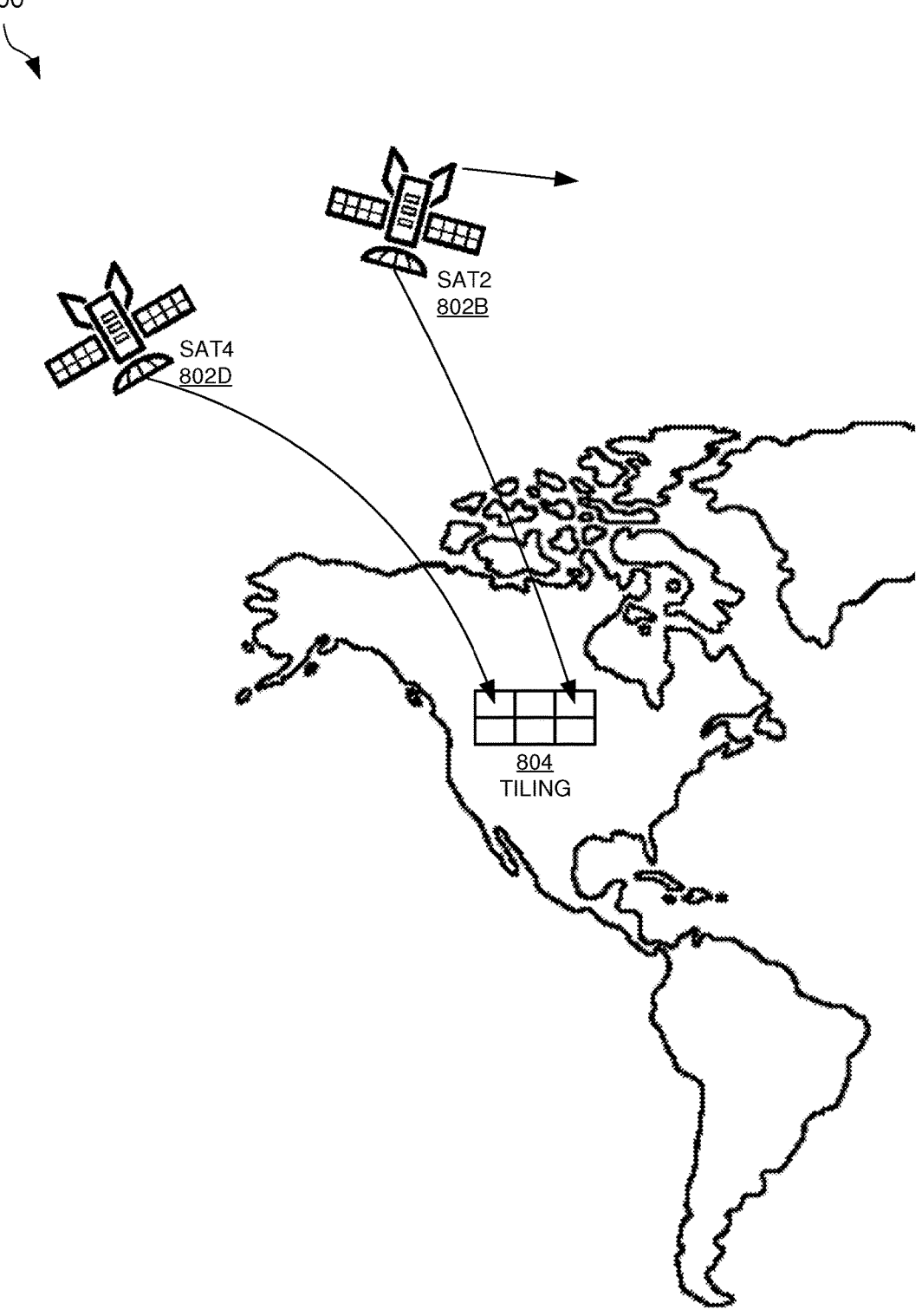
FIG. 8 shows an area on earth divided into tiles by latitude and longitude for a constellation of satellites to perform aerial survey, in another embodiment.

FIG. 8 illustrates a depiction 800 of an area on earth divided into tiles by latitude and longitude for a constellation of satellites to perform aerial survey, in another embodiment. As an option, FIG. 8 may be implemented in the context of any one or more of the embodiments set forth in any previous and/or subsequent figure(s) and/or description thereof. Of course, however, FIG. 8 may be implemented in the context of any desired environment. Further, the aforementioned definitions may equally apply to the description below.

In some aspects, the system may include an area on earth divided into tiles (herein referred to as tiling 804) by latitude and longitude for a constellation of satellites SAT2 802B and/or SAT4 802D to perform aerial survey. This tiling 804 approach allows for efficient and effective management of the aerial survey tasks by dividing the large survey area into smaller, manageable tiles. Each tile of the tiling 804 may represent a specific geographical area on the earth, and the satellites in the constellation may be tasked with performing the aerial survey of these tiles of the tiling 804 in a coordinated manner.

In some cases, the tiling 804 of the ground area into tiles and the tasks for each tile are enqueued and the message broker and the constellation can distribute or redistribute the tasks or work between multiple satellites based on their ground location, flight path, and times of Acquisition of Signal (AOS), Loss of Signal (LOS), and Time of Closest Approach (TCA) at a preceding ground station. This allows for efficient use of the satellite resources and ensures that the aerial survey tasks are completed in a timely manner.

In some embodiments, the system may also include a mechanism for rescheduling the aerial survey tasks in case of any disruptions or changes in the satellite's orbit or the ground station's availability. This rescheduling mechanism may ensure that the aerial survey tasks are seamlessly continued with the second satellite following the first satellite, thereby providing fault tolerance and ensuring uninterrupted aerial survey.

In some aspects, the system may also include a mechanism for repurposing the aerial survey tasks between individual satellites based on their location and availability. This repurposing mechanism may allow the aerial survey tasks to be reassigned from one satellite to another satellite that is approaching the same tile or a nearby tile of the tiling 804. This can increase the overall efficiency and effectiveness of the aerial survey and can help to ensure that the aerial survey tasks are completed in a timely manner, even in the face of disruptions or changes in the satellite's orbit or the ground station's availability.

In various embodiments, the tiles of the tiling 804 may be detailed by latitude and longitude, such as for a constellation of satellites to perform aerial survey. Tiling 804 the ground area may include separating the area into configured (defined geographic area) tiles. Further, the tasks for each tile may be enqueued, and the message broker and the constellation can distribute or redistribute the tasks/work between multiple satellites based on their ground location, flight path, and times of AOS, LOS and TCA (Time of Closest Approach).

FIG. 9A provides a UI/UX 901A front-end for Mission Control and Flight Dynamics Software, in another embodiment. As an option, FIG. 9A may be implemented in the context of any one or more of the embodiments set forth in any previous and/or subsequent figure(s) and/or description thereof. Of course, however, FIG. 9A may be implemented in the context of any desired environment. Further, the aforementioned definitions may equally apply to the description below.

Additionally, FIG. 9B shows computing infrastructure 901B for control of satellites, in another embodiment. As an option, FIG. 9B may be implemented in the context of any one or more of the embodiments set forth in any previous and/or subsequent figure(s) and/or description thereof. Of course, however, FIG. 9B may be implemented in the context of any desired environment. Further, the aforementioned definitions may equally apply to the description below.

In some aspects, the system may include a user interface/user experience (UI/UX), UI/UX 901A front-end for session control software 912 and flight dynamics software 910, along with a virtualized platform of virtual satellites, virtual ground stations, and a model of earth in simulation. This virtualized platform may serve as a virtual satellite simulation infrastructure that allows for the creation of new satellites to study what-if scenarios. These scenarios may be used to pre-determine the trajectories before launch for new satellites or the trajectories for existing satellites before a specific date.

In some cases, the virtual satellite simulation infrastructure of the UI/UX 901A, may be configured to simulate one or more trajectories of the satellites based on predetermined parameters. These parameters may include the location, flight path, desired elevation, and times of Acquisition of Signal (AOS) and Loss of Signal (LOS) of the satellites. This simulation capability allows for efficient planning and management of the satellite operations, ensuring that the satellites are positioned in the right orbits and are able to communicate effectively with the ground stations.

In some embodiments, the virtual satellite simulation infrastructure may be further configured to adjust the predetermined parameters based on real-time data received from the satellites. This feature allows for dynamic adjustment of the satellite trajectories based on the actual conditions in space, thereby enhancing the accuracy and reliability of the satellite operations.

In various embodiments, the UI/UX 901A may include a variety of different information, data, functions, and/or controls, including but not limited to command description (to delineate the command to be executed), a ground station pass date and time, a raw command in binary form, ground station ID, ground station name, maximum elevation, acquisition of signal (AOS), time of closest approach (TCA), loss of signal (LOS), adjusted time, offset, CSP address, preamble, duration, TTC ID, and/or passage ID. In the context of this description a raw command may include a binary or hex version of an ASCII/UNICODE or English (or human language) command/mnemonic.

In some aspects, the UI/UX 901A front-end for mission control and flight dynamics software may provide a user-friendly interface for the human operators to interact with the system. The operators may use this interface to monitor the status of the satellites, plan and schedule satellite operations, and analyze the data received from the satellites. The interface may also provide various tools and features to assist the operators in their tasks, such as data visualization tools, alert and notification systems, and decision support systems.

In some cases, the UI/UX 901A front-end may be designed to be intuitive and easy to use, reducing the learning curve for the operators and increasing their productivity. It may also be customizable to suit the specific requirements and preferences of the operators, thereby enhancing their user experience.

In some embodiments, the UI/UX 901A front-end may be accessible from various devices, such as desktop computers, laptops, tablets, and smartphones. This allows the operators to access the system from anywhere, at any time, thereby increasing the flexibility and convenience of the system.

In some aspects, the UI/UX 901A front-end may be integrated with other systems and applications, such as data analysis tools, reporting tools, and communication tools. This allows for seamless data sharing and collaboration between the operators and other stakeholders, thereby enhancing the efficiency and effectiveness of the satellite constellation management and control process.

In various embodiments, the software systems for controlling satellites may allow a user 916 to present a distributed task via computer 908 to a constellation of virtual machines or virtual satellites, and the message broker and flight control system may allow the distributed task to be appropriately scheduled and/or load balanced based on the location, AOS, LOS of the satellites in the constellation.

As such, virtual satellites and simulations may be used to prepare for and test deployment of satellite(s) prior to actual deployment. In one embodiment, using virtual satellites and performing simulations ahead of time may prepare the human operator to quickly set up and communicate with an actual satellite when it is able to communicate with a permitted ground station. As such, a user 916 in communication with the software systems, such as the computer 908, may view and/or control a virtual platform 906 comprising virtual satellites, virtual ground stations, and earth map/globe. In this manner, ground stations GS1 904A-GS4 904D may be in communication with any or all of satellites SAT1 902A-SAT4 902D. Such virtual platform 906 of the computer 908 may also work in combination with the flight dynamics software 910, the mission control software 912, and/or sidecar proxies 914A-914D to accurately create a virtualized simulation of satellites, satellite interaction, and predicted satellite trajectories.

In one embodiment, such software systems may allow dockers (e.g. kubernites) to be used to create virtual workers that can be ported wholesale across OBCs inside satellites. Such an architecture may allow for replication of workers/tasks.

In another embodiment, the virtual satellite simulation infrastructure may allow for creation of new satellites to study what-if scenarios to pre-determine the trajectories before launch for new satellites or the trajectories for existing satellites before a certain date. It may allow a user in Mission Planning to study load balancing and tiling scenarios as well as for testing out new and existing commands to control satellites, along with small micro-batching command blocks in preparation for deployment at a later time. Furthermore, the integrated system may allow for seamless deployment from the virtual environment to the real-world environment.

FIG. 10 illustrates an integrated simulation workspace 1000 for satellites, in another embodiment. As an option, FIG. 10 may be implemented in the context of any one or more of the embodiments set forth in any previous and/or subsequent figure(s) and/or description thereof. Of course, however, FIG. 10 may be implemented in the context of any desired environment. Further, the aforementioned definitions may equally apply to the description below.

As shown, the integrated simulation workspace 1000 comprises a variety of information and/or controls for interaction with a real or simulated satellite action. For example, a simulation may be conducted for a particular customer (e.g. remote sensing customers, surveillance customers, telecommunication customers, etc.), and/or order type (e.g., mining tailing, mineral exploration, subsidence, mapping, GIS mapping, imaging method, etc.), as well as display associated information including an order ID and/or status (of the satellites in the simulation). Further, this UI/UX based workspace may be applicable and function as the main interface for both REAL satellites in space and for virtual satellites in simulation. Additionally, the satellites may be configured (within real-world or insimulated setting) with respect to resolution (of cameras within the satellite, such imagery at e.g., 30 cm, 50 cm, 70 cm, 2 m, 5 m, 10 m, 15 m, 30 m resolution, etc., for example). Additionally, the satellite band (e.g., 450-464 nm, 464-478 nm, 478-492 nm, 675-689 nm, etc.) may be specified. Further, services performed by the satellite may be specified, including but not limited to capturing a raw image, controlling atmospheric correction and/or radiometric correction, making signal-tonoise ratio (SNR) improvements, visualizing current view of the satellite, etc. It is to be appreciated that other functions, controls, and data may be displayed as desired in relation to the simulated workspace. In the context of this description radiometric correction implies modifying the raw binary data obtained from a camera or sensor into a corrected and intelligible image that indicates certain properties of the area photographed or sensed. In the context of this description, the term visualization implies overlaying a photographed or sensed image of an area of interest over an existing map of the area of interest as in a GIS or using a GIS.

Further, information on the Area of Interest (latitudes and longitudes to bound an area of interest, and/or a representative center (e.g., LATTITUDE-C, LONGITUDE-C)) and satellites may be displayed, including position (latitude, longitude), as well as satellite transit information, including points of interest, time of AOS, time of TCA, time of LOS, etc. Again, as discussed above, the integrated simulation workspace 1000 may conduct simulations and display results within the context of a simulation result.

In some aspects, the system may include one or more satellites in a constellation. These satellites may be small satellites, such as CubeSats, in some cases. The small size and low cost of CubeSats make them an attractive option for various applications, including communication, earth observation, and scientific research. Despite their small size, CubeSats can be equipped with a variety of sensors and instruments, allowing them to perform a wide range of tasks. In another aspect, a single satellite may be used.

In some embodiments, the system may include a message broker configured to route messages between the satellites, the ground stations, the mission control station, and the data center. The routing of messages may be based on the location and availability of the satellites in the constellation. For example, the message broker may route messages to a satellite that is currently in a position to communicate with a ground station, and may route messages away from a satellite that is not currently in a position to communicate with a ground station. This allows for efficient use of the communication resources and ensures that the messages are delivered in a timely manner.

In some cases, the system may include a mechanism for rescheduling the communication in case of any disruptions or changes in the satellite's orbit or the ground station's availability. This rescheduling mechanism may ensure that the communication is seamlessly continued with the second satellite following the first satellite, thereby providing fault tolerance and ensuring uninterrupted communication. Alternatively, the rescheduling mechanism may also ensure that the communication is seamlessly continued with the same satellite during a future passage over a ground station, as necessary. This feature may be particularly useful in scenarios where a satellite temporarily disappears from the ground aperture at a ground location or is disabled.

In some aspects, the fault-tolerant infrastructure may be designed to handle various types of disruptions or changes in the satellite's orbit or the ground station's availability. This may include, for example, changes in the satellite's orbit due to space weather events, equipment failures, or other unforeseen circumstances. The infrastructure may also be designed to handle changes in the ground station's availability due to factors such as equipment failures, network outages, or other unforeseen circumstances.

In some embodiments, the fault-tolerant infrastructure may include various mechanisms for detecting and responding to these disruptions or changes. These mechanisms may include, for example, sensors and monitoring systems for detecting disruptions or changes, algorithms and decision-making systems for determining the appropriate response, and control systems for implementing the response. These mechanisms may be implemented in hardware, software, or a combination of both, and may be distributed across the various components of the infrastructure.

Figure 11:
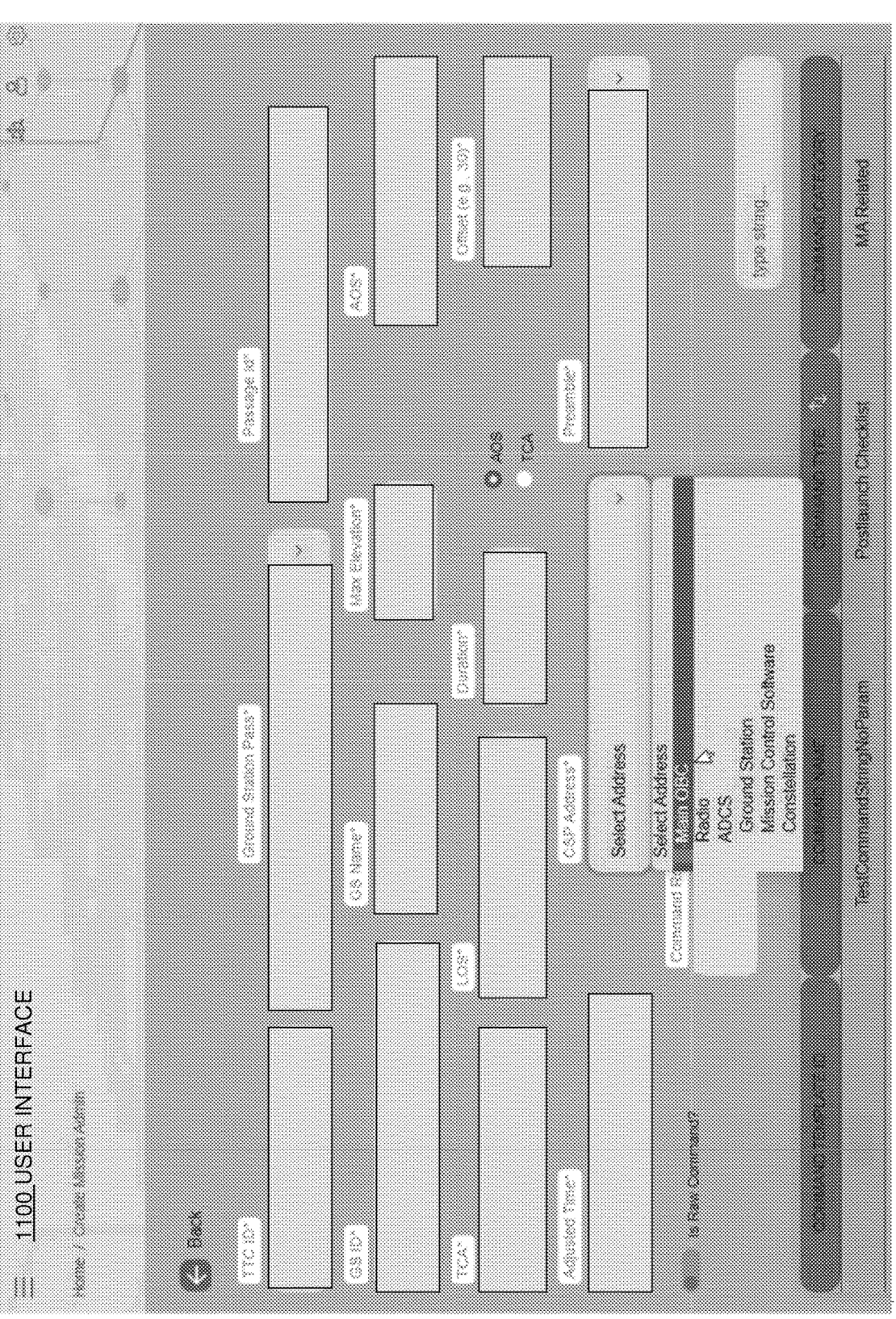
FIG. 11 shows a user interface for control of satellites, in another embodiment.

FIG. 11 illustrates a user interface 1100 for control of satellites, in another embodiment. As an option, FIG. 11 may be implemented in the context of any one or more of the embodiments set forth in any previous and/or subsequent figure(s) and/or description thereof. Of course, however, FIG. 11 may be implemented in the context of any desired environment. Further, the aforementioned definitions may equally apply to the description below.

As shown, the user interface 1100 includes data, functions, and controls relating to a user interface for a mission control center, and/or a ground based system to control satellites. The user interface 1100 includes transit related information, comprising telemetry, tracking and command (TTC) data, ground station pass (date/time of passage of satellite), a passage id (of the satellite over the ground based center), a ground station ID and/or name, elevation of the satellite over a ground station, AOS, TCA, LOS, duration (of the transit), offset (in degrees or in time units), adjusted time or adjusted duration of passage, CSP address which may indicate the communication network address of a satellite, etc. The offset may be an interval of time or an interval or a portion of an elevation angle sweep associated with a satellite transit over a ground station at the beginning or towards the end of the transit where only preamble type signals may be sent to complete an acquisition of signal (AOS) or to complete close of communication before loss of signal (LOS). The offset may be taken from the AOS (or LOS) or it may be measured from the TCA as the valid region when messaging can be done to and from the satellite. The AOS, LOS and/or TCA may be given as date and time pairs. It is to be appreciated that any type of information associated with the satellites, the ground based control centers (mission control, ground stations, cloud datacenters, back-office, etc.) may be displayed within the user interface 1100. A variety of CSP addresses (or other network addresses) may be selected for communication with entities within a satellite like OBC or ADCS, or outside a satellite, including ground stations, virtual satellites in simulation, mission control software, or for network loopback, or for broadcast to one or more satellites in a constellation. Further, the command types/structures being used may also be included in the user interface 1100 in the user interface 1100. Examples of command types/structures may include intents at the highest level, high level mnemonic or Unicode commands, or ASCII commands, or raw hex or binary commands (sometimes referred to as micro-commands), or commands in smart batches or micro batches.

Further, the user interface 1100 may include the ability to control and/or manipulate satellite actions, and provide fields for input relating to a command template (which can then be modified/filled out as desired), command name, command type, and/or command category. In this manner, control of the satellite may be configured by the user interface 1100. It is to be further appreciated that the user interface 1100 may be used to control deployed satellites (in actual orbit) and/or virtualized satellites (such as in relation to the integrated simulation workspace 1000 and/or the computing infrastructure 901B and/or UI/UX 901A.

In some aspects, the system may include one or more satellites in a constellation. These satellites may be small satellites, such as CubeSats, in some cases. The small size and low cost of CubeSats make them an attractive option for various applications, including communication, earth observation, and scientific research. Despite their small size, CubeSats can be equipped with a variety of sensors and instruments, allowing them to perform a wide range of tasks. In other aspects, a single satellite may be used.

In some embodiments, the system may include a message broker configured to route messages between the satellites, the ground stations, the mission control station, and the data center. The routing of messages may be based on the location and availability of the satellites in the constellation. For example, the message broker may route messages to a satellite that is currently in a position to communicate with a ground station, and may route messages away from a satellite that is not currently in a position to communicate with a ground station. This allows for efficient use of the communication resources and ensures that the messages are delivered in a timely manner.

In some cases, the system may include a mechanism for rescheduling the communication in case of any disruptions or changes in the satellite's orbit or the ground station's availability. This rescheduling mechanism may ensure that the communication is seamlessly continued with the second satellite following the first satellite, thereby providing fault tolerance and ensuring uninterrupted communication. Alternatively, the rescheduling mechanism may also ensure that the communication is seamlessly continued with the same satellite during a future passage over a ground station, as necessary. This feature may be particularly useful in scenarios where a satellite temporarily disappears from the ground aperture at a ground location or is disabled.

In some aspects, the fault-tolerant infrastructure may be designed to handle various types of disruptions or changes in the satellite's orbit or the ground station's availability. This may include, for example, changes in the satellite's orbit due to space weather events, equipment failures, or other unforeseen circumstances. The infrastructure may also be designed to handle changes in the ground station's availability due to factors such as equipment failures, network outages, or other unforeseen circumstances.

In some embodiments, the fault-tolerant infrastructure may include various mechanisms for detecting and responding to these disruptions or changes. These mechanisms may include, for example, sensors and monitoring systems for detecting disruptions or changes, algorithms and decision-making systems for determining the appropriate response, and control systems for implementing the response. These mechanisms may be implemented in hardware, software, or a combination of both, and may be distributed across the various components of the infrastructure.

In various embodiments, the systems and methods disclosed herein may allow for a lower-cost, highly distributed, highly customizable deployment and management/control of satellite and/or satellite constellations. Further, implementing the virtual satellite systems disclosed herein may allow for greater insights into actual satellite deployment (which in turn may drive down cost and increase fidelity of data with real world conditions). As such, machine learning may be implemented to model and train satellite activity both before (via virtual deployment) and/or after actual deployment.

Figure 12:
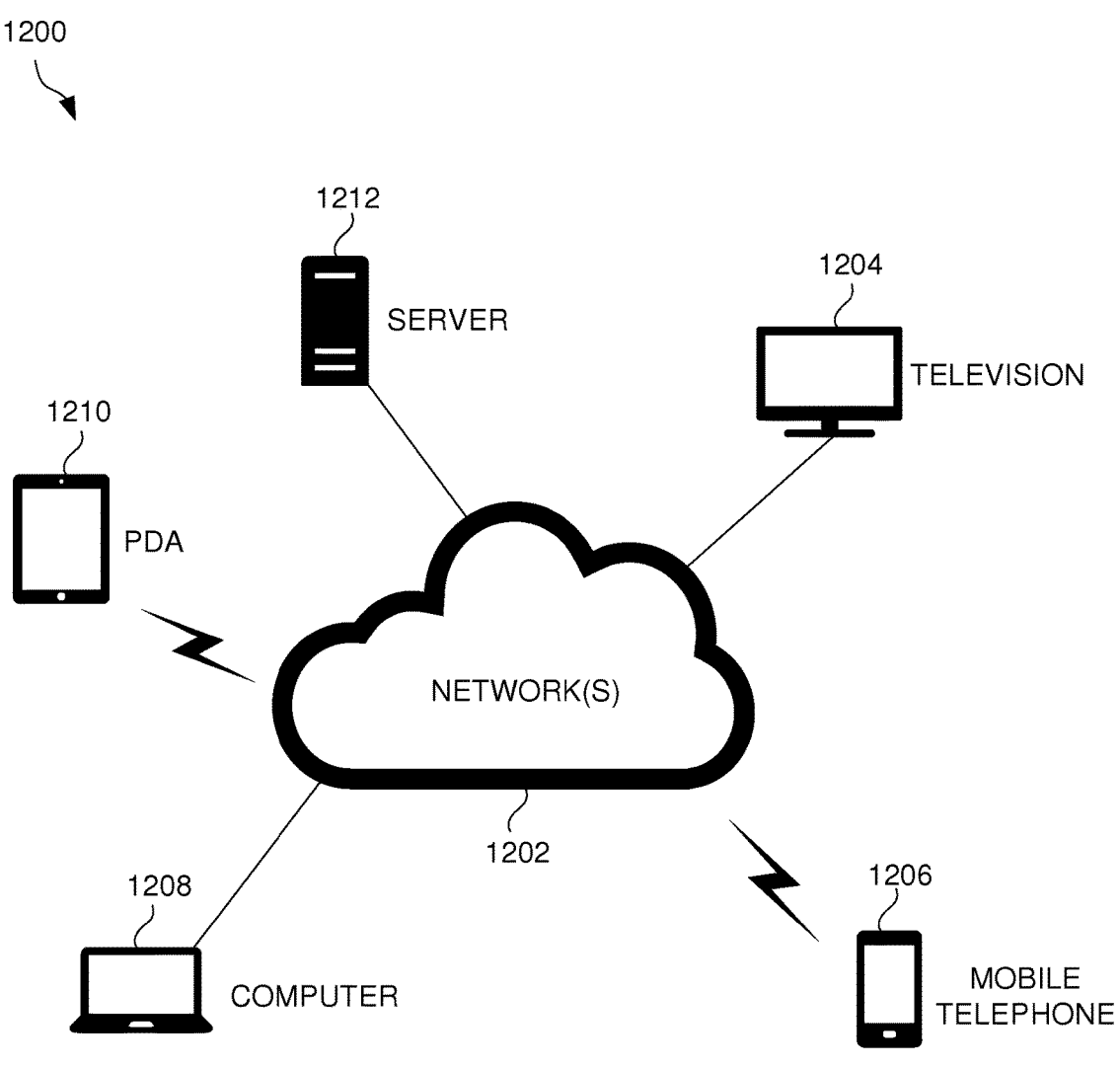
FIG. 12 illustrates a network architecture, in accordance with one possible embodiment.

FIG. 12 illustrates a network architecture 1200, in accordance with one possible embodiment. As shown, at least one network 1202 is provided. In the context of the present network architecture 1200, the network 1202 may take any form including, but not limited to a telecommunications network, a local area network (LAN), a wireless network, a wide area network (WAN) such as the Internet, peer-to-peer network, cable network, etc. While only one network is shown, it should be understood that two or more similar or different networks 1202 may be provided.

Coupled to the network 1202 is a plurality of devices. For example, a server computer 1212 and an end user computer 1208 may be coupled to the network 1202 for communication purposes. Such end user computer 1208 may include a desktop computer, lap-top computer, and/or any other type of logic. Still yet, various other devices may be coupled to the network 1202 including a personal digital assistant (PDA) device 1210, a mobile phone device 1206, a television 1204, etc. It is to be appreciated that a satellite may include an on-board computer and function (within the context of FIG. 12) in a manner similar to the operation of the computer 1208.

Figure 13:
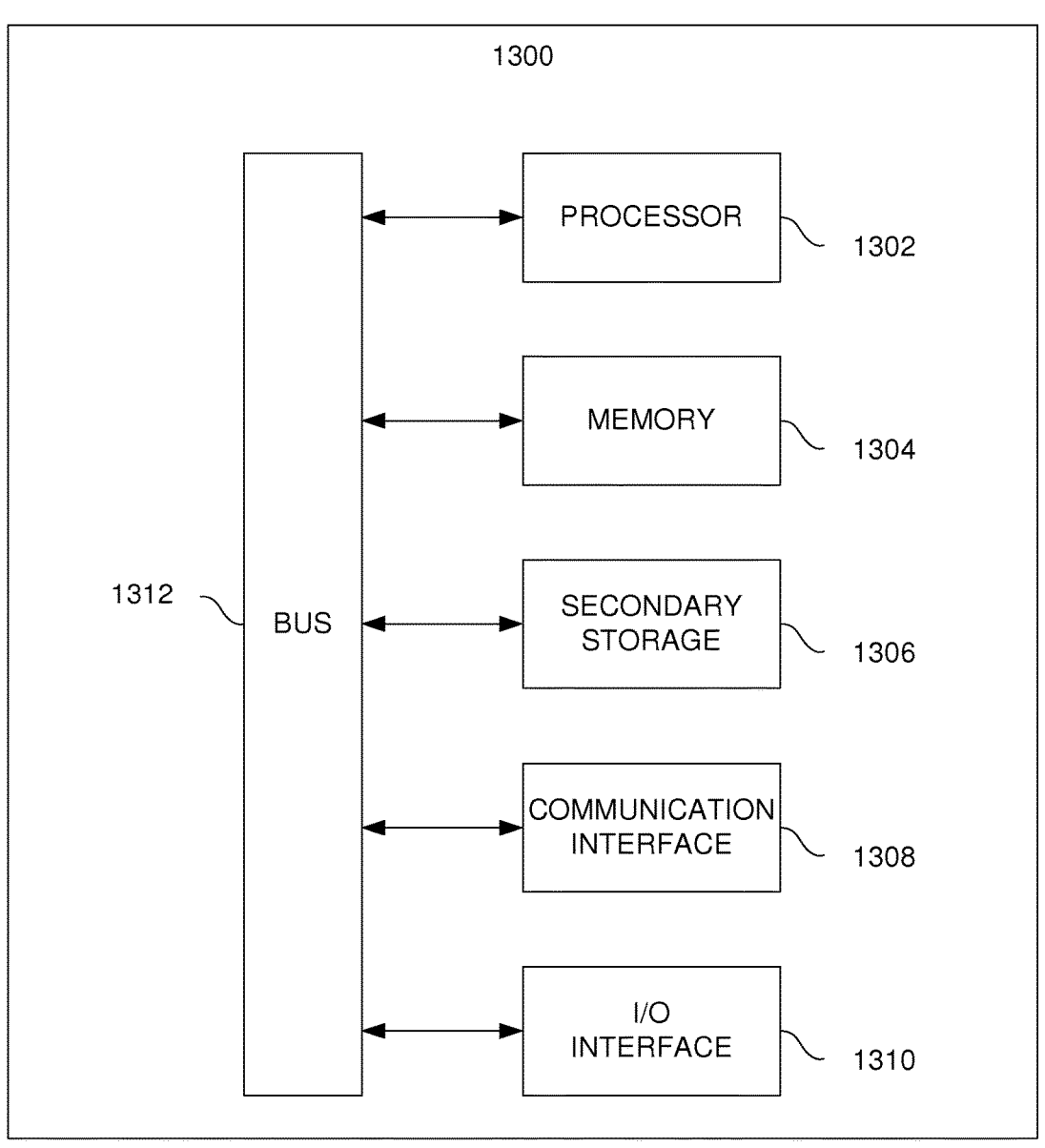
FIG. 13 illustrates an exemplary system, in accordance with one embodiment.

FIG. 13 illustrates an exemplary system 1300, in accordance with one embodiment. As an option, the system 1300 may be implemented in the context of any of the devices of the network architecture 1200 of FIG. 12. Of course, the system 1300 may be implemented in any desired environment.

As shown, a system 1300 is provided including at least one central processor 1302 which is connected to a communication bus 1312. The system 1300 also includes main memory 1304 [e.g. random access memory (RAM), etc.]. The system 1300 also includes a communication interface 1308 and a display 1310. Further, although not shown, the system 1300 may include a graphics processor.

The system 1300 may also include a secondary storage 1306. The secondary storage 1306 includes, for example, a hard disk drive and/or a removable storage drive, representing a floppy disk drive, a magnetic tape drive, a compact disk drive, etc. The removable storage drive reads from and/or writes to a removable storage unit in a well known manner.

Computer programs, or computer control logic algorithms, may be stored in the main memory 1304, the secondary storage 1306, and/or any other memory, for that matter. Such computer programs, when executed, enable the system 1300 to perform various functions (as set forth above, for example). Memory 1304, storage 1306 and/or any other storage are possible examples of non-transitory computer-readable media. It is noted that the techniques described herein, in an aspect, are embodied in executable instructions stored in a computer readable medium for use by or in connection with an instruction execution machine, apparatus, or device, such as a computer-based or processor-containing machine, apparatus, or device. It will be appreciated by those skilled in the art that for some embodiments, other types of computer readable media are included which may store data that is accessible by a computer, such as magnetic cassettes, flash memory cards, digital video disks, Bernoulli cartridges, random access memory (RAM), read-only memory (ROM), and the like.

As used here, a "computer-readable medium" includes one or more of any suitable media for storing the executable instructions of a computer program such that the instruction execution machine, system, apparatus, or device may read (or fetch) the instructions from the computer readable medium and execute the instructions for carrying out the described methods. Suitable storage formats include one or more of an electronic, magnetic, optical, and electromagnetic format. A non-exhaustive list of conventional exemplary computer readable medium includes: a portable computer diskette; a RAM; a ROM; an erasable programmable read only memory (EPROM or flash memory); optical storage devices, including a portable compact disc (CD), a portable digital video disc (DVD), a high definition DVD (HD-DVD™), a BLU-RAY disc; and the like.

It should be understood that the arrangement of components illustrated in the Figures described are exemplary and that other arrangements are possible. It should also be understood that the various system components (and means) defined by the claims, described below, and illustrated in the various block diagrams represent logical components in some systems configured according to the subject matter disclosed herein.

For example, one or more of these system components (and means) may be realized, in whole or in part, by at least some of the components illustrated in the arrangements illustrated in the described Figures. In addition, while at least one of these components are implemented at least partially as an electronic hardware component, and therefore constitutes a machine, the other components may be implemented in software that when included in an execution environment constitutes a machine, hardware, or a combination of software and hardware.

More particularly, at least one component defined by the claims is implemented at least partially as an electronic hardware component, such as an instruction execution machine (e.g., a processor-based or processor-containing machine) and/or as specialized circuits or circuitry (e.g., discreet logic gates interconnected to perform a specialized function). Other components may be implemented in software, hardware, or a combination of software and hardware. Moreover, some or all of these other components may be combined, some may be omitted altogether, and additional components may be added while still achieving the functionality described herein. Thus, the subject matter described herein may be embodied in many different variations, and all such variations are contemplated to be within the scope of what is claimed.

In the description above, the subject matter is described with reference to acts and symbolic representations of operations that are performed by one or more devices, unless indicated otherwise. As such, it will be understood that such acts and operations, which are at times referred to as being computer-executed, include the manipulation by the processor of data in a structured form. This manipulation transforms the data or maintains it at locations in the memory system of the computer, which reconfigures or otherwise alters the operation of the device in a manner well understood by those skilled in the art. The data is maintained at physical locations of the memory as data structures that have particular properties defined by the format of the data. However, while the subject matter is being described in the foregoing context, it is not meant to be limiting as those of skill in the art will appreciate that various of the acts and operations described hereinafter may also be implemented in hardware.

To facilitate an understanding of the subject matter described herein, many aspects are described in terms of sequences of actions. At least one of these aspects defined by the claims is performed by an electronic hardware component. For example, it will be recognized that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

Figure 14:
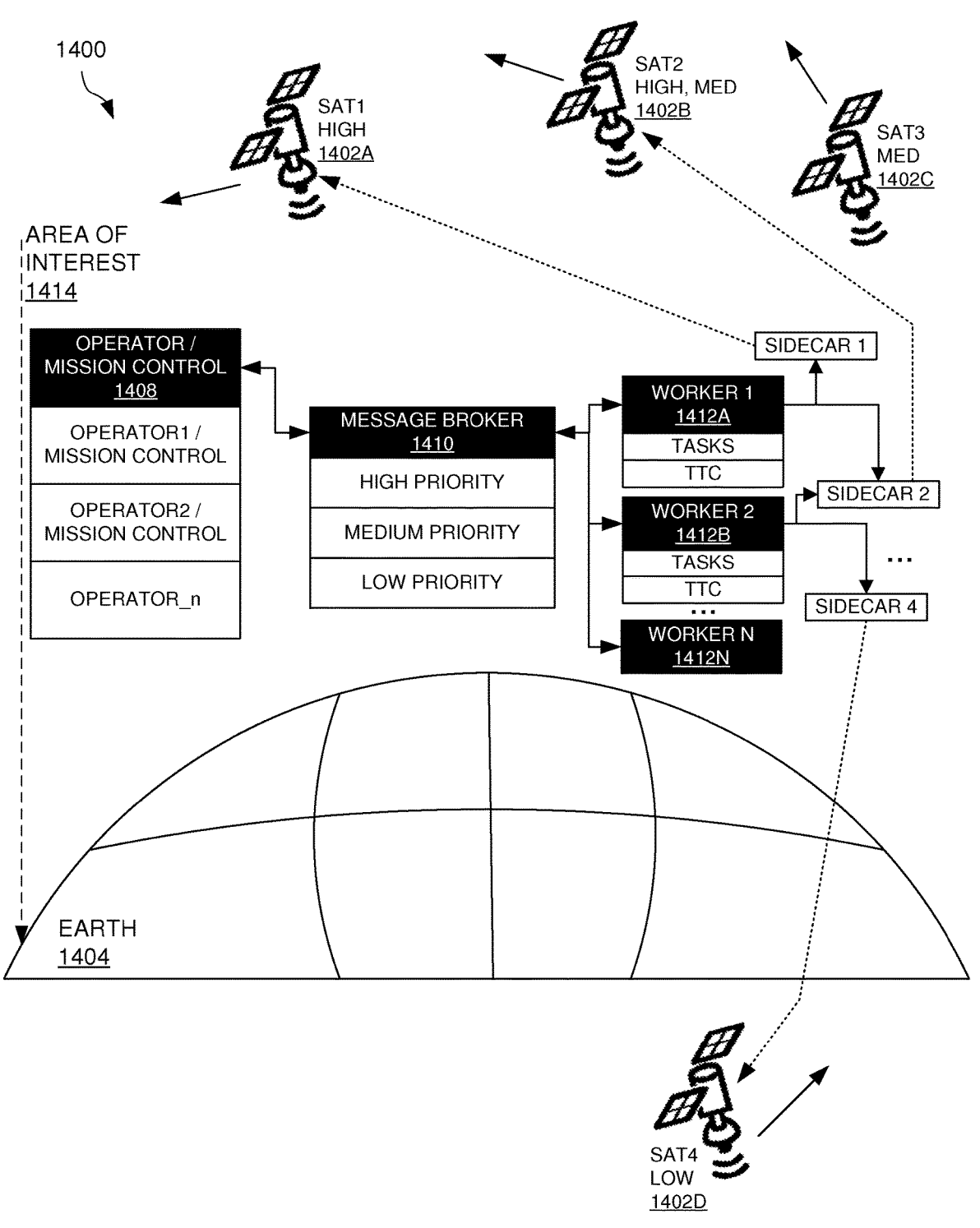
FIG. 14 shows a system for prioritization of tasks, in another embodiment.

FIG. 14 shows a depiction 1400 of a system for prioritization of tasks, in another embodiment. As an option, FIG. 14 may be implemented in the context of any one or more of the embodiments set forth in any previous and/or subsequent figure(s) and/or description thereof. Of course, however, FIG. 14 may be implemented in the context of any desired environment. Further, the aforementioned definitions may equally apply to the description below.

As shown, the depiction 1400 shows prioritization of tasks. For example, tasks may be prioritized by human operators, mission planning software, etc. to achieve timely completion based on satellite availability and satellite orbit across a constellation. High priority, medium priority and low priority tasks may be scheduled for different satellites based on orbit and business customer requirements and remuneration. Such tasks may be in relation to an area of interest (AOI) 1414 on the earth 1404, and controlled by an operator and/or mission control 1408 (including any number of operators and/or mission control centers). The message broker 1410 may be in communication with the operator/mission control 1408 to manage tasks (and its associated priority).

In one embodiment, three task priorities may be used—High, Medium and Low priorities, as managed by the message broker 1410. However, it is acknowledged that any prioritization of tasks (in terms of priority levels) may be preconfigured and determined as needed.

Further, in one embodiment, high priority and medium priority tasks, as managed by the message broker 1410, may be designated for satellites that are in transit over the AOI within a short time (e.g. 1 day or less for high priority, under 3 to 5 days for medium priority, etc.). Satellites in orbits that are unable to transit over AOI due to any reasons may be scheduled with low priority tasks.

It is recognized that tasks may be switched and their priority changed based on a variety of factors (such as but not limited to age of the task, the expected time of completion, availability of other satellites, human designated change in priority, etc.).

Further, as an example, satellite SAT4 may be in an orbit that may take several days or weeks to transit over the AOI shown, and hence it is not designated to survey that AOI, and instead, it is given some other low priority survey task (as an option). Several operators are shown providing tasks as commands to a message broker 1410 via the operator/mission control 1408 (and/or command interpreter and mission planner as disclosed hereinabove). The message broker 1410 may maintain a variety of priority queues (such as low, medium, high, etc.) to receive and/or hold the tasks. The message broker 1410 may enqueue a set of task commands (which may be referred to as a task) into a designated queue in a worker component (shown as various workers, WORKER 1 1412A, WORKER 2 1412B, WORKER N 1412N, etc.) where, as one example the tasks may be allocated to a WORKER1, based on whether the task is a mission administration task (such as a telemetry, tracking and control command (TTC) task), a mission planning task (e.g., aerial survey task), etc. As shown, other tasks are assigned by the message broker 1410 to various other workers. Further, the workers 1412A, 1412B, 1412N may each be in communication with one or more sidecar proxies, which in turn, may be used to communication directly with one or more satellites, including but not limited to SAT1 1402A (with a high designated priority), SAT2 1402B (with a high and medium designated priority), SAT3 1402C (with a medium designated priority), and/or SAT 4 1402D (with a low designated priority). It is to be appreciated that the priority designation may be a reflection of the particular satellite within the context of an AOI, and/or a reflection of the task allocated to the satellite. Thus, in this manner, a satellite that will not pass over an AOI may be designated a low priority task (in view of its lack of passing over the AOI), whereas a satellite that does pass directly over an AOI may be designated a high priority task (in view of its direct passing over the AOI). In this manner, therefore, tasks and satellites may be prioritized and/or may relate in some manner to the AOI. It should be noted that AOI alone may not determine a priority of a task, and other considerations like time of passage of a satellite over a ground station and imminence of the passage may also affect the priority of a task.

In one embodiment, the worker components (as disclosed in FIG. 14) may maintain at least two queues—one MP tasks queue and another TTC queue for MA tasks. A worker can use flight dynamics software to determine suitable satellite trajectories and reassign a task based on its priority, to an appropriate satellite just prior to the satellite's transit over a ground station and send the task commands as OBC commands to a sidecar proxy associated with the satellite for encryption, compliance check and other processing. The sidecar proxy sends the commands as one or messages to the designated ground station to relay the messages to the satellite. The process, as disclosed herein, may further increase the availability of satellites to complete one or more tasks.

It is to be appreciated that the particular configuration of the context for FIG. 14 is envisioned as just one possible set of conditions. Such disclosure of particular arrangements therefore is not to be construed as limiting to only such disclosure.

FIG. 15 shows a method 1500 for message passing, in another embodiment. As an option, FIG. 15 may be implemented in the context of any one or more of the embodiments set forth in any previous and/or subsequent figure(s) and/or description thereof. Of course, however, FIG. 15 may be implemented in the context of any desired environment. Further, the aforementioned definitions may equally apply to the description below.

As shown, the method 1500 shows one embodiment of a flow diagram that illustrates the command, control and response flow via message passing in a distributed system of satellites, ground stations, mission control, message brokers, mission administrators, operators, mission planners, simulators, etc. An operator may define an area of interest (AOI) and/or a polygon of interest and may use a declarative infrastructure to create a task (e.g. such as use of a camera to survey polygon area on earth, etc.) and provides it to a command interpreter for mission planning. See operation 1502. The task is converted into a series of commands to the flight dynamics software module and the mission planner. The flight dynamics software may receive the task (as commands), create one or more tiles for survey, and determine transit related information (such as transit times, elevation, ground aperture, AOS, LOS, TCA, etc.) of satellites in, e.g., a constellation transiting over the tiles of the AOI in the next 30 days or so and provides this data to the mission planner software. See operation 1504. Of course, the task may encompass any preconfigured geographic area (tile) and time period.

In one embodiment, the mission planner software may select the best days and times for task execution based on two or more levels of priority (or any combination of levels of priority). See operation 1506. For example, in one embodiment, three priorities (high, medium, low) may be used. Additionally, high priority, medium priority and low priority tasks may be identified (tagged) by task identifiers and may be scheduled for different satellites based on task priorities, satellite orbit, and/or business customer requirements and remuneration (as described within the context of FIG. 14).

In one embodiment, the MP may plan ground station transit for the tasked satellites, and use a one-click mechanism to transfer the task/command set to the mission control software. See operation 1508. The mission planner may also receive telemetry, tracking and control command (TTC) tasks (as commands) from a mission administrator. The MA may plan and/or monitor the health of one or more satellites (e.g. temperature, voltage/charge of the battery, data storage capacity, telemetry data, etc.), and may plan action(s) to complete the task/command at an available ground stations over which one or more satellites are expected to transit. See operation 1516. The MA may provide the task commands to MP which may then transfer the task/command to mission control with appropriate designation. The mission control may plan ground station transit for the tasked satellites for payload data download and/or TTC. See operation 1510.

In one embodiment, the mission control may receive all commands and create a priority based task set of OBC commands using micro-batching and smart batching (e.g., sizing up the command sets correctly to complete transmission to satellite for execution within the available time of transit and ground aperture) and transfer them to the message broker's prioritized master queue. The message broker may enqueue tasks as OBC command sets into appropriate worker's queues (such as when satellites approach certain appropriate ground stations). See operation 1512. A worker may use flight dynamics software module to refresh any flight dynamics calculations to determine the best course of action and may re-designate the satellite for completing a task at the last minute. See operation 1514. Tasks may be enqueued into specific worker queues. For example, per operation 1520A, tasks may be enqueued into WORKER1 queues. Additionally, the worker queues may be then assigned to a sidecar proxy (such as Sidecar 1 1522A). In one embodiment, MP aerial survey and similar tasks may be reassigned. This kind of re-assignment of a satellite is shown via the dashed line from operation 1520A to operation 1522B. Such reassignment may include worker1 re-assigning a task to a satellite sat2 via a sidecar proxy sidecar2.

Mission administration based TTC commands may be specific to a particular satellite. In this manner, one set of TTC commands intended for a first satellite may not be executed on another satellite because such TTC commands are satellite specific task/commands. As such, if necessary, MA tasks may be configured to wait for a next transit of the satellite at a ground station (either same or another ground station) from which they can beam micro-batch commands to satellites. This is one example of fault-tolerant smart batching. It is envisioned that other configurations may be equally applicable (and equally allow for smart batching).

In one embodiment, tasks enqueued into a worker's queue where the worker dies subsequently, or tasks which fail to proceed forward for any reason may be returned to the message broker, are marked incomplete in the message broker, etc. Such tasks may be re-executed. See operation 1518.

In one embodiment, commands of tasks sent from workers to sidecar proxies may be encrypted, processed, and/or sent to ground stations which beam them to the designated satellites upon their arrival/transit as determined by acquisition of signal (AOS). MA commands may be prioritized so that their response from a satellite can also be received right away by the ground station. Further, the response tagged by the task identifier may be sent on to a designated sidecar proxy. The sidecar proxy may return the response to the designated worker which may send the response to the result backend software component. Ground failures (such as but not limited to failure of ground stations, loss of connectivity, and/or loss of signal (LOS)) may be marked as ground-failures and messaged to the message broker for re-execution/re-starting. See operation 1518 (option failure).

In one embodiment, response(s) from a satellite (including failures on the satellite side due to execution failure of a set of command(s) and/or responses that are result data or result status) may be sent to mission control for further action. See operation 1518 (option results/responses). Based on the refreshed flight dynamics calculations (per operation 1514), tasks may be enqueued into WORKER2 queues, or otherwise may be returned on failures (see operation 1520B), and/or tasks enqueued into WORKER4 queues may be delivered to an associated sidecar (such as sidecar 4 1522C).

In various embodiments, the tasks sent to a sidecar proxy may be provided to a ground station which may then forward on the commands. See operation 1524A. Such commands may then be beamed to a satellite for task execution by priority, and responses/data may be beamed back. See operation 1526A. In one embodiment, a command may be sent from a first ground station to a first satellite, and a response may be sent from the first satellite back to the first ground station. Alternatively, the first satellite may send a response back to an alternative ground station, such as ground station 2 (operation 1524B). The ground station 2 (operation 1524B) may forward and/or beam tasks by priority to a second satellite (per option 1526B), and a response may be provided back to any ground station, including a third ground station (which may return the responses by second satellite based on tasks previously sent by the second ground station) (see operation 1524C). Additionally, the ground station 2 1524B may receive commands from the sidecar 2 1522B (and/or any other sidecar) for sending to a satellite.

The ground stations may return responses back to the sidecar, which may, in turn, provide feedback to the WORKER queue, which in turn may report failures or success back to the ground station and/or the message broker for action as needed. In this manner, tasks may be assigned to specific WORKERS, sidecar proxies, allocated to a ground station, and then communicated to a satellite, which in response, the satellites may deliver a response which may be provided to the original originating ground station, and/or delivered to an alternative new ground station (different from the original sending ground station source).

In various embodiments, within the context of repurposing/rebalancing tasks, the workers can re-assign MP tasks at the last minute to a different satellite (via their sidecar proxy) than previously chosen. This may happen for a variety of reasons including, but not limited to, loss of health of a satellite (loss of power in the satellite, bad elevation of the satellite, bad attitude of the satellite, etc.). As discussed hereinabove, tasks may be reassigned from one sidecar to another. This may increase the availability of satellites as a resource in a constellation. This re-assignment may also be done to reduce the number of commands a satellite may need to execute at any time. Aerial survey tasks/commands may be reassigned at the last moment.

Besides reassigning satellites, the reassignment of ground stations for receiving the result data for an MP task can also be performed by sending commands via a first ground station GS1 and receiving the result response from the satellite via different second ground station GS2 at a later time (such as shown within the context of FIG. 15). For example, if a task is in a satellite queue, but a satellite 'disappears' (and/or loses connection) then the worker queue entry may time out and the task may then be put back on a different satellite's queue for execution/completion.

Figure 16A:
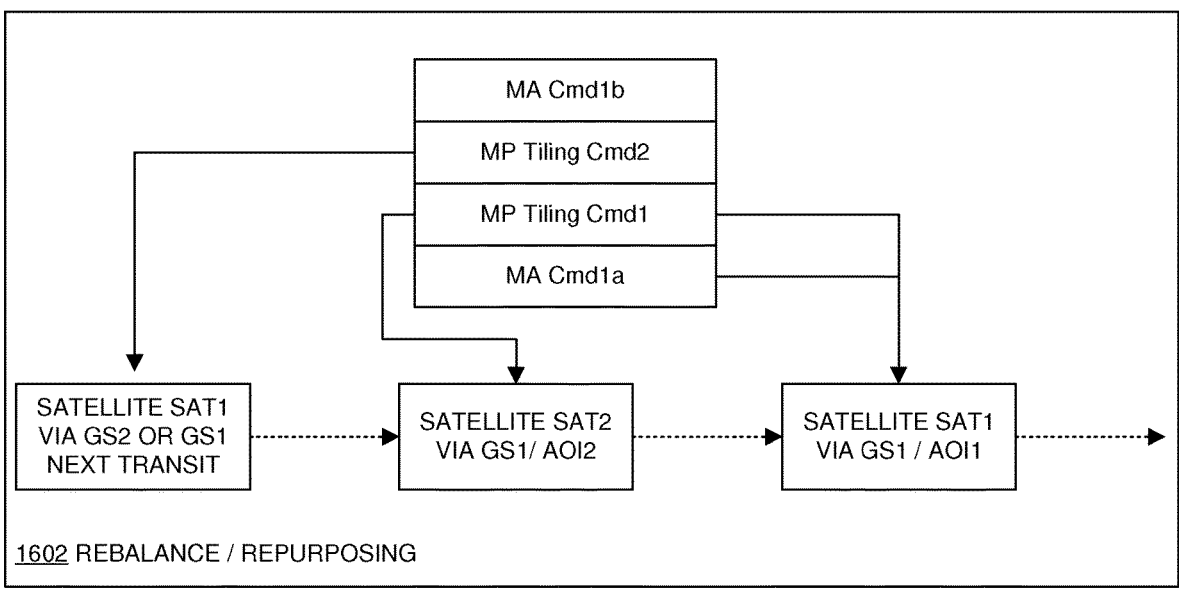
FIGS. 16A and 16B show a system for re-assignment/re-purposing of tasks, in another embodiment.
Figure 16B:
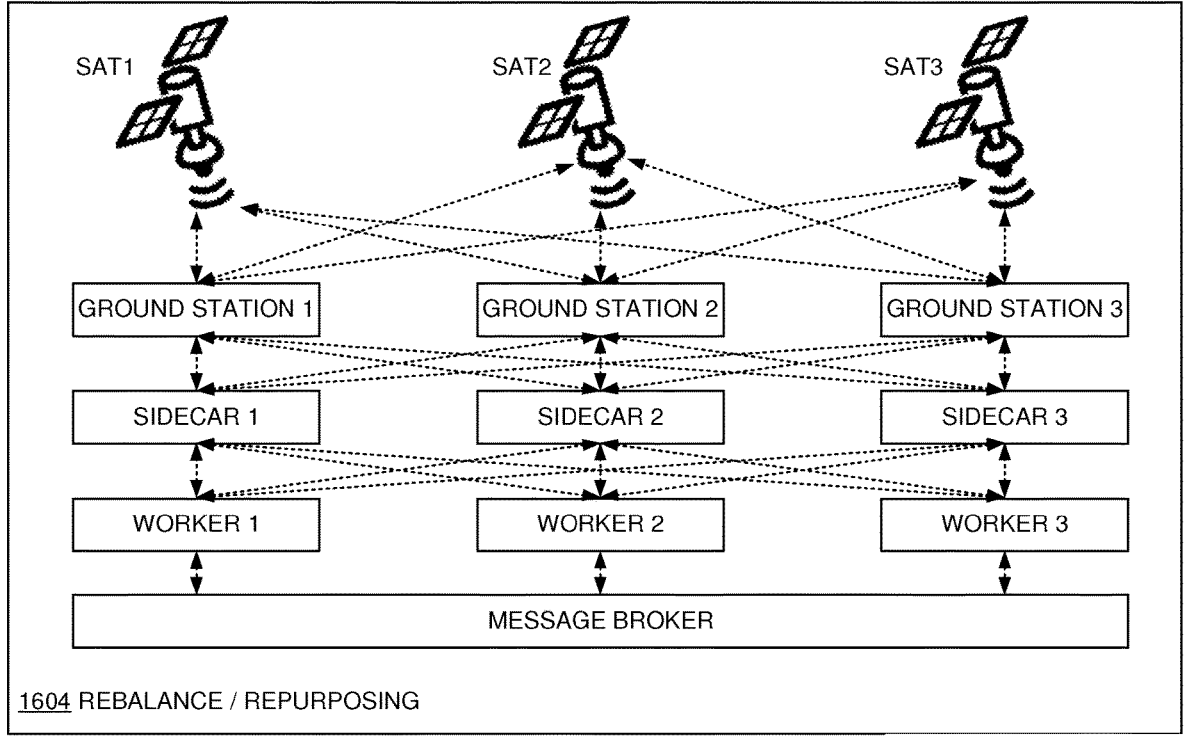

FIGS. 16A-16B show a system for re-assignment/re-purposing of tasks, in another embodiment. As an option, FIGS. 16A-16B may be implemented in the context of any one or more of the embodiments set forth in any previous and/or subsequent figure(s) and/or description thereof. Of course, however, FIGS. 16A-16B may be implemented in the context of any desired environment. Further, the afore-mentioned definitions may equally apply to the description below.

In one embodiment, if there are not enough satellites for a set of tasks, a new satellite can be commissioned and the task may enter the framework with an additional worker and an additional corresponding sidecar, as shown in the rebal-ance/repurposing 1604. This is one example where the declarative infrastructure is structured to conveniently add additional satellite resources and ground stations to the distributed infrastructure. Similarly, a non-functional satel-lite or dysfunctional satellite can be temporarily or perma-nently removed from the distributed infrastructure respec-tively.

The distributed system of satellites in a constellation and the ground stations and mission control may be configured to allow re-assignment/re-purposing of satellites to increase availability, as shown in rebalance/repurpose 1604.

As shown in the embodiment of rebalance/repurposing 1602, a tiled survey task that cannot be completed by a first satellite may completed by a second satellite. Task com-mands (e.g, MP tiling Cmd1, MP tiling Cmd2) in a worker's queue may be completed by the first satellite SAT1 and then by the second satellite SAT2 in order to complete a defined task. However, mission administration task commands (e.g., MA Cmd1a, MA Cmd1b, etc.) may be completed by the satellite they are designated for, since such commands may be particular to a satellite. In this example, the second (MA Cmd1b) command cannot be completed during a first transit over a ground station GS1 of the first satellite SAT1. Thus, it may be scheduled to complete when the first satellite (satellite SAT1) has a next transit over a ground station, which can be a second ground station GS2 (and re-routing may be handled automatically) or it can be during the next transit of satellite SAT1 over the first ground station GS1.

If satellite SAT1 is unable to handle the task then WORKER1 may look for another satellite within a set distance that can receive the task and complete with the same priority by a certain time, and the WORKER may request a re-run of the flight dynamics simulation with the new/repurposed satellite. If no suitable satellite can be substituted, then the task may be returned to the message broker task master queue. The human operator can intervene and manage queues (such as if there are too many retries or failures). As such, the automatic allocation of tasks may occur without much human intervention, thereby function in a fault-tolerant manner.

Further, rebalance/repurposing 1604 shows the fault-tol-erance and load-balancing capabilities. For example, rebalance/repurposing 1604 includes message brokers, workers, sidecar proxies, ground stations and satellites which may communicate via message passing. Additionally, tasks and commands may be scheduled, re-scheduled, routed, re-routed at the last moment (or any desired timeframe) prior to final communication with the satellites. For example, if a task is in a satellite queue, but the satellite 'disappears' (and/or loses connection) then the worker queue entry may time out and the task may then be put back on a different satellite's queue.

In one embodiment, satellites may also be re-assigned for tasks enqueued, subject to certain constraints (such as but not limited to compliance with regulations, task types, etc.). Further, some tasks may be enqueued to specific types of satellites if customer so demands based on feature availabil-ity.

In one embodiment, commands and tasks that fail on a satellite may be retried via the message broker on the same satellite but at a different ground station with better elevation (such as based on satellite angle to ground station with respect to the ground position, such as 90 degrees may refer to an angle overhead and the best elevation for signal reception), at a more suitable latitude-longitude pair, satel-lite attitude, and longer ground aperture with regard to the orbit of the satellite, etc.

Figure 17:
FIG. 17 illustrates a system for tracking a satellite over an interval of time, in another embodiment.

FIG. 17 illustrates a system 1700 for tracking a satellite over an interval of time. As an option, the system 1700 may be implemented in the context of any one or more of the embodiments set forth in any previous and/or subsequent figure(s) and/or description thereof. Of course, however, the system 1700 may be implemented in the context of any desired environment. Further, the aforementioned defini-tions may equally apply to the description below.

Referring to the map illustration of system 1700, the illustration provides a visual representation of the ground track of a satellite. The map includes multiple ground stations 1702 distributed across different regions. These ground stations 1702 may be strategically located to maxi-mize the coverage and communication with the satellites in the constellation. In some aspects, the ground stations 1702 may include various components, such as a communication system, a power system, and a control system, that facilitate communication with the satellites and manage the reception and transmission of signals and data.

An area of interest 1704 is marked on the map of the system 1700, indicating a specific region that the satellite is tasked to monitor or survey. The area of interest 1704 may be defined based on various factors, such as the mission objectives, the capabilities of the satellites, the operational constraints, etc. Additionally, the area of interest 1704 may be selected based on an intent-based instruction. In some cases, the area of interest 1704 may include various geo-graphical features, such as landforms, bodies of water, and man-made structures, that are relevant to the mission objec-tives and/or the intent-based instruction.

The current path 1706 of the satellite is shown with a dotted line, while the future path 1708 is indicated with a long dash line. The current path 1706 represents the trajec-tory of the satellite at the present time, while the future path 1708 represents the predicted trajectory of the satellite based on various factors, such as the current position and velocity of the satellite, the gravitational forces acting on the satellite, the operational constraints of the satellite, etc., all of which may be more accurately predicted and modeled using machine learning. The depiction of the current path 1706 and the future path 1708 can provide valuable information for mission planning and control, such as determining the timing and scheduling of tasks, predicting the visibility conditions, and planning the communication with the satellite.

As shown, the area of interest 1704 is shown within the trajectory map of the future path 1708. It is to be appreciated that the area of interest may be at any current or future location of a trajectory of a satellite.

As shown, tracking a satellite over an interval of time may be performed as a ground track computed using, in one embodiment, the most recent TLE parameters. In one embodiment, the ground track may shift over time on multiple transits around a location as TLE parameters change over time. Such a shift may be due to the instantaneous dynamics and kinematics of the satellite or due to longer-term seasonal variations due to the "precision" of the earth and other considerations. In addition, the area of interest (AOI) that is within the ground track at a point in time may be surveyed effectively during transit or during a near term repetition (i.e., within one or two days). As such, however, an AOI outside of the ground track that may be based on the latest TLE at an instance that is further away from the ground track, it may become extremely difficult and computationally expensive to compute the transit time of the satellite over the AOI at a distant point in the future. Additionally, similar or identical considerations may apply for the satellite transit over a ground station (GS), wherein the same above-stated problems may need to be addressed because commands may need to be sent to the satellite and data may need to be downloaded. It should be noted that the system 1700 may address this problem for one or more satellites in a constellation.

As illustrated in system 1700, a ground station GS1 of the ground stations 1702 appears adjacent to the satellite ground track (via the current path 1706) while ground station GS2 of the ground stations 1702 and the AOI 1704 may not intersect with the current ground track (the current path 1706) but may intersect with a future ground track (the future path 1708). It is to be appreciated that one of many ground stations may intersect the ground track (e.g., lie within the ground track) a day or two into the future. An issue exists, however, wherein the exact times and durations of transit over any one or more of the ground stations must be correctly and efficiently determined, so that a correct set and the correct number of commands may be prepared to be uploaded to the satellite in question. In addition, a user may determine one or more transits for the purpose using machine learning that predicts a few suitable transits (such as the future path 108) that are verified using flight dynamics simulation in advance.

As such, the system 1700 shows that a future path of a satellite may be determined with greater accuracy and precision. In some aspects, the map illustration of the system 1700 may be generated using various mapping and visualization tools, such as geographic information system (GIS) software, computer-aided design (CAD) software, and data visualization software. The map illustration 1700 may also be updated in real-time or near real-time to reflect the current position and trajectory of the satellite, the status of the ground stations, and the changes in the area of interest. This can provide operators with up-to-date and accurate information for managing and controlling the satellite constellation.

Figure 18:
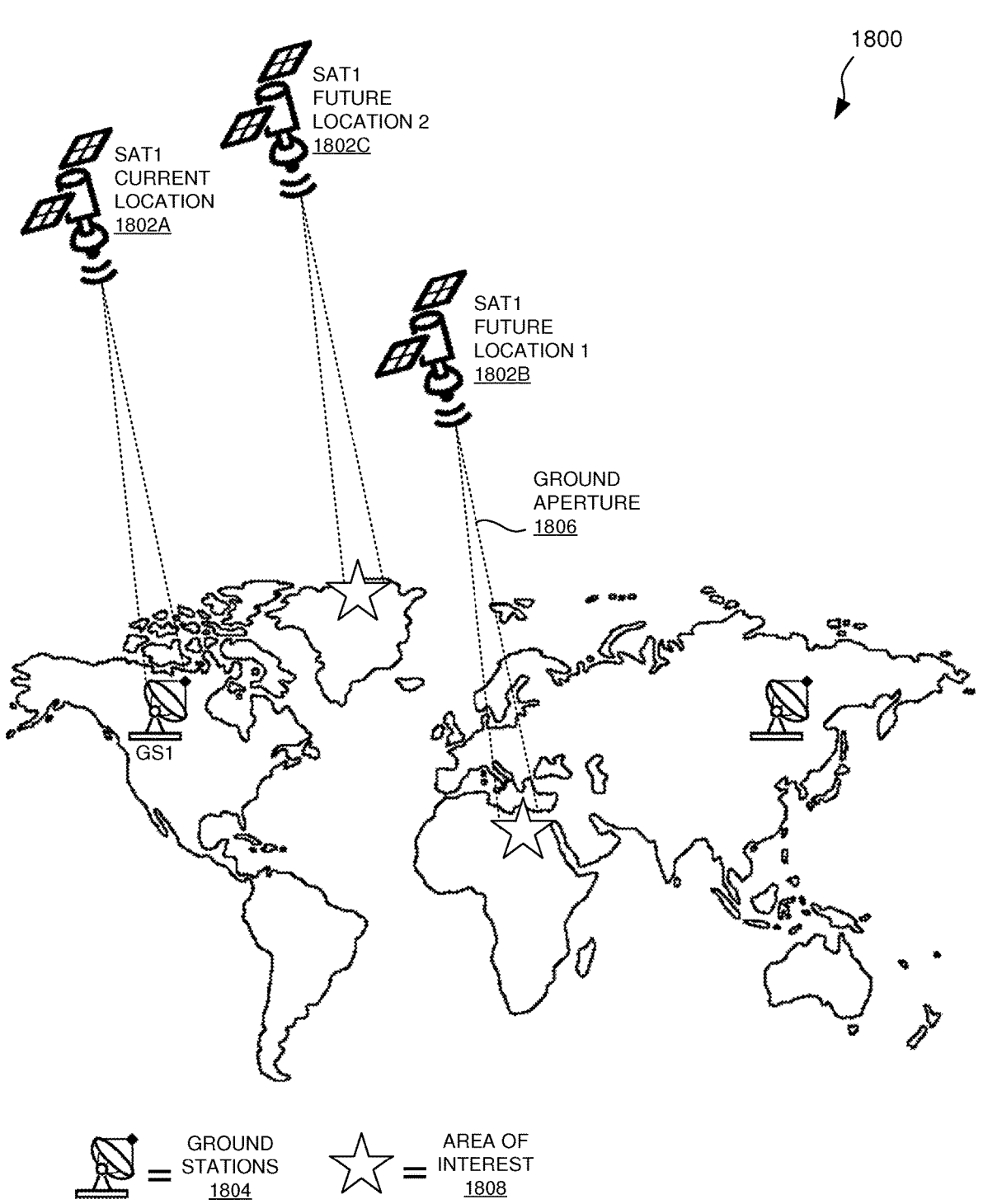
FIG. 18 illustrates a system for determining a future time and date where a satellite passes over one or more AOIs, in another embodiment.

FIG. 18 illustrates a system 1800 for determining a future time and date where a satellite passes over one or more AOIs. As an option, the system 1800 may be implemented in the context of any one or more of the embodiments set forth in any previous and/or subsequent figure(s) and/or description thereof. Of course, however, the system 1800 may be implemented in the context of any desired environment. Further, the aforementioned definitions may equally apply to the description below.

Referring to the satellite constellation of the system 1800, the system may include one or more satellites in a constellation. The current location of SAT1 1802A and future locations of SAT1, including the first future location 1802B and the second future location 1802C, are determined based on various factors, such as the current position and velocity of SAT1, the gravitational forces acting on SAT1, the operational constraints of SAT1, TLE parameters, etc., all of which may be more accurately predicted and modeled using machine learning. As such, the determination of the current and future locations of SAT1 may be performed using various algorithms and models, such as orbital mechanics models, flight dynamics models, and machine learning models.

In some aspects, the ground stations 1804 may be strategically located at various geographical locations on Earth to maximize the coverage and communication with the satellites in the constellation. Each ground station 1804 may include various components, such as a communication system, a power system, and a control system, that facilitate communication with the satellites and manage the reception and transmission of signals and data.

The ground aperture 1806 represents the area on Earth that can communicate with the satellites. The size and shape of the ground aperture 1806 may depend on various factors, such as the altitude and inclination of the satellites, the geographical location of the ground stations, and the communication capabilities of the satellites and the ground stations.

In one embodiment, the areas of interest 1808 may include specific regions on Earth that the satellites are tasked to monitor or survey. The areas of interest 1808 may be defined based on various factors, such as the mission objectives, the capabilities of the satellites, the operational constraints, the intent-based instructions, etc. In some cases, the areas of interest 1808 may include various geographical features, such as landforms, bodies of water, and man-made structures, that are relevant to the mission objectives.

In some cases, the satellite constellation management system 1800 may use machine learning algorithms to optimize the assignment and execution of tasks. For example, the system may use a machine learning model trained on historical satellite data to predict the future locations of the satellites, optimize the scheduling of tasks, or detect anomalies in the satellite data. This can help to ensure that the tasks are completed efficiently and effectively, as the tasks are assigned and executed in a way that maximizes the use of the satellites' resources and minimizes the time taken to complete the tasks.

In some aspects, the system 1800 may provide fault tolerance by allowing remote rescheduling or reset of a satellite On-Board Computer (OBC) at another compliant ground station when a satellite passes over it. This can ensure that the satellite operations continue smoothly even in the event of a failure or disruption in the communication with a particular ground station.

Furthermore, the system 1800 may include a virtual satellite simulation infrastructure for creating new satellites to study what-if scenarios to pre-determine the trajectories before launch for new satellites or the trajectories for existing satellites before a specific date. This can help in better planning and management of the satellite constellation.

In various embodiment, the system 1800 may further address known issues (similar in nature to system 1700) with determining a time and date upon which a satellite may pass over one or more AOIs given the satellite's current/instantaneous location. In an embodiment, such a future date and time is to be extrapolated using the satellite's current/instantaneous location, which may be performed using machine learning. It should be noted that the system 1800 may address this problem for one or more satellites in a constellation. For example, a satellite may be currently/instantly in transit over a ground station GS1, and two unknown values may need to be determined for 1) a location of the satellite at a time "FUTURE1," and 2) another time "FUTURE2," wherein the satellite may pass over one or more AOIs.

In one embodiment, the instant disclosure describes a machine learning mechanism that may estimate a location, time, and date associated with FUTURE1 (SAT Future Location 1 1802B) and FUTURE2 (SAT1 Future Location 2 1802C), each associated with a respective AOI. In operation, all predicted/generated estimates may be verified using flight dynamics simulations recorded a few hours or even a full day or so in advance. It should be noted that flight dynamics simulation accuracy may decrease as the temporal separation between the current/instantaneous location and one or more future locations (1802B, 1802C, for example) increases. As such, a machine learning based prediction model working from prior data may be significantly more efficient. In operation, it is to be appreciated that, even if the satellite passes over an AOI or a GS multiple times, only a subset of the transit data may be useful due to the fact that the orientation of a survey camera must be correct to support good data collection and recording. Further, it should be noted that the angle of elevation from a GS must be closer to perpendicular to maximize the potential for reliable data exchange and recording between the satellite and a GS.

FIGS. 19A and 19B illustrate example scenarios 1900 and 1901 for the elevation profile of a satellite in transit over a ground station. As an option, the scenarios 1900 may be implemented in the context of any one or more of the embodiments set forth in any previous and/or subsequent figure(s) and/or description thereof. Of course, however, the scenarios 1900 may be implemented in the context of any desired environment. Further, the aforementioned definitions may equally apply to the description below.

Referring to the scenario 1900 and/or scenario 1901 each showing an elevation profile graph, the graphs illustrates the elevation in degrees over time from the acquisition of signal (AOS) to the loss of signal (LOS). The elevation profile graph provides a visual representation of the satellite's elevation as it transits over a ground station. The elevation is plotted on the y-axis, while the time since the acquisition of signal (AOS) is plotted on the x-axis. The graph shows how the elevation changes over time, with the peak of the graph representing the time of closest approach (TCA), when the satellite is at its maximum elevation.

In some aspects, the elevation profile graph of the of scenario 1900 and/or scenario 1901 may be divided into two regions: Region 1 and Region 2. Region 1 represents the time intervals where communication with the satellite is not possible, while Region 2 represents the useful regime where communication is established. The division between Region 1 and Region 2 may be determined based on various factors, such as the elevation angle threshold for communication, the signal strength, the operational constraints of the satellite and the ground station, etc.

In some cases, the elevation profile graph of scenario 1900 and/or scenario 1901 may be used to plan and schedule satellite operations. For example, the graph may be used to determine the optimum times for sending commands to the satellite, receiving data from the satellite, or performing other operations that require communication with the satellite. The graph may also be used to monitor the performance of the satellite and the ground station, and to detect any anomalies or issues that may affect the communication.

In some aspects, the elevation profile graph of scenario 1900 and/or scenario 1901 may be generated using various algorithms and models, such as orbital mechanics models, flight dynamics models, and signal propagation models. The graph may also be updated in real-time or near real-time to reflect the current position and velocity of the satellite, the current conditions at the ground station, and other relevant factors.

In some cases, the elevation profile graph of scenario 1900 and/or scenario 1901 may be displayed on a user interface, such as a mission control console, a ground station monitor, or a mobile device. The graph may be accompanied by various controls and indicators that allow operators to interact with the graph, adjust the parameters, and view additional information. The graph may also be integrated with other tools and systems, such as mission planning software, satellite control systems, and data analysis tools, to provide a comprehensive solution for managing and controlling satellite operations.

In various embodiment, the scenarios 1900 and/or 1901 show the elevation profile of a satellite in transit over a ground station as a function of time for two separate transits: TRANSIT A of the scenario 1900 and TRANSIT B of the scenario 1901. In one embodiment, REGION_1 of scenarios 1900 and 1901 may depict a time regime during which no communication with satellite is available/possible, while REGION_2 shows a time regime during which communication with a satellite has been established (also called a "Useful Regime"). In the case of scenario 1900, the time of closest approach (TCA) may be shown to fall outside the useful regime REGION_2. It should be noted that, while some communication is possible in such a scenario, the size of regime REGION_2 and the angle of elevation (shown on the y-axis) may not be optimum. Alternatively, in the case of scenario 1901, the TCA is shown to fall within the useful regime REGION_2 of the transit. Thus, the exemplary transit in scenario 1901 may be much more favorable for communication between the satellite and a GS under consideration. As such, the techniques depicted in scenarios 1900 and 1901 may allow for a machine learning model to estimate (predict or pre-determine) the time and date of transit over an AOI or a particular GS, prioritize "good" and "best" transits over less favorable transits based on respective elevation profiles and adjusted duration of passage or transit, as discussed in the context of related figures herein.

In one embodiment, the adjusted duration of passage (ADP) may be a defined portion of the time between acquisition of signal (AOS) and loss of signal (LOS). Additionally, the length of the adjusted duration of passage and elevation profile may determine both the number of commands that can be sent to the satellite and the amount of data that can be returned from the satellite. It should be noted, as well, that the respective sizes of the micro-batches of commands may be determined (predicted, estimated, or computed) using machine learning model(s) trained on prior real data from previous transits. As a result, the micro-batches of commands may then be generated and prepared for use prior to an actual target transit. This method of creating correctly sized micro-batches using machine learning is one of the methods of smart-batching. Alternately, in some aspects, smart batching may also be performed using inputs from the flight dynamics simulation.

FIGS. 20A and 20B illustrate methods 2000A and 2000B for gathering TLE and mission control data to train a machine learning model. As an option, the methods 2000A and 2000B may be implemented in the context of any one or more of the embodiments set forth in any previous and/or subsequent figure(s) and/or description thereof. Of course, however, the methods 2000A and 2000B may be implemented in the context of any desired environment. Further, the aforementioned definitions may equally apply to the description below.

Referring to the method 2000A, the process begins with gathering TLE data associated with a satellite or a satellite constellation. See operation 2002. The TLE data, which is a data format widely used to convey sets of orbital elements that describe the orbits of Earth-orbiting satellites, may be obtained from various sources, such as satellite operators, space agencies, NORAD, and/or other organizations that track and catalog space objects. The TLE data may include information such as the satellite's orbital inclination, right ascension of the ascending node, eccentricity, argument of perigee, mean anomaly, mean motion, and other relevant parameters.

The gathered TLE data is then pre-processed resulting in a standardized data set. See operation 2003. The pre-processing step may involve various operations, such as data cleaning, data transformation, and data normalization, to prepare the TLE data for further analysis and processing. For example, data cleaning may involve removing or correcting erroneous or missing data, data transformation may involve converting the data into a suitable format or scale, and data normalization may involve adjusting the values of the data to a common scale.

The standardized data set is then partitioned into a control set and a test set. See operation 2005. The control set may be used as a baseline, and thereby remain constant and unaltered to provide a standard for comparison. In contrast, the test data may be manipulated and/or used in forecasting and/or predicting TLE data.

For example, physics based flight dynamics model simulation may be applied to forecast predicted trajectory paths. See operation 2007. The flight dynamics model may be evaluated by making predictions on the test data using physics based model where an accuracy of the model may be calculated by comparing predicted labels with actual data weekly using an accuracy scoring function. See operation 2009.

In the event that the accuracy of the model is below a predetermined threshold, the method may return to operations 2007 and/or 2003 (depending on the lack of accuracy of the model). If the accuracy of the model surpasses the predetermined threshold, the method continues on to operation 2011, where the simulation model state is saved. See operation 2011. In one embodiment, the simulation model state may be saved daily, and/or saved daily after update. Further, the physics based model may be rerun for the target data generation for a target date and time. See operation 2013. Further, ranking criteria may be applied to the rerun. See operation 2015.

Referring to the method 2000B, the process begins with gathering TLE data associated with a satellite or a satellite constellation. See operation 2002. The TLE data, which is a data format widely used to convey sets of orbital elements that describe the orbits of Earth-orbiting satellites, may be obtained from various sources, such as satellite operators, space agencies, NORAD, and/or other organizations that track and catalog space objects. The TLE data may include information such as the satellite's orbital inclination, right ascension of the ascending node, eccentricity, argument of perigee, mean anomaly, mean motion, and other relevant parameters.

The gathered TLE data is then preprocessed. See operation 2004. The preprocessing step may involve various operations, such as data cleaning, data transformation, and data normalization, to prepare the TLE data for further analysis and processing. For example, data cleaning may involve removing or correcting erroneous or missing data, data transformation may involve converting the data into a suitable format or scale, and data normalization may involve adjusting the values of the data to a common scale.

In one embodiment, the operation 2004 may involve parsing data to extract relevant parameters (e.g., mean motion, first and second derivatives of mean motion, right ascension, inclination, etc.), as well as compiling a list of associated ground location (AOI or GS) coordinates from which distances between AOIs and/or GSs and a projected satellite path may be computed. Additionally, parameter values such as month, date, time of day of transit; AOS, LOS, TCA, elevation, cloud cover may be extracted therefrom. Further, distances and angles of elevation along the satellite path from one or more ground locations (AOIs or GSs) may also be computed and prepared as training and testing data set material.

The preprocessed data is standardized for feature scaling. See operation 2006. Feature scaling may include using a machine learning system to normalize the range of independent variables or features of data. This can be particularly useful when the data includes features with different scales or units, as it can help to ensure that all features contribute equally to the model's performance. The standardization process may involve various techniques, such as min-max normalization, z-score normalization, or scaling to unit length, depending on the specific requirements of the machine learning model.

The standardized data is used for machine learning model training. Sec operation 2008. The machine learning model may be any suitable type of model, such as a supervised learning model, an unsupervised learning model, a semi-supervised learning model, or a reinforcement learning model. The model may be trained using various algorithms, such as linear regression, logistic regression, decision trees, random forests, support vector machines, neural networks, or deep learning algorithms, depending on the specific task and the nature of the data.

In one embodiment, operation 2006 may involve a process wherein the data set(s) determined in operation 2004 may be split into a set of features (X) and a set of targets (Y) using processes and techniques or methods applied on data such as auto scaling, statistical scaling, normalization, etc., designed for training a predictive machine learning model as in operation 2008. In one embodiment, the auto scaling, statistical scaling, normalization processes may allow model weights to be brought within acceptable bounds (e.g., within certain delineations of data known to be in appropriate intervals (0,1) or [0,1], and so on). Examples of such feature sets (X) may include adjusted duration of passage (ADP), ratio of ADP to Total Duration of Passage (TDP), combinations of AOI+angle of elevation+time of day, and so on. In addition, targets (Y) may be a set of ranks or confidence intervals, and the target categories may be created based on one or more ranking criteria provided by a user based on the purpose served by such information. For example, in order to maximize the ratio of adjusted duration of passage to total duration of passage at available GSs in order to increase the size of the command batches for smart batching, such feature set creation may be necessary. In another example, the ranking criteria when creating target sets may serve the purpose of maximizing the angle of elevation of one or more satellites at a point inside an AOI to improve aerial survey. Further, within the functions of operation 2004, the one or more data sets may also be split into a training data set and a testing data set.

In another embodiment, a machine learning model (e.g., a Random Forest Classifier) may be trained using the training data set(s) produced previously, as in operation 2008. The resulting machine learning model may be a predictive machine learning model for classification and ranking purposes. Alternately, the machine learning model may be a generative machine learning model used for the purposes of generating hypothetical TLE data for transits in the distant future (for example, from one to two weeks, or even a few months into the future) in order to plan remote sensing missions into the future.

Per operation 2010, the trained model is evaluated by making predictions on test data and calculating the accuracy of the model by comparing predicted labels with actual labels using an accuracy scoring function. The evaluation process may involve various metrics, such as accuracy, precision, recall, F1 score, area under the ROC curve, mean squared error, or mean absolute error, depending on the specific task and the nature of the data. The evaluation process may also involve cross-validation techniques, such as k-fold cross-validation or leave-one-out cross-validation, to assess the model's performance on unseen data and to prevent overfitting.

After the final training epoch, the trained model weights are saved. See operation 2012. The model weights represent the learned parameters of the model, and they can be used to make predictions on new data. The model weights may be saved in various formats, such as binary files, text files, or database records, depending on the specific requirements of the machine learning model and the computing environment.

Next, model deployment and output generation occurs where the trained model is loaded for inference, input data is provided, and predictions are made. See operation 2014. The model deployment process may involve various steps, such as loading the model weights, initializing the model's architecture, preparing the input data, running the model's inference function, and processing the model's output. The output generation process may involve various operations, such as converting the model's output into a suitable format, visualizing the output, or integrating the output with other systems or processes.

The ranking criteria 2016 may be used to rank the predictions based on predefined metrics. The ranking criteria may involve various metrics, such as the confidence of the predictions, the relevance of the predictions, the novelty of the predictions, or other suitable metrics. The ranked predictions may be used for various purposes, such as decision making, prioritization, recommendation, or other suitable purposes. In some cases, the ranked predictions may be used to determine a list of parameters and their values such that the mission planning software/processes and the flight dynamics software/simulation quickly converge on an intended trajectory; and quickly determine the command batches and micro-batches, and the time instances to upload these command batches to satellites via available ground stations. Additionally, the ranking criteria 2016 may be fed as an input into the machine learning model training of operation 2008, the model evaluation of operation 2010, and/or the model deployment of operation 2014.

Further, based on the results of the model evaluation per operation 2010, the system may determine that the accuracy of the model is of insufficient quality, and based on such scoring, may reroute the data either back to operation 2004 (for pre-processing of the TLE data again) and/or to operation 2008 (for further training of the machine learning model). In the event that the accuracy of the operation 2010 surpasses a minimum (or predetermined) threshold, the trained model then proceeds on to operation 2012.

In various embodiment, the methods 2000A and/or 2000B may show a method for gathering TLE and mission control data to train a machine learning model which may be used to determine (predict, estimate, and/or compute) successful combinations of ground locations and date and time of transit for one or more satellites in a constellation. In an embodiment, the success of a combination is either individually determined for a specific combination, or a prioritized list of combinations may be determined given an initial list of desired ground locations. The necessary training may be performed with data from a single satellite or from all satellites in a constellation. It should be noted that such capability may be required because, in one embodiment, a GS operator or flight dynamics simulator may provide limited quantity of data (such as only two or three days of predictable events) where a satellite is to pass over a particular GS. As such, it may become imperative to predict transits taking place more than three days (perhaps even a week) into the future based on past TLE data.

In one embodiment of the learning model training process, an evaluation may be modeled by making predictions on test data using a trained model and calculating the accuracy of the model by comparing predicted labels with actual labels using an accuracy scoring function, as in operation 2010. If indications are that one or more parts of the evaluation criteria are not met following training operation 2008, said test data is sent back through machine the learning training process before re-evaluation.

In another embodiment, per operation 2012 once evaluation criteria are met within the operation 2010, the trained model weights and other parameters may be saved in a file (such as like a "pickle file," for example).

In a still further embodiment, per operation 2014 a model may be deployed and output generated by loading trained model for inference, providing input data, and making a prediction. During this process, the trained model may be deployed for inference by loading the weights and starting the inference process on new input data. Additionally, input data may be provided in the same format as the data used to train the model (as in operation 2008) to obtain the prediction array, and the resulting predictions may be interpreted to determine whether the simulation result is predicted to be successful. By way of non-limiting example, a ground location (AOI or GS, and optionally a date range and/or a TLE) may be provided to the machine learning model and the predicted response of the machine learning model generated to determine the chances of success, which may then used to obtain a prioritized list of AOI and date combinations based on chances of success as predicted by the machine learning model. In a related embodiment, a user may input a specific AOI/GS, along with a desired date range and TLE, and the resulting chances of success may be output.

In a further embodiment, Mission Administrators (MAs) and Mission Planners (MPs) may input different goals and different ranking criteria 2016 and the machine learning model(s) may be trained to rank accordingly by receiving direct input from said MAs and/or MPs to further guide model generation. For example, MAs may prioritize maximizing the command batch size, correlating with increased adjusted duration of passage at a ground station. MPs, on the other hand, may have a greater interest in maximizing the angle of elevation at a time of day to improve remote sensing and aerial survey quality and success. It should be noted that both MAs and MPs may use the trained machine learning model(s), accessed via a simple or complex user interface, to provide a specific command batch size or AOI, juxtaposed with desired passage date(s), to obtain a ranking or prediction of success for given transits/passages.

In various embodiments, within the context of operation 2004, the pre-processing of TLE data may include parsing TLE data to extract relevant parameters, parse a list of associated ground coordinates/AOI visited, extracting features, computing distance of AOI, a GS, and/or a Satellite Path (and/or distance from any).

Figure 21:
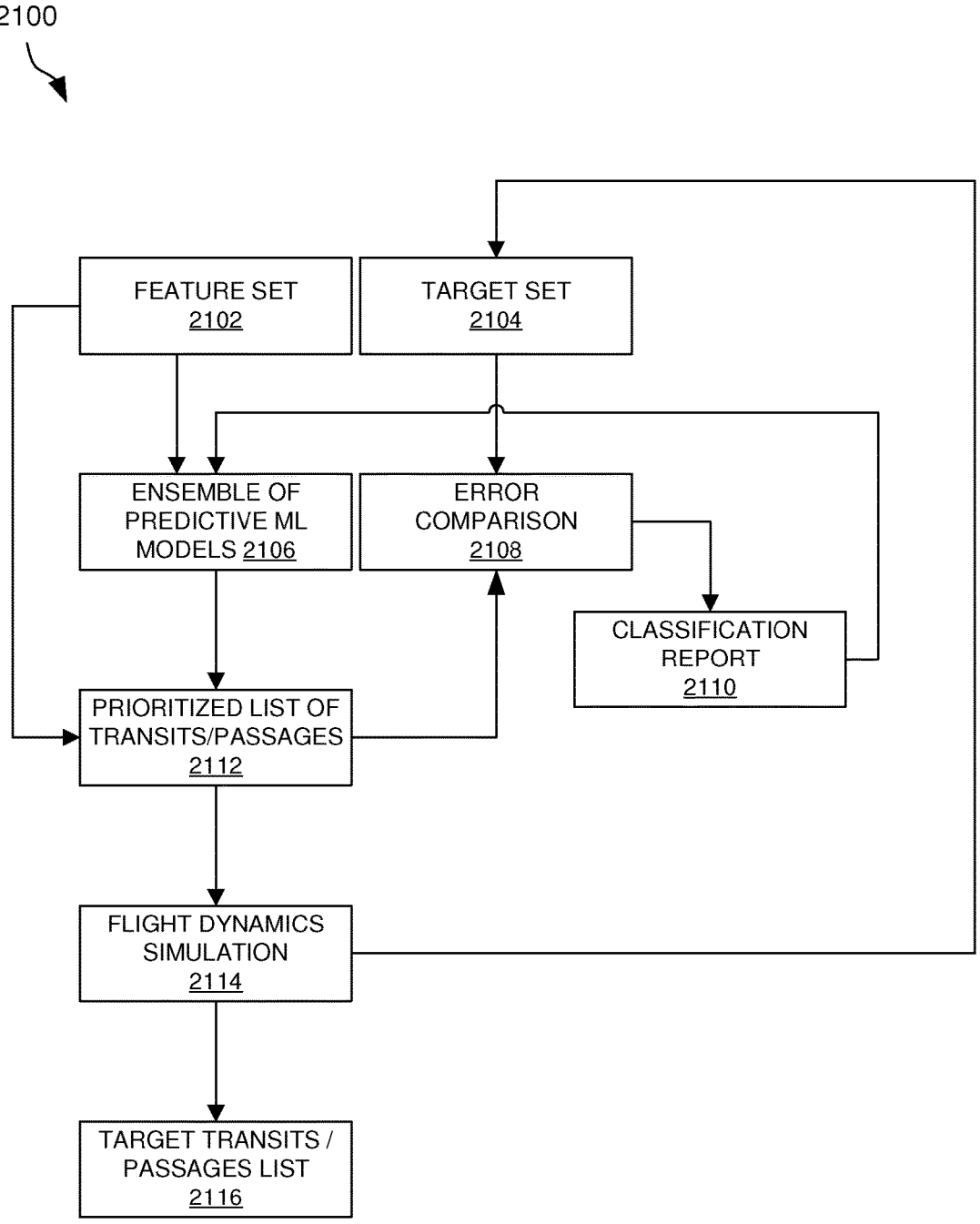
FIG. 21 illustrates a method designed to train a predictive machine learning model, in another embodiment.

FIG. 21 illustrates a method 2100 designed to train a predictive machine learning model. As an option, the method 2100 may be implemented in the context of any one or more of the embodiments set forth in any previous and/or subsequent figure(s) and/or description thereof. Of course, however, the method 2100 may be implemented in the context of any desired environment. Further, the aforementioned definitions may equally apply to the description below.

As shown, the method 2100 depicts a flowchart for evaluating and prioritizing satellite transits or passages using an ensemble of predictive machine learning (ML) models. The process begins with the input of a feature set 2102 into the ensemble of predictive ML models 2106. The feature set 2102 may include various characteristics or attributes of the satellite or its environment. In some aspects, the feature set may be a set of passages or transits obtained from Flight Dynamics Simulation. In some aspects, the feature set may be a set of passages or transits obtained from a generative machine learning model as in the generated list of passages 2210 in FIG. 22, which may be used during inference. In some aspects the feature set 2102 is available from historical data used for training. The target set may be obtained from historical data and/or from flight dynamics software and may provide the ranked list of passages.

The ensemble of predictive ML models 2106 processes the input data and results in a prioritized list of transits/passages 2112. The prioritized list of transits/passages 2112 may rank the predicted transits or passages according to their likelihood of occurrence or other relevant criteria, allowing for efficient scheduling and resource allocation.

In one embodiment, the prioritized list of transits/passages are compared against actual outcomes or benchmarks using an error comparison 2108. In one embodiment, the error comparison 2108 may be used to assess the accuracy and reliability of the predictions made by the ML models.

The error comparison 2108 leads to the generation of a classification report 2110, which provides detailed information about the prioritized list of transits/passages 2112, the performance of the ML models, (such as precision, recall, F1 score of the ML model of operation 2106). In one embodiment, the classification report 2110 may assist in understanding the strengths and weaknesses of the models in predicting satellite transits or passages.

In one embodiment, the error comparison 2108 may compare the prioritized list of transits/passages 2112 to a target set 2104, which may include the desired outcomes or predictions. Additionally, the error comparison 2108 may provide feedback back to the prioritized list of transits/passages and/or may generate the classification report 2110 which may be provided back to the ensemble of predictive ML models 2106, which may be used, in one embodiment, to further refine the ML models (for greater accuracy prediction and modeling).

The prioritized list of transits/passages 2112 is then used in a flight dynamics simulation 2114, which models the behavior of the satellites during the predicted transits or passages. The simulation provides insights into the expected satellite trajectories and operational parameters. In one embodiment, the flight dynamics simulation 2114 may be inputted as data to the target set 2104.

Finally, the simulation results are compiled into a target transits/passages list 2116, which serves as a reference for actual mission planning and execution. This list includes the transits or passages that are deemed to be the most viable and strategically valuable for the satellite mission.

Additionally, the method 2100 may be used to train a predictive machine learning model with TLE and ground location data (AOI and/or GS location with ground station availability data) along with other telemetry parametric data for time and date prediction or location prediction. In one embodiment, using specified TLE and ground location data, a trained predictive ML model may determine and/or prioritize satellite passage over available GSs (in the instance of telecommunications, for example) and/or over an AOI (as may be the case for surveying) for the best opportunity and best signal strength, which may be based on angle of elevation and transit duration, to achieve desired objectives. As such, the feature set 2102 may include a database of features, and a target set 2104 may include associated targets. Additionally, features for each passage or transit may include adjusted duration of passage (ADP), ratio of ADP to Total Duration of Passage (TDP), and one or more combinations of AOI+angle of elevation+time of day, and so on. Conversely, targets may be a set of rankings or confidence intervals that may indicate varying degree(s) of success. Such targets may also have originated rankings specifically created for training purposes based on past data gathered during recording and assessment processes.

In another embodiment, the error comparison 2108 function may be used to determine an error tolerance between a prediction and a target, wherein the resulting error tolerance is used to generate a classification report 2110. It is to be appreciated that an error tolerance may be multi-dimensional. In a related embodiment, the classification report 2110 may be presented in terms of correction parameters for model re-training and may be fed to an ensemble of machine learning models 2106 to further reduce the error in a next epoch of training. This method 2100 continues until the error is withing acceptable limits or until a maximum number of training epochs are completed, resulting in a prioritized list of transits/passages 2112 to be passed as working combinations to a flight dynamics simulator 2114. It should be noted that, at any time during the training process, predicted and corresponding input features from feature set 2102, target set 2104 (by way of error comparison function 2108), and the ensemble of machine learning models 2106 may be ranked on a per passage basis and may ultimately be passed as one or more additional combinations to flight dynamics simulator 2114 to verify the quality of prediction of success or the rank of a transit/passage among a list of transits or passages. During evaluation of new/hypothetical passages, ranked transit/passage parameters originating from flight dynamics simulator 2114 may be received and finalized as a collection desired/targeted transits/passages 2116.

Figure 22:
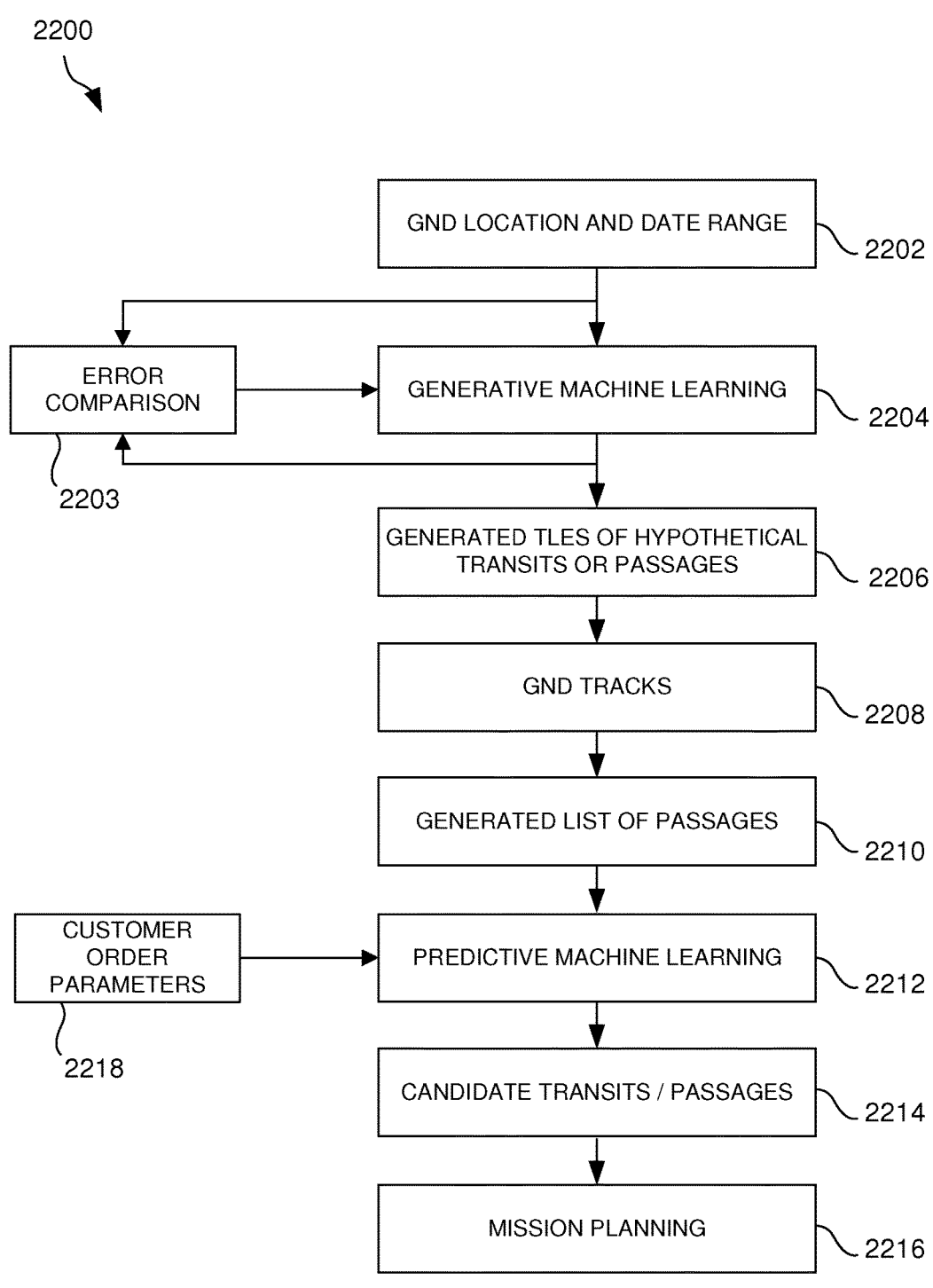
FIG. 22 illustrates a method for mission planning and mission administration, in another embodiment.

FIG. 22 illustrates a method 2200 of a flow diagram for mission planning and mission administration. As an option, the method 2200 may be implemented in the context of any one or more of the embodiments set forth in any previous and/or subsequent figure(s) and/or description thereof. Of course, however, the method 2200 may be implemented in the context of any desired environment. Further, the aforementioned definitions may equally apply to the description below.

Referring to the method 2200, the process begins with the input of a ground location and date range. See operation 2202. The ground location may be a specific geographical location on Earth, such as a city, a region, or a set of coordinates. The date range may be a specific period of time, such as a day, a week, or a month. The ground location and date range may be input by an operator, an automated system, or a combination of both. The input of the ground location and date range may be used to define the scope of the satellite mission and to determine the relevant parameters for the mission planning and control.

The input of the ground location and date range is then used by generative machine learning (operation 2204) to generate TLEs of hypothetical transits or passages (operation 2206). The generative machine learning 2204 may be a machine learning model that is trained to generate hypothetical transits or passages based on the input of the ground location and date range. The generative machine learning 2204 may use various techniques, such as generative adversarial networks (GANs), variational autoencoders (VAEs), or other suitable generative models, to generate the tiles of hypothetical transits or passages 2206.

The hypothetical transits or passages 2206 are then used to produce ground tracks. See operation 2208. The ground tracks may represent the predicted paths of the satellites over the ground location during a predetermined date range, time range, etc. The ground tracks may be generated using various algorithms and models, such as orbital mechanics models, flight dynamics models, and machine learning models. The ground tracks may be visualized on a map or a globe to provide a visual representation of the predicted paths of the satellites.

Next, the hypothetical transits or passages, and/or the ground tracks, are then compiled into a generated list of passages/transits. See operation 2210. The generated list of passages and transits may include various information, such as the predicted times of the transits or passages, the predicted locations of the satellites during the transits or passages, the predicted elevations of the satellites during the transits or passages, and other relevant information. The generated list of passages may be used for various purposes, such as mission planning, satellite scheduling, resource allocation, or other suitable purposes.

The generated list of passages is then evaluated by predictive machine learning (per operation 2212) to identify candidate transits or passages (per operation 2214). The predictive machine learning may be a machine learning model that is trained to predict the likelihood of a transit or passage occurring based on the generated list of passages (per operation 2210). The predictive machine learning may use various techniques, such as regression models, classification models, or other suitable predictive models, to identify the candidate transits or passages. Additionally, customer order parameters (per operation 2218) may be inputted into the predictive machine learning per operation 2212. The customer order parameters may be used to rank for future passages.

The candidate transits or passages are then used for mission planning. See operation 2216. The mission planning may involve various operations, such as scheduling the satellite operations, allocating the satellite resources, generating the satellite commands, and other relevant operations. The mission planning may be performed by an operator, an automated system, or a combination of both. The mission planning may use the candidate transits and/or passages to optimize the satellite operations and to achieve the mission objectives.

In other embodiments, the method 2200 may comprise multiple sub-flows and methods used for mission planning and mission administration which may predict passages/transits of a satellite or a constellation of satellites for points further in the future. Where information may be required for more than one week to a few months (i.e., perhaps even six months) into the future for mission planning, the satellite transits over a ground location such as an AOI or a passage over a ground station may not be computed reliably using flight dynamic software with a high degree of confidence in a short amount of time with high computational efficiency. There are many factors such as precision of earth, solar activity, etc., that can affect the trajectories of satellites. However, given a year's worth of actual transit data comprising TLEs, ground tracks, angles of elevation, etc., machine learning is used herein to generate candidate TLE and ground track data for protracted-date hypothetical transits/passages into the future that are of interest to a mission planner.

In one embodiment, an initial generative machine learning model (such as that produced according to the method described in the method 2100) may be passed to the method 2200, wherein the data set comprises the TLE and one or more features used for training. This training process is continuous, designed to correct the training machine learning model using the actual data obtained during every iteration (which is may typically be within seconds, minutes, hours, or perhaps daily).

In operation, during protracted date range analysis, a ground (GND) location (e.g., an AOI or GS) and a date range (per operation 2202) may be provided to the trained generative machine learning (ML) model (per operation 2204), which may perform one or more inferences and may generate a set of hypothetical TLEs for hypothetical transits/passages (per operation 2206) associated with specified GND locations. Additionally, an additional error comparison function (per operation 2203) may be employed to further determine an error tolerance between a prediction and a target before being passed to generative ML model (per operation 2204). It is to be appreciated that, over the course of processing, one or more hypothetical TLEs and/or hypothetical transits/passages (of the operation 2206) may not actually occur. Nevertheless, GND tracks (per operation 2208) may be calculated and a list of passages (per operation 2210) associated with GSs may be determined based on the hypothetical TLEs.

In a further embodiment, resulting data from operation 2010 may be fed as input to a predictive ML model 2212. In one embodiment, the resulting data from operation 2010 may be accompanied by customer order parameters, which may rank the AOI-to-transit combinations and ground station-to-transit/passage combinations in an effort determine the best candidate month/date (and time, optionally) combinations. As such, a prioritized list of candidate transits/ passages (per operation 2214) may be created and provided to the mission planning and mission administration infrastructure (per operation 2216).

It should be noted that, in the case of a constellation of satellites, one additional degree of freedom that may be available for both the machine learning model and the mission planner is the ability to match satellites with one or more "best" transits (based on angle of elevation) or passage (over a ground station, for example, based on the longest and best adjusted duration of passage).

In a related embodiment, it is to be appreciated that the method 2200 may work in a variety of scenarios: (1) where there may be a list of transits/passages in the near future, and the predictive ML may be used to rank the transits/passages for best outcomes; and (2) where there is no passage list for a protracted date period (e.g., a few weeks to a few months into the future), wherein the generative ML model 2204 may generate hypothetical TLEs and may be based on which hypothetical ground tracks 2208 may be computed, which may also comprise possible/plausible transits/passages over GND locations (or AOIs) of interest using the generative ML model 2204 trained on historic data with possible angles of elevations, TLE, and other parameters. Thereafter, predictive ML may be used to rank the transits/passages and produce one or more "best" outcomes. It is envisioned that other scenarios may relate to the method 2200, and therefore the examples provided herein are intended merely as some examples (but not all).

Figure 23:
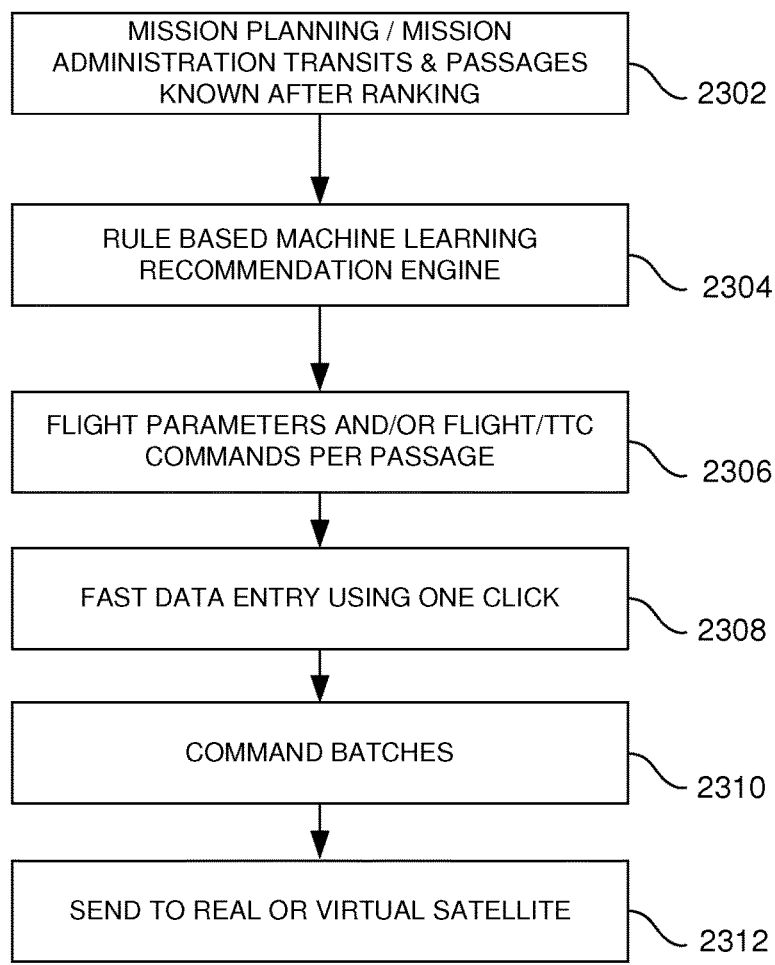
FIG. 23 illustrates a method for parameter and command generation for flight control, in another embodiment.

FIG. 23 illustrates a method 2300 for parameter and command generation for flight control. As an option, the method 2300 may be implemented in the context of any one or more of the embodiments set forth in any previous and/or subsequent figure(s) and/or description thereof. Of course, however, the method 2300 may be implemented in the context of any desired environment. Further, the aforementioned definitions may equally apply to the description below.

As shown, the method 2300 may comprise parameter and command generation for flight control and telemetry, tracking, and command (TTC) of satellite(s) in a constellation using a recommendation engine embedded in a declarative infrastructure, which may be used by mission administrators on an expert system that recommends a checklist of operations. It should be noted that the method 2300 may be used by both mission administrator(s) and mission planner(s), both of whom may comprise mission experts. For example, a mission planner's task may be to plan missions to satisfy a customer's orders related to the customer's payload using one or more satellites, which may include aerial survey and/or remote sensing of an area among other capabilities and tasks. A mission administrator's task, on the other hand, may be to control and command one or more satellites for specific purposes and monitor the health and functioning of those satellite(s).

In various embodiments, the declarative infrastructure may include a "one-click" operation (where more than one actions may be connected in a manner to implement various functions). For example, a "one click" operation may entail a preconfigured set of intent-based instructions such as "manage a constellation of satellites and orientate the satellite(s) to capture the best image of a predetermined location." Or, in another embodiment, a "one click" operation may include deployment of a satellite with a preconfigured set of settings (e.g. deploy satellite for surveillance, deploy satellite for communication, etc.). In another embodiment, the "one click" operation may include automation services, including if-this-then-that scenarios. In another embodiment, the "one click" operation may include deployment of containerized applications and virtual machines associated with the satellites, the mission control, the ground stations, etc. In short, therefore, the "one-click" operation may relate to configuration of the satellites in particular, and/or to management (such as via mission control, ground station, cloud datacenter, back-office, etc.) of the satellites in any manner.

In one embodiment, the method 2300 may comprise the process of receiving mission planning/mission administration transits and passages following ranking as produced in the method 2200. As such, the method 2300 begins with mission planning/mission administration receiving transits and passages known after ranking. See operation 2302.

Additionally, a rule based machine learning recommendation engine (per operation 2304) may be applied to the transits and passages. In one embodiment, the rule based machine learning recommendation engine may include an expert system trained by mission experts that may be used to automatically create commands designed to control and/or communicate with a satellite. In operation, commands may be created using templates based on checklist(s) of action(s) recommended by recommendation engine (per the operation 2304). Thereafter, the recommendation engine may produce one or more correct checklist(s) based on actions required to be communicated for flight parameters and/or flight/TTC commands per operation 2306, (e.g., action in the launch and early orbit phase (LEOP) phase of a satellite, actions for normal operation, actions to control payload, for some special payload handling, or for some exception handling, etc.)

In another embodiment, the data output of operation 2306 may then be associated with a declarative infrastructure that may receive flight control parameters generated and translate them to a fast data entry using "one click." See operation 2308. In one embodiment, the commands may be transposed into smart micro command batches (per operation 2310) for deployment to the satellite (per operation 2312) via a suitable GS. It is to be appreciated that, during testing and simulation, commands may alternatively be uploaded into a virtual satellite in a virtualized simulation environment, also performed by deployment to the satellite per operation 2312.

In a related embodiment, the method 2300 may itself be embedded in a declarative infrastructure and framework (such as those exemplified in FIG. 24 and FIGS. 9A, 9B, and 9C, at a minimum) that may allow human operators to perform mission planning, administration, and control using simple commands.

In various embodiments, the method may also include a fast data entry subsystem with one-click declarative infrastructure that receives flight control parameters and/or Flight commands and/or TTC commands for a passage. The fast data entry subsystem may provide a user-friendly interface that allows operators to quickly and easily input the flight control parameters and/or Flight commands and/or TTC commands. The one-click declarative infrastructure may provide a simple and intuitive way for operators to specify the desired state of the satellites and the system, and to declare the actions or operations that are to be performed to achieve the desired state.

The one-click declarative infrastructure may use various techniques, such as form-based input, drag-and-drop input, voice input, or other suitable input techniques, to facilitate the fast data entry. The one-click declarative infrastructure may also provide various features, such as auto-completion, error checking, validation, or other suitable features, to assist the operators in inputting the flight control parameters and/or Flight commands and/or TTC commands.

In some aspects, the fast data entry subsystem with one-click declarative infrastructure may be integrated with the rule-based machine learning recommendation engine 2304. The rule-based machine learning recommendation engine 2304 may generate the recommended flight parameters and/or flight/TTC commands, and the fast data entry subsystem with one-click declarative infrastructure may allow the operators to quickly and easily input the recommended flight parameters and/or flight/TTC commands. This can help to streamline the process of determining and inputting the flight parameters and/or flight/TTC commands, and to improve the efficiency and effectiveness of the satellite constellation management and control system.

Figure 24:
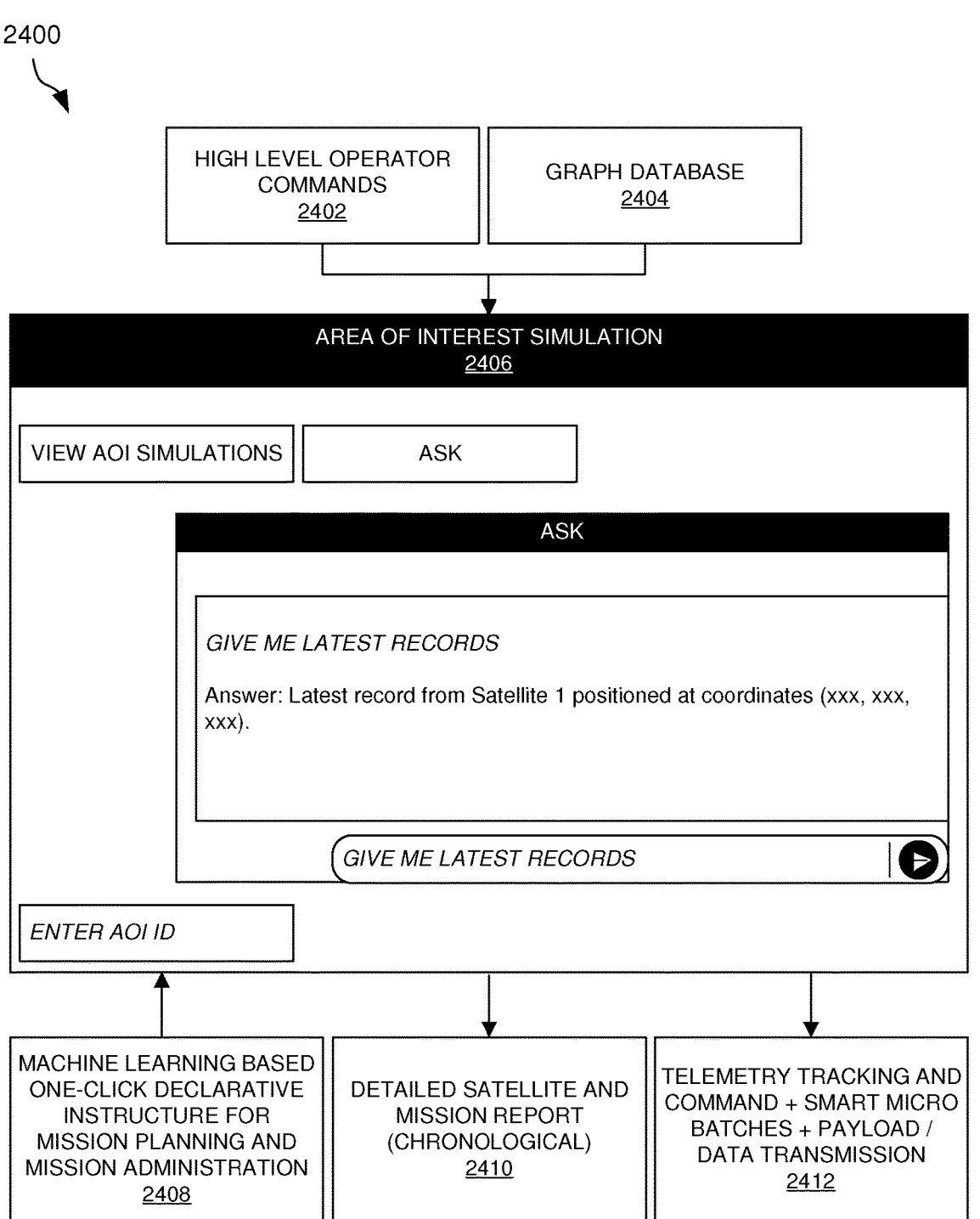
FIG. 24 illustrates a system for machine learning-based declarative infrastructure for automated mission planning, mission administration, and control, in another embodiment.

FIG. 24 illustrates a system 2400 for machine learning-based declarative infrastructure for automated mission planning, mission administration, and control, in accordance with one embodiment. As an option, the system 2400 may be implemented in the context of any one or more of the embodiments set forth in any previous and/or subsequent figure(s) and/or description thereof. Of course, however, the system 2400 may be implemented in the context of any desired environment. Further, the aforementioned definitions may equally apply to the description below.

As shown, the system 2400 may comprise several capabilities including historic satellite mission planning, administration, control, and flight data for one or more satellites of a constellation controlled by high level operator commands 2402 (e.g., one or more UI/UX interfaces for human operators, etc.) and stored in a database such as a graph database 2404. The graph database 2404 may include remote sensing data (such as AOI, mineral data, industry data, cost/pricing data, etc.).

In one embodiment, the system 2400 may comprise an AOI simulation 2406. Such an AOI simulation 2406 may include a variety of user interface features and interactions, including the ability to view current and/or past AOI simulations, the ability to enter and search for an AOI ID (for previously generated simulations), and an interactive module (titled "ASK") which may allow a user to request and/or ask questions and receive responses accordingly.

In another embodiment, AOI simulation 2406 may provide detailed reports 2410 of satellite missions and flights collated chronologically. Additionally, the system 2400 may further provide various data 2412 including TTC data and commands formatted for smart batching into micro-batches of appropriate sizes targeted for specific passages/transits over specific ground stations and for convenient and accurate data transmission to and from the satellite(s).

In various embodiments, the graph database data 2404 may be used to support various operations and functions of the system 2400. For example, the graph database 2404 may be used to provide data for visualizations, reports, alerts, and other information presented on the user interface. Additionally, the graph database 2404 may also be used to support search and query operations, data analysis operations, data mining operations, and other data-related operations.

The area of interest simulation 2406 may receive input from a machine learning-based one-click declarative infrastructure for automated mission planning, mission administration, and control 2408. The machine learning-based one-click declarative infrastructure may use machine learning algorithms to automate various aspects of mission planning, mission administration, and control. For example, the machine learning-based one-click declarative infrastructure may use machine learning algorithms to predict the future state of the satellites, optimize the scheduling of satellite operations, or detect anomalies in the satellite data.

In some cases, the machine learning-based one-click declarative infrastructure may include a user interface that allows operators to input commands and parameters using a one-click mechanism. The one-click mechanism may provide a simple and intuitive way for operators to specify the desired state of the satellites and the system, and to declare the actions or operations that are to be performed to achieve the desired state. The one-click mechanism may use various techniques, such as form-based input, drag-and-drop input, voice input, or other suitable input techniques, to facilitate the fast data entry.

In some aspects, the machine learning-based one-click declarative infrastructure may be integrated with the graph database 2404. For example, the graph database 2404 may provide the data for the machine learning algorithms, and the machine learning-based one-click declarative infrastructure may use the data to make predictions, optimize operations, and generate commands. This integrated approach can improve the efficiency and effectiveness of the satellite constellation management and control system.

Figure 25:
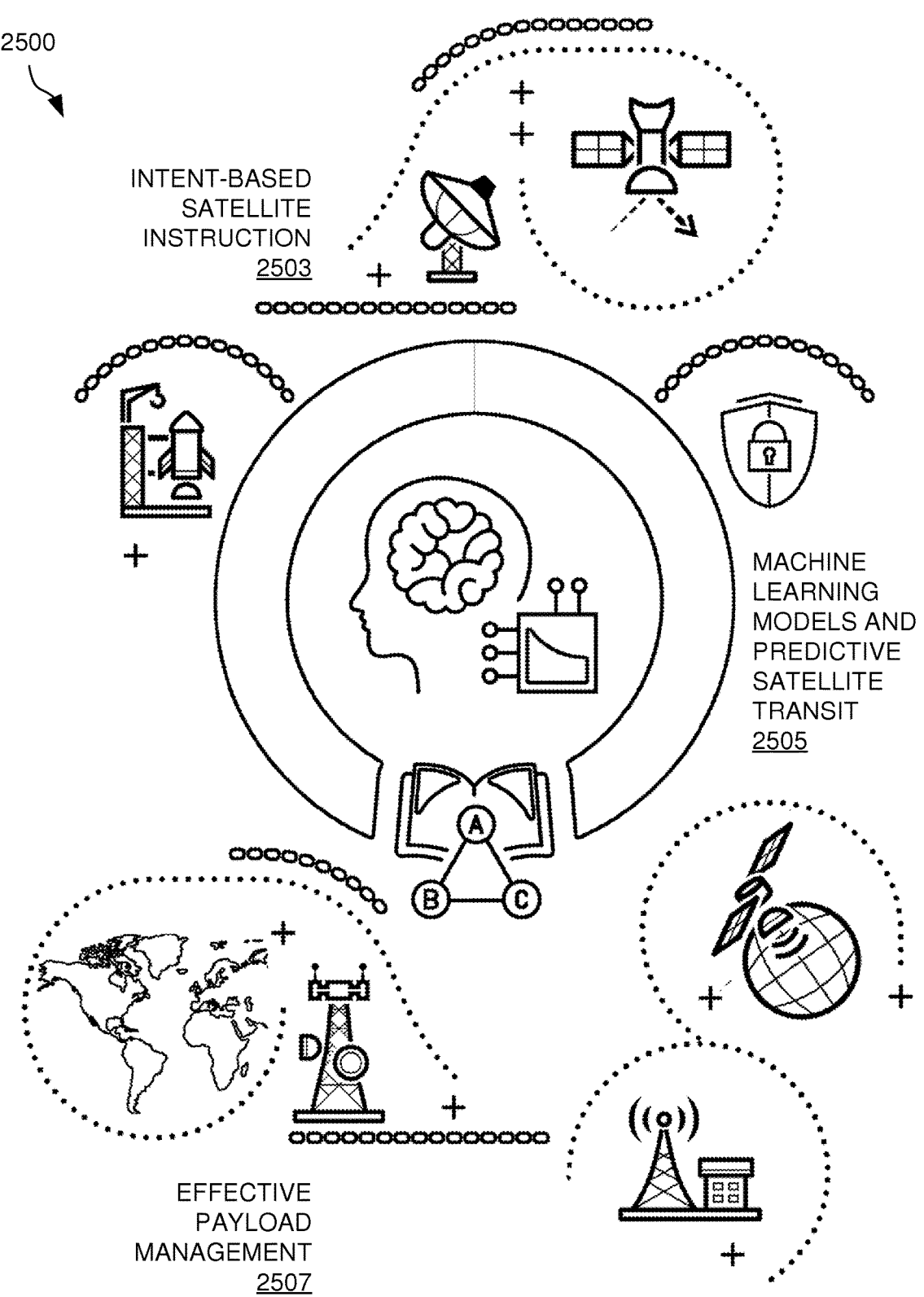
FIG. 25 illustrates an intent-based satellite instruction system, in accordance with one embodiment.

FIG. 25 illustrates an intent-based satellite instruction system 2500, in accordance with one embodiment. As an option, the system 2500 may be implemented in the context of any one or more of the embodiments set forth in any previous and/or subsequent figure(s) and/or description thereof. Of course, however, the system 2500 may be implemented in the context of any desired environment. Further, the aforementioned definitions may equally apply to the description below.

As shown, an intent-based satellite instruction 2503 may be associated with machine learning models and predictive satellite transit 2505, as well as effective payload management 2507. In one embodiment, the effective payload management 2507 may include command and control (TTC) data as well.

In operation, the intent-based satellite instruction 2503 may include intended outcomes, states, tasks, etc. associated with a satellite to fulfill.

The machine learning models and predictive satellite transit 2505 may be used to train and use machine learning models to accurately predict satellite transit paths. Such prediction may be used to allocate one or more intent-based satellite instruction to an intended satellite. As such, a ground-based control station may allocate tasks (i.e. intent based instruction) to one or more satellites based on predictive transit paths.

The satellites, in turn, may receive the intent-based instruction for more minute implementation and execution. For example, real-time in-situ measurements (during actual satellite transit) may be used to determine and configure commands to implement and fulfill the intent-based instruction. In one embodiment, the intent-based instruction may include rules based expert systems.

For example, a rules-based expert system may be used to create commands for the one or more pre-determined outcome. Furthermore, the rules-based expert system may query one or more neural network based artificial intelligence agents to provide certain services or data automatically when queried using their knowledge or training of various environments. For example, a rules-based expert system may query about cloud cover conditions and the AI agent for real-time or predictive atmospheric conditions could provide data to the rules-based expert system.

After completing the intent-based instruction, the satellite will likely have obtained data (e.g. images, atmospheric measurements, etc.) to be delivered back to the ground-based control stations. The payload may be coordinated for delivery by: 1) segmenting the payload into multiple micro-batch packets; and 2) assigning the micro-batch packets for delivery to the ground-based control stations in an effective manner. For example, typical current payload delivery systems include having a single ground station communicate with a satellite. Even if the satellite were to segment the payload into micro-batches, the transmission to the one ground station could take several transit passes before completion. In contrast, the systems disclosed herein provide a mechanism for coordination amongst multiple ground-based control stations such that a first micro-batch packet may be sent to the first ground station to be passed by the satellite during the transit path, the second micro-batch packet may be sent to the second ground station to be passed by the satellite during the transit path, and so on and so forth. The ground-based control stations may then coordinate aggregating the micro-batches into one cohesive payload package.

In some aspects, the techniques described herein relate to an intent-based satellite management system, including one or more satellites in a constellation and a ground-based control system to manage the one or more satellites. Additionally, the system may include a communication module configured to transmit intent-based instruction from the ground-based control system to the one or more satellites, where the intent-based instruction includes one or more predetermined outcomes. Further an intent-based module may be included, located on each satellite of the one or more satellites, configured to receive the intent-based instruction and instruct a processor to generate and execute command sequences in order to fulfill the intent-based instruction.

In various embodiments, the intent-based module may use a neural network to generate the command sequences. Additionally, the intent-based instruction may include a set of high-level goals for the satellite mission.

In various embodiments, the intent-based instruction may be based on coarse-grained prediction and fine-grained in-flight measurements. Additionally, the coarse-grained prediction may include workflow-based instructions pertaining to at least an entire orbit, and the fine-grained prediction may include measurements to carry out the workflow-based instructions based on then-current information associated with at least one satellite of the one or more satellites. Further, the intent-based instruction may be associated with a state of each satellite of the one or more satellites, and the command sequences may be configured as real-time commands to achieve the state.

In various embodiments, the command sequences may be configured for future execution. Additionally, the intent-based instruction may be provided by a user through a user interface. The user interface may include a natural language processing module for interpreting the user's intent. Further, the natural language processing module may use a neural network to interpret the user's intent.

In various embodiments, the intent-based module may use one of a deep learning model, a reinforcement learning model, a supervised learning model, an unsupervised learning model, or a semi-supervised learning model to generate the command sequences. Additionally, the command sequences may include one of telemetry tracking and control (TTC) commands, payload delivery commands, and/or flight dynamics commands. Further, the command sequences may be executed in real-time or near real-time, and/or the command sequences may be executed based on a schedule.

In various embodiments, the intent-based instruction may include an if-this-then-that configuration based on in-situ real-time measurements provided by any satellite of the one or more satellites. Additionally, the intent-base instruction may include taking a predetermined action associated an area of interest. Further, the command sequences may be executed based on the current and predicted future state of any (or a combination of any) of the satellite(s), the ground station, and the mission control station.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

The embodiments described herein included the one or more modes known to the inventor for carrying out the claimed subject matter. Of course, variations of those embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

What is claimed is:

1. A satellite optimization management system, comprising:

at least one processor configured to implement:

a natural language processing module configured to receive and interpret user input expressed in natural language to determine a user's intent and map it to specific tasks for a satellite, wherein the natural language processing module uses a neural network to determine the user's intent;

an execution module configured to generate and execute satellite command sequences based on operational tasks derived from the user's intent; and a communication interface configured to facilitate data transmission between the satellite and ground control, wherein the communication interface includes a data compression system that optimizes the data transmission by controlling a timing and sequencing of data to and from the satellite through segmentation into batches of data.

2. The satellite optimization management system of claim 1, wherein the natural language processing module includes a speech recognition system for receiving voice-based user input.

3. The satellite optimization management system of claim 1, wherein the natural language processing module includes a text analysis system for receiving text-based user input.

4. The satellite optimization management system of claim 1, wherein the neural network used by the natural language processing module is one of a recurrent neural network, or convolutional neural network.

5. The satellite optimization management system of claim 1, wherein the user's intent is interpreted by the natural language processing module by at least one of tokenization, part-of-speech tagging, named entity recognition, stemming, lemmatization, sentiment analysis, syntax, or grammar.

6. The satellite optimization management system of claim 1, wherein the execution module includes a command generation system or command execution system for generating the satellite command sequences.

7. The satellite optimization management system of claim 1, wherein the natural language processing module is configured to display a user interface to receive the user input.

8. The satellite optimization management system of claim 7, wherein the user input includes unstructured text relating to intent-based instructions for the satellite.

9. The satellite optimization management system of claim 8, wherein the intent-based instructions are based on coarse-grained prediction and fine-grained in-flight measurements.

10. The satellite optimization management system of claim 9, wherein the coarse-grained prediction includes workflow-based instructions pertaining to at least an entire orbit of the satellite, and the fine-grained in-flight prediction includes measurements to carry out the workflow-based instructions based on then-current information associated with the satellite.

11. The satellite optimization management system of claim 1, wherein the communication interface includes a data transmission protocol for managing the data transmission.

12. The satellite optimization management system of claim 1, wherein the communication interface includes a data transmission rate control system for controlling the rate of data transmission.

13. The satellite optimization management system of claim 1, wherein the communication interface includes a data transmission error detection and correction system for detecting and correcting errors in the data transmission.

14. The satellite optimization management system of claim 1, wherein the communication interface includes a data transmission scheduling system for scheduling the data transmission.

15. The satellite optimization management system of claim 1, wherein the communication interface includes a data transmission logging system for at least one of:
    logging the data transmission, or
    monitoring the data transmission and providing feedback on the data transmission.

16. The satellite optimization management system of claim 1, wherein the satellite optimization management system uses an expert system coupled to and controlled by an intent-based processing system.

17. The satellite optimization management system of claim 1, wherein the communication interface includes a data encryption system for securing the data transmission.

* * * * *